United States Patent
Folmer et al.

(10) Patent No.: US 8,669,256 B2
(45) Date of Patent: Mar. 11, 2014

(54) SUBSTITUTED THIENO[2,3-B]PYRAZINE COMPOUNDS AS MODULATORS OF B-RAF KINASE ACTIVITY

(75) Inventors: Brigitte Johanna Bernita Folmer, Oss (NL); de Adrianus Petrus Antonius Man, Oss (NL); Elisabeth Sophia Gernette, Oss (NL); Rita Corte Real Goncalves Azevedo, Oss (NL); Hemen Ibrahim, Oss (NL)

(73) Assignee: Merck Sharp & Dohme B.V., BN Haarlem (NL)

( * ) Notice: Subject to any disclaimer, the term of this patent is extended or adjusted under 35 U.S.C. 154(b) by 0 days.

(21) Appl. No.: 13/700,169

(22) PCT Filed: May 23, 2011

(86) PCT No.: PCT/EP2011/058329
§ 371 (c)(1),
(2), (4) Date: Nov. 27, 2012

(87) PCT Pub. No.: WO2011/147764
PCT Pub. Date: Dec. 1, 2011

(65) Prior Publication Data
US 2013/0079341 A1 Mar. 28, 2013

(30) Foreign Application Priority Data
May 28, 2010 (EP) .................................. 10164223

(51) Int. Cl.
*A61K 31/495* (2006.01)
(52) U.S. Cl.
USPC .......................... 514/249; 544/350
(58) Field of Classification Search
USPC .......................... 514/249; 544/350
See application file for complete search history.

(56) References Cited

FOREIGN PATENT DOCUMENTS

| WO | 2006024834 A1 | 3/2006 |
|---|---|---|
| WO | 2006024836 A1 | 3/2006 |
| WO | 2006040568 A1 | 4/2006 |
| WO | 2006081172 A2 | 8/2006 |
| WO | 2007002325 A1 | 1/2007 |
| WO | 2008157575 A1 | 12/2008 |
| WO | WO 2011/147764 | * 12/2011 |

OTHER PUBLICATIONS

Hackam, et al. JAMA, 296(14), 2006, 1731-1732.*
Jordan, V. C. Nature Reviews: Drug Discovery, 2, 2003, 205.*
Lyne, PD et al., Bioorganic & Medicinal Chemistry Letters, vol. 19, No. 3, (2009), pp. 1026-1029, "Identification of amidoheteroaryls as potent inhibitors of mutant (V600E) B-Raf kinase with in vivo activity".
Wermuth, CG, The Practice of Medicinal Chemistry, (1996), pp. 203-237, "Molecular variations based on isosteric replacements".
Korolkovas, A, Essentials of Medicinal Chemistry, 2nd Edition, Wiley & Sons, (1988), pp. 78-82.
Draber, W et al., Rational approaches to structure, activity and ecotoxicology of agrochemicals, (1992), CRC Press, p. 4.

* cited by examiner

Primary Examiner — Douglas M Willis
(74) Attorney, Agent, or Firm — Li Su; Laura M. Ginkel

(57) ABSTRACT

The invention relates to compounds according to general Formula (I) or a pharmaceutically acceptable salt thereof. The compounds can be used for the treatment of cancer.

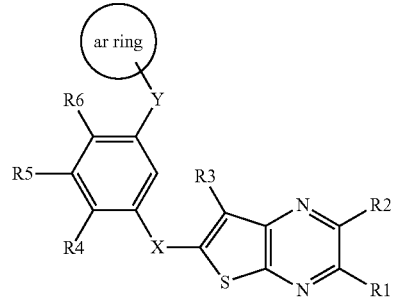

Formula I

17 Claims, No Drawings

SUBSTITUTED THIENO[2,3-B]PYRAZINE COMPOUNDS AS MODULATORS OF B-RAF KINASE ACTIVITY

CROSS-REFERENCE TO RELATED APPLICATIONS

The present application is the 35 U.S.C. §371 national stage prosecution of PCT international application serial no. PCT/EP2011/058329, filed on May 23, 2011, which claims the benefit under 35 U.S.C. §119(a) of EP application 10164223.9, filed on May 28, 2010, now expired.

STATEMENT REGARDING FEDERALLY SPONSORED RESEARCH OR DEVELOPMENT

Not Applicable

THE NAMES OF THE PARTIES TO A JOINT RESEARCH AGREEMENT

Not applicable

INCORPORATION-BY-REFERENCE OF MATERIAL SUBMITTED ON A COMPACT DISC

Not Applicable

BACKGROUND OF THE INVENTION

1. Field of the Invention

The present invention relates to new substituted thieno(2,3b)pyrazine derivatives, and salts or prodrugs thereof, to pharmaceutical compositions comprising these compounds and to their use in therapy, in particular to their use, either alone or in combination with at least one additional therapeutic agents, for the manufacture of a medicament in the prophylaxis or treatment of cancer.

2. Description of Related Art

Cellular growth, proliferation and differentiation are known to be regulated by receptor protein kinases. Via key signal transduction cascades many physiological functions are being controlled. In cancer cells, activation of signal transduction cascades results in tumor formation and growth, progression of the disease and metastasis of the tumor. The Ras/Raf/MEK/ERK pathway is one of the most important pathways in the regulation of cell growth and proliferation (Reviewed in e.g.: Wellbrock et al, Nat. Rev. Mol. Cell. Biol 2004; Kinkade et al, Curr. Canc. Ther. Rev. 2006, Michaloglou et al, Oncogene 2008). Signal transduction in this pathway starts with the activation of Ras (eg by growth factors). Upon activation of Ras, Raf is recruited to the plasma membrane and is phosphorylated and activated. Activated Raf in turn then phosphorylates and activates MEK, which in turn phosphorylates and activates ERK. Phosphorylated ERK then translocates to the nucleus and activates several downstream transcription factors.

Three Raf serine/threonine protein kinase isoforms have been reported, Raf-1 (C-Raf), A-Raf and B-Raf. These Raf kinases are highly homologous but have distinct biochemical functions, including differences in activation of the kinase pathways and tissue distribution. The basal kinase activity of B-Raf is considerably higher then of A-Raf and C-Raf (Chong et al, Cell Signal 2003).

Activation of the Ras/Raf/MEK/ERK pathway has been shown to stimulate cell cycle progression and is found in many tumors. Activating Ras mutations are found in several cancers (15% of human tumors have a Ras mutation), including pancreatic and colorectal tumors. B-Raf mutations are frequently found in melanomas (45-68% of melanomas have a B-Raf mutation), thyroid tumors (10-54%), ovarian tumors (31-36%) and colorectal tumors (9%) (Davies et al, Nature 2002; Khazak et al, Expert Opin. Ther. Targets 2007).

The most frequent mutation in B-Raf is a replacement of a valine at position 600 in a glutamic acid. The presence of a $Glu^{600}$ in the mutated form obviates the need for phosphorylation, resulting in uncoupling of the Ras/Raf/MEK/ERK activating pathway and in constitutively active B-Raf (Wan et al, Cell 2004, Gray-Schopfer et al, Nature 2007).

In the Ras/Raf/MEK/ERK pathway, the Raf protein kinases play a central role and have been shown to be critical for mediating cell proliferation in various cancer models. Therefore it can be expected that B-Raf inhibitors are of therapeutic use in the treatment of tumors which are dependent on this pathway as a single agent therapy. Moreover, administration of a Raf inhibitor in combination with a chemotherapeutic agent (such as temozolomide or paclitaxel/docetaxel) can be of benefit for patients with tumors dependent on the Ras/Raf/MEK/ERK pathway. Furthermore, it has been reported that in melanomas both the Ras/Raf/MEK/ERK pathway as well as the PI3K/Akt/mTor pathway are drivers of tumor growth and progression. Intervention of both pathways by the combined treatment of a Raf inhibitor and an inhibitor of the PI3K pathway could be a valuable therapy (Smalley et al, Brit. J. Canc. 2009).

Quinoxalines as B-Raf inhibitors are disclosed in AstraZeneca application WO 06040568. Quinoazolinone derivatives are disclosed as B-Raf inhibitors in application WO 06024834 (WO 06024836). Quinazoline carboxamides and thiazole carboxamides are described in international application WO 08157575 and WO 06081172.

BRIEF SUMMARY OF THE INVENTION

A need exists for compounds that inhibit B-Raf and intervene with the activated Ras/Raf/MEK/ERK pathway, for the treatment of human cancers driven by the activation of this pathway.

The present application is based on thienopyrazine derivatives which are novel B-Raf inhibitors and it is expected that these compounds could possess beneficial efficacy, and or improved pharmakinetic (pharmacodynamic) profiles and or toxicological profiles that makes them particularly useful in the treatment of neoplastic diseases. To that aim, the present invention provides imidazoiso[5,1-a]quinoline and 5,6-dihydro-imidazoiso[5,1-a]quinoline derivatives.

BRIEF DESCRIPTION OF THE DRAWINGS

Not Applicable

DETAILED DESCRIPTION OF THE INVENTION

More specifically, the present invention provides thieno(2,3b)pyrazine compounds according to Formula I

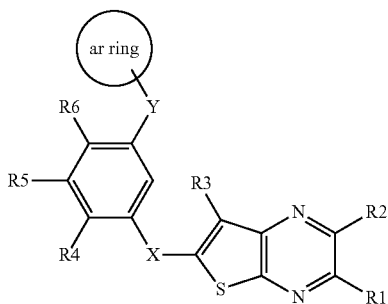

Formula I or a pharmaceutically acceptable salt thereof.

In this formula R1 through R6, X, Y and ar ring have the following definitions: One of R1 and R2 is H; halogen; hydroxy; CN; amino; (1-2C)alkyl; (1-2C)alkylcarbonyl; (1-2C)alkoxy or (di)[(1-2C)alkyl]amino, the alkyl group of which is optionally substituted with hydroxy; whereas the other of R1 and R2 is H; halogen; hydroxy; CN; amino; (1-6C)alkyl; (1-6C)alkoxy; (di)[(1-6C)alkyl]amino, the alkyl group of which is optionally substituted with one or more hydroxy, (di)[(1-4C)alkyl]amino, (1-6C)alkoxy, (2-5C)heterocycloalkyl, (2-5C)heteroaryl; (1-6C)alkylcarbonyl; (2-5C)heterocycloalkyl, optionally substituted with one or more groups selected from hydroxy, amino, (1-6C)alkyloxycarbonylamino) and (1-6C)alkyl, which is optionally substituted with hydroxy; (2-5C)heteroaryl or (2-5C)heteroarylamino, both optionally substituted with halogen, CN, (1-6C)alkoxy, (di)[(1-6C)alkyl]amino or (1-6C)alkyl; phenyl or phenylamino, both optionally substituted with halogen, CN, (1-6C)alkyl, (1-6C)alkoxy or (di)[(1-6C)alkyl]amino or the other of R1 or R2 is (2-5C)heterocycloalkylamino.

R3 is H; amino; halogen; hydroxy; cyano; (1-6C)alkyl; (2-6C)alkenyl; (2-6C)alkynyl; (di)[(1-4C)alkyl]amino, (1-4C)alkylcarbonylamino, the alkyl group of which optionally is substituted with halogen; or phenylalkyl, the phenyl group of which is optionally substituted with halogen.

R4 is (1-4C)alkyl; halogen or cyano.

R5 and R6 are independently H or halogen.

X is NHCO; CONH; N=C(CN); NHCH2; NHSO2, SO2NH or CO.

Y is CONH; NHCO; NHCONH, NHSO2 or SO2NH.

ar ring is an aryl ring selected from (2-5C)heteroaryl substituted with one or more groups selected from halogen, (1-6C)alkyl, phenyl, (2-5C)heterocycloalkyl or (di)[(1-6C)alkyl]amino optionally substituted with (1-6C)alkoxy, OH, or (di)[(1-6C)alkyl]amino;

or phenyl having Formula II

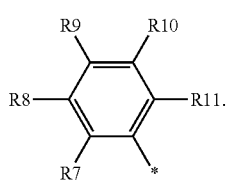

Formula II

Within Formula II R7 through R11 have the following definitions:

R7 and R11 are independently H; halogen; (1-6C)alkyl; (di)[(1-6C)alkyl]amino or amino.

R8, R9 and R10 are independently H; halogen; amino; (1-6C)alkyl, optionally substituted with one or more CN, aminocarbonyl, halogen, hydroxy, phenyl or: (2-5C)heterocycloalkyl; (1-6C)alkoxy, optionally substituted with one or more halogen, hydroxy and (1-6)alkoxy; (di)[(1-6C)alkyl]amino, optionally substituted with phenyl; (2-5C)heteroaryl; (2-5C)heterocycloalkyl, optionally substituted with cyano or (1-6C)alkyl; (di)[(1-6C)alkyl]amino); (1-6C)alkylcarbonyl or phenylamino.

The asterisk in Formula II indicates the attachment point to Y in Formula I

The thieno(2,3b)pyrazine derivatives according to the present invention are potent B-Raf inhibitors and can be used as therapeutical agent, in particular they may be used for the treatment of proliferating diseases by administering to patients in need thereof.

The term (1-2C)alkyl as used in the definition means an alkyl group having 1 or 2 carbon atoms, being methyl or ethyl.

The term (1-4C)alkyl as used in the definition means a branched or unbranched alkyl group having 1-4 carbon atoms, being methyl, ethyl, propyl, isopropyl, butyl, isobutyl, sec-butyl and tert-butyl.

The term (1-6C)alkyl means a branched or unbranched alkyl group having 1-6 carbon atoms, for example methyl, ethyl, propyl, isopropyl, butyl, tert-butyl, n-pentyl and n-hexyl. (1-5C)Alkyl groups are preferred, (1-4C)alkyl being the most preferred.

The term (1-2C)alkylcarbonyl means an alkylcarbonyl group, the alkyl group of which contains 1 or 2 carbon atoms with the same meaning as previously defined.

The term (1-6C)alkylcarbonyl means an alkylcarbonyl group, the alkyl group of which contains 1-6 carbon atoms with the same meaning as previously defined.

The term (1-4C)alkylcarbonylamino means an alkylcarbonylamino group, the alkyl group of which contains 1-4 carbon atoms with the same meaning as previously defined.

The term (2-6C)alkenyl means a branched or unbranched alkenyl group having 2-6 carbon atoms, such as ethenyl, 2-butenyl, and n-pentenyl.

The term (2-6C)alkynyl means a branched or unbranched alkynyl group having 2-6 carbon atoms, such as ethynyl, propynyl and n-pentynyl.

The term (2-5C)heterocycloalkyl means a heterocycloalkyl group having 2-5 carbon atoms, preferably 3-4 carbon atoms, including 1-3 heteroatoms selected from N, O and/or S, which may be attached via a nitrogen if feasible, or a carbon atom. Preferred heteroatoms are N or O. Preferred number of heteroatoms is one or two. Most preferred are piperazinyl, tetrahydropyranyl, morpholinyl and pyrrolidinyl.

The term (2-5C)heterocycloalkylamino means a heterocycloalkylamino group, the heterocycloalkyl group of which contains 2-5 carbon atoms, preferably 3-5 carbon atoms, with the same meaning as defined previously.

The term (2-5C)heteroaryl means an aromatic group having 2-5 carbon atoms and 1-3 heteroatoms selected from N, O and S, like imidazolyl, thiadiazolyl, pyridinyl, thienyl or furyl. Preferred number of heteroatoms is one or two. Preferred heteroaryl groups are pyrimidinyl, furyl, pyrazolyl, thienyl and pyridinyl. Most preferred are pyrimidinyl, furyl, and pyridinyl The (2-5C)heteroaryl group may be attached via a carbon atom or a nitrogen, if feasible.

The term (2-5C)heteroarylamino means a heteroarylamino group, the heteroaryl group of which contains 2-5 carbon atoms with the same meaning and preferences as previously defined.

The term (1-2C)alkoxy means an alkoxy group having for 2 carbon atoms.

The term (1-4C)alkoxy means an alkoxy group having 1-4 carbon atoms, the alkyl moiety having the same meaning as previously defined. (1-3C)Alkoxy groups are preferred.

The term (1-6C)alkoxy means an alkoxy group having 1-6 carbon atoms, the alkyl moiety having the same meaning as previously defined. (1-4C)Alkoxy groups are preferred.

The term (1-6C)alkoxycarbonylamino means an alkoxycarbonylamino group, the alkoxy group of which contains 1-6 carbon atoms with the same meaning as previously defined.

The term (di)[(1-4C)alkyl]amino as used herein means an amino group, monosubstituted or disubstituted with alkyl group(s), each containing 1-4 carbon atoms and having the same meaning as previously defined.

The term (di)[(1-6C)alkyl]amino as used herein means an amino group, monosubstituted or disubstituted with alkyl group(s), each containing 1-6 carbon atoms and having the same meaning as previously defined.

The term halogen means fluorine, chlorine, bromine or iodine.

The term "substituted" means that one or more hydrogens on the designated atom is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

In the above definitions with multifunctional groups the attachment point is at the last group. The groups defined for Y and X are attached on both sides to the rest of the compound in the direction from the ar ring towards the thieno(2,3b) pyrazine group.

The term pharmaceutically acceptable salt represents those salts which are, within the scope of medical judgement, suitable for use in contact for the tissues of humans and lower animals without undue toxicity, irritation, allergic response and the like, and are commensurate with a reasonable benefit/risk ratio.

Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

In one aspect the invention relates to compounds of Formula I wherein X and Y are independently NHCO or CONH.

In another aspect the invention relates to compounds of Formula I wherein X is NHCO.

In yet another aspect the invention relates to compounds according to Formula I wherein Y is CONH.

In still another aspect the invention relates to compounds according to Formula I wherein the ar ring is (2-5C)heteroaryl substituted with one or more groups selected from (1-6C) alkyl, phenyl, (di)[(1-4C)alkyl]amino or pyrrolidinyl.

In still another aspect the invention relates to compounds according to Formula I wherein the ar ring is (2-5C)heteroaryl substituted with one or more groups selected from (1-6C) alkyl, (di)[(1-4C)alkyl]amino or pyrrolidinyl.

In another aspect the invention relates to the compounds according to Formula I wherein the ar ring is phenyl having Formula II

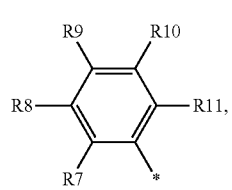

Formula II wherein R7 through R11 have the above identified meanings and wherein the asterisk indicates the attachment point to Y in Formula I.

In another aspect the invention relates to the compounds according to Formula I wherein the ar ring is phenyl having Formula II and wherein R8 in the phenyl ring is (1-4C)alkyl, optionally substituted with one or more CN, aminocarbonyl, halogen; (1-4C)alkoxy; (di)[(1-4C)alkyl]amino or (2-5C) heteroaryl.

In still another aspect the invention relates to the compounds according to Formula I wherein the ar ring is phenyl having Formula II and wherein R8 in the phenyl ring is (1-4C)alkyl, optionally substituted with one or more CN or halogen.

In another aspect the invention relates to the compounds according to Formula I wherein the ar ring is phenyl having Formula II and wherein R7, R9, R10 and R11 are H.

In another aspect the invention relates to the compounds according to Formula I wherein R1 is H; halogen; hydroxy; CN; amino; (1-2C)alkyl; (1-2C)alkylcarbonyl; (1-2C)alkoxy or (di)[(1-2C)alkyl]amino, the alkyl group of which is optionally substituted with hydroxy; and wherein R2 is H; halogen; hydroxy; CN; amino; (1-6C)alkyl; (di)[(1-6C)alkyl]amino, the alkyl group of which is optionally substituted with one or more hydroxy, (di)[(1-4C)alkylamino, (1-6C)alkoxy, (2-5C) heterocycloalkyl, (2-5C)heteroaryl or aryl; (1-4C)alkylcarbonyl; (1-4C)alkoxy, optionally substituted with (di)[(1-4C) alkyl]amino; (2-5C)heterocycloalkyl, optionally substituted with one or more groups selected from hydroxy, amino, (1-6C)alkyloxycarbonylamino; and (1-4C)alkyl, the alkyl optionally substituted with hydroxy; (2-5C)heteroaryl, optionally substituted with halogen, CN, (1-4C)alkoxy, (di) [(1-4C)alkyl]amino or (1-4C)alkyl; phenyl optionally substituted with halogen, CN, (1-4C)alkyl, (1-4C)alkoxy or (di)[(1-4C)alkyl]amino; 2-5C) heteroarylamino; phenylamino; or (2-5C)heterocycloalkylamino.

In another aspect the invention relates to the compounds according to Formula I wherein R1 is H; halogen; hydroxy; CN; amino; (1-2C)alkyl; (1-2C)alkylcarbonyl; (1-2C)alkoxy or (di)[(1-2C)alkyl]amino, the alkyl group of which is optionally substituted with hydroxy; and wherein R2 is H; halogen; hydroxy; CN; amino; (1-6C)alkyl; (1-6C)alkoxy; (di)[(1-6C)alkyl]amino, the alkyl group of which is optionally substituted with one or more hydroxy, (di)[(1-4C)alkylamino, (1-6C)alkoxy; (2-5C)heterocycloalkyl or (2-5C)heteroaryl; or (2-5C)heteroaryl.

In yet another aspect the invention relates to the compounds according to Formula I wherein R1 is H or (di)[(1-2C)]alkylamino, the alkyl group of which is optionally substituted with hydroxy.

In another aspect the invention relates to the compounds according to Formula I wherein R2 is H or (di)(1-2C)alkylamino, the alkyl group of which is optionally substituted with hydroxy.

In another aspect the invention relates to the compounds according to Formula I wherein at least one of R1 or R2 is H.

In another aspect the invention relates to the compounds according to Formula I wherein R3 is H; amino or (di)[(1-4C)alkyl]amino.

In another aspect the invention relates to the compounds according to Formula I wherein R5 and R6 are H.

The invention also relates to those compounds wherein all specific definitions for R1 through R11 and Y and X in the various aspects of the invention as defined hereabove occur in any combination within the definition of the thieno(2,3b)pyrazine compound of Formula I.

All compounds of the invention have an IC$_{50}$ of at least 1 µM.

In another aspect the invention relates to compounds of formula I which have an IC$_{50}$ of less than 100 nM. In yet another aspect the invention relates to compounds of formula I which have an IC$_{50}$ of less than 10 nM.

The term IC$_{50}$ means the concentration of the test compound that elicits half-maximal (50%) inhibition compared to the compound's maximally attainable effect. The values can be determined e.g. as described in example 77. Values can be determined using a software program such as Graphpad Prism 4.03 (GraphPad, San Diego, Calif.).

The compounds of this invention can be made according to the general processes described below in synthetic schemes A-J. The preparation of certain embodiments of the present invention is described in detail in the examples that follow the general schemes. Those of skill in the art will understand that the preparations can be readily adapted to prepare the other embodiments of the present invention by changing to other suitable reagents or by making modifications to the reaction conditions.

Scheme A

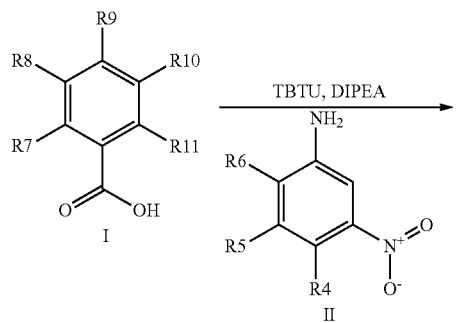

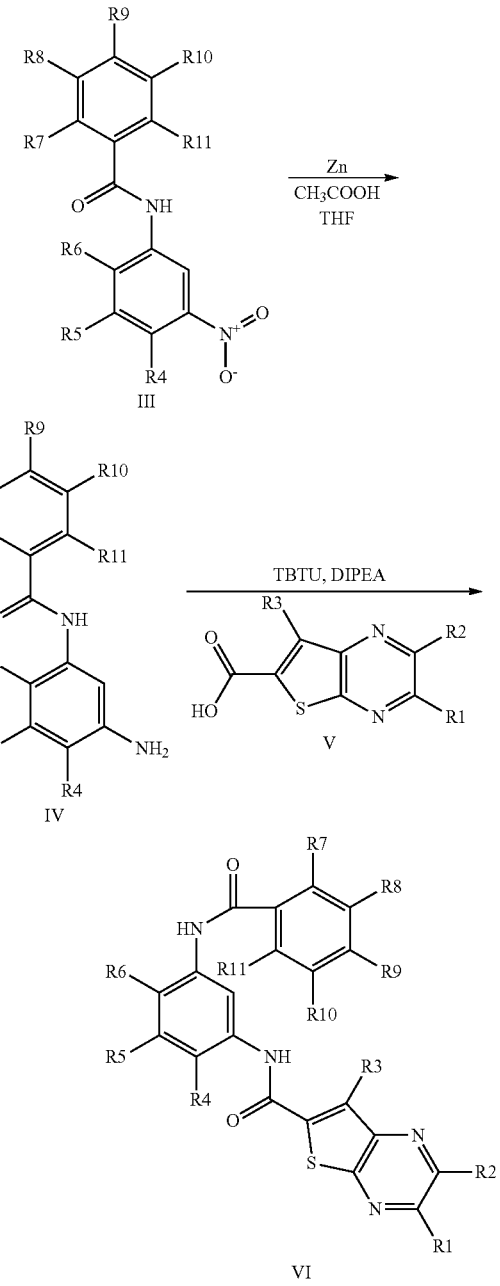

Substituted benzoic acids I can react with amines II, in the presence of an amide coupling agent such as TBTU or HATU and upon addition of a base such as DIPEA, to form amide derivatives III. Subsequently the nitro-group is reduced and amine IV is formed, this reduction can be accomplished with reducing agents such as zinc with acetic acid in THF. The amine can react with substituted thienopyrazine carboxylic acid V to give amide derivative VI. This amide coupling can be accomplished by a reaction of the acid and the amine in the presence of amide coupling agents such as TBTU or HATU in the presence of an amine such as DIPEA. Amine derivative IV can also react with a thienopyrazine acid chloride derivative, by heating in dioxane or at room temperature in solvents such as dichloromethane in the presence of a base such as triethylamine.

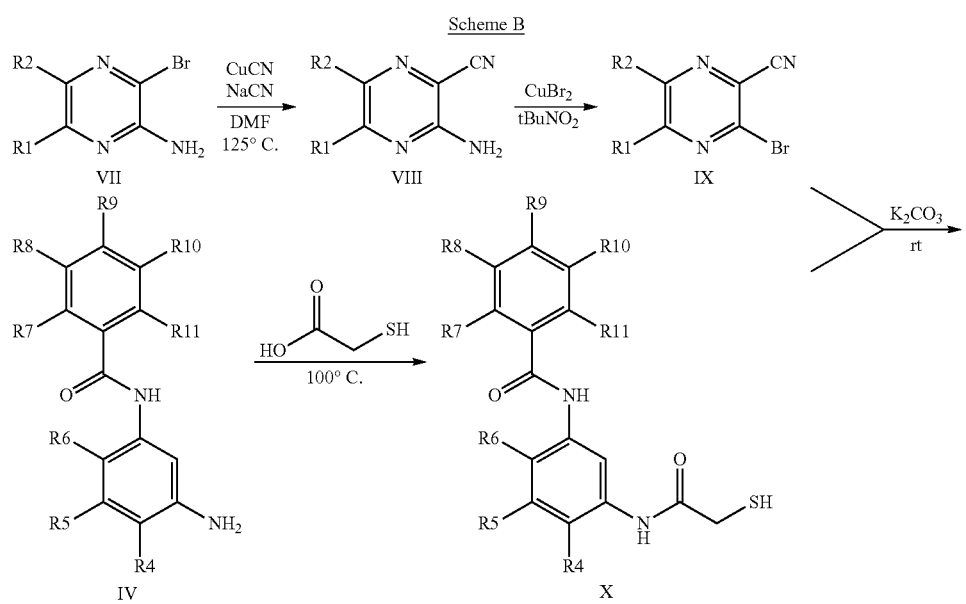

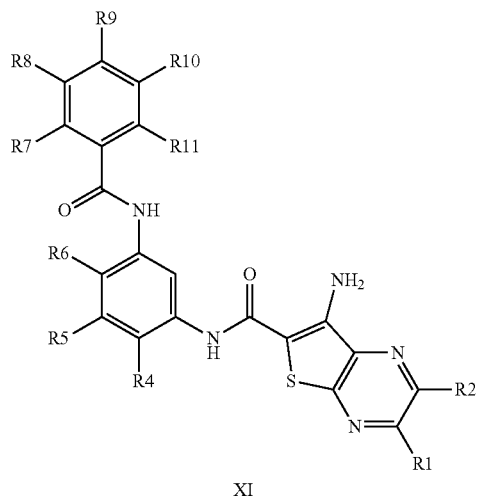

Compound XI, in which R3 is NH$_2$, can be obtained by following the general synthetic scheme outlined in scheme B. Starting with the bromo substituent of pyrazines VII, which can be replaced in a nitril functionality by reaction of VII with CuCN and NaCN in DMF at higher temperatures (125° C.). Under Sandmeyer conditions, such as with CuBr2 and tBuNO$_2$ the amine functionality of compound VIII can be transferred in a bromo-substituent and compound IX can be obtained. Amine IV can be converted in compound X by a reaction of the amine with mercapto acetic acid at elevated temperatures (100° C.). Coupling of IX and X can be accomplished in the presence of a base such as K$_2$CO$_3$ at room temperature, after heating to 50° C. cyclized product XI is obtained in good yields.

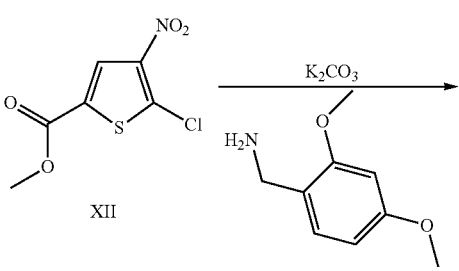

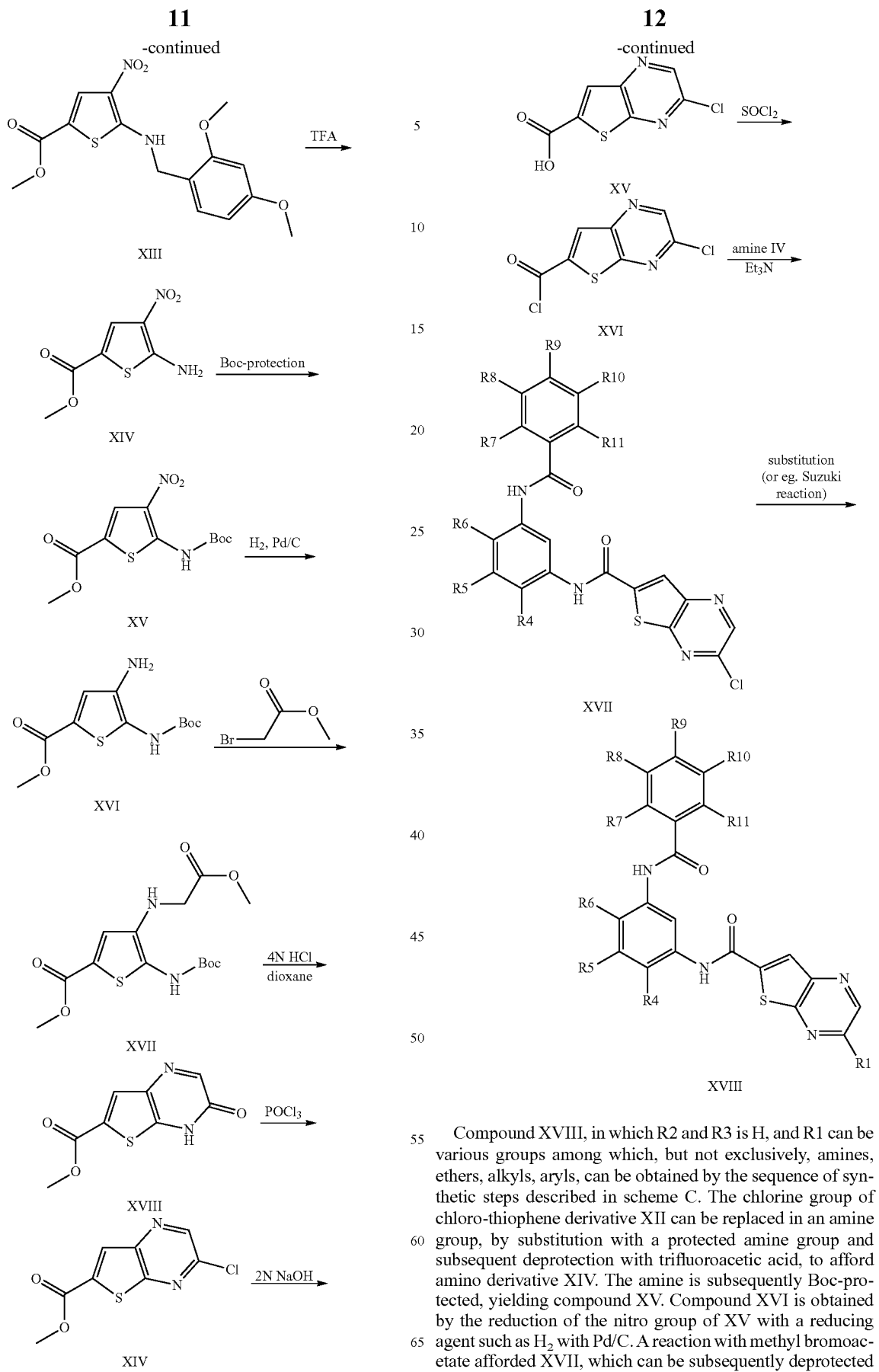

Compound XVIII, in which R2 and R3 is H, and R1 can be various groups among which, but not exclusively, amines, ethers, alkyls, aryls, can be obtained by the sequence of synthetic steps described in scheme C. The chlorine group of chloro-thiophene derivative XII can be replaced in an amine group, by substitution with a protected amine group and subsequent deprotection with trifluoroacetic acid, to afford amino derivative XIV. The amine is subsequently Boc-protected, yielding compound XV. Compound XVI is obtained by the reduction of the nitro group of XV with a reducing agent such as $H_2$ with Pd/C. A reaction with methyl bromoacetate afforded XVII, which can be subsequently deprotected and ringclosed with 4N HCl solution in dioxane to provide compound XVIII. A chlorine substituent is introduced by reaction of XVIII which POCl₃, yielding compound XIV. Saponification of the ester with NaOH yields the carboxylic acid derivative XV, which can be subsequently modified in acid chloride derivative XVI. Amide coupling of the acid chloride derivative XVI which amine IV yields amide derivative XVII. Finally, the chlorine substituent of XVII can be replaced in amine substituents XVIII (R1 is amine or substituted amines) by substitution reactions with amines, or reactions with alcohols to afford the corresponding ethers, or reaction with methyl zincchloride to afford the corresponding methyl derivative. Moreover, Suzuki reactions can afford the aryl (heteroaryl) substituted derivatives XVIII.

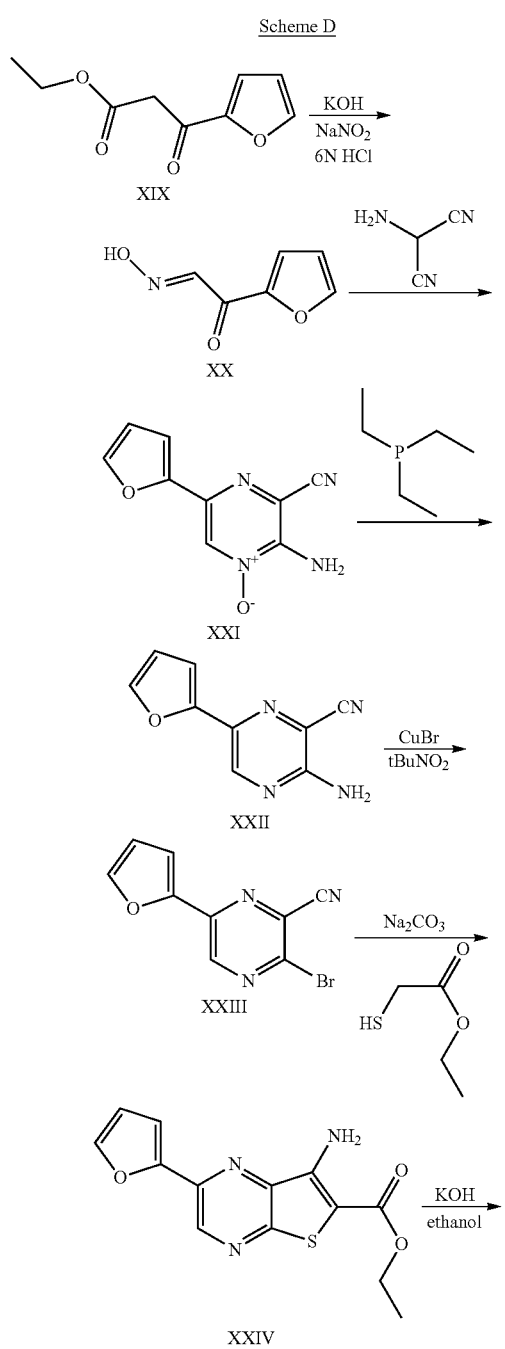

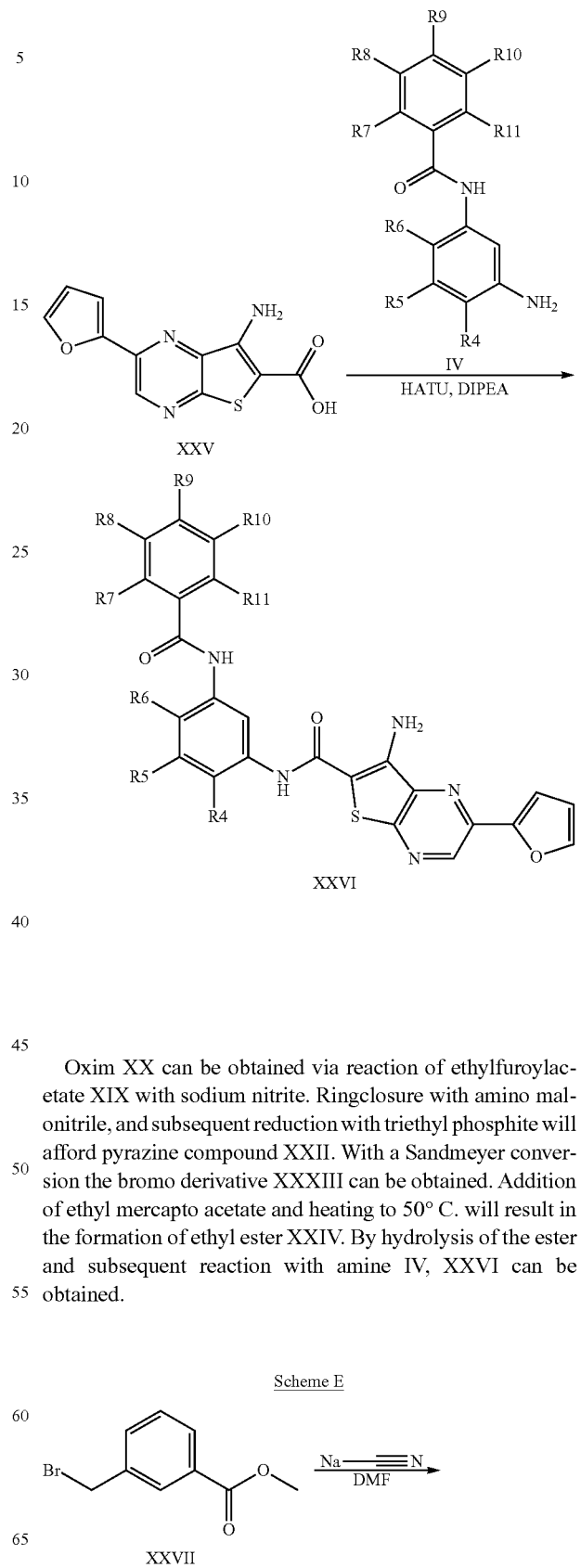

Oxim XX can be obtained via reaction of ethylfuroylacetate XIX with sodium nitrite. Ringclosure with amino malonitrile, and subsequent reduction with triethyl phosphite will afford pyrazine compound XXII. With a Sandmeyer conversion the bromo derivative XXXIII can be obtained. Addition of ethyl mercapto acetate and heating to 50° C. will result in the formation of ethyl ester XXIV. By hydrolysis of the ester and subsequent reaction with amine IV, XXVI can be obtained.

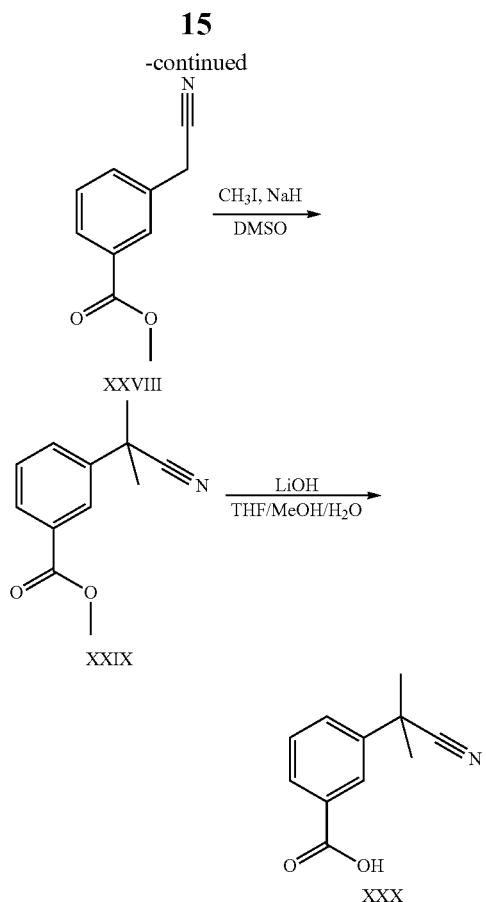

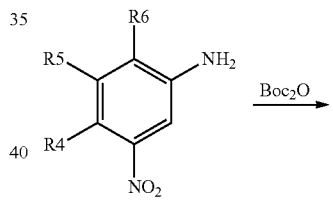

Substitution of the bromine functionality of XXVII in a nitril group can be accomplished upon addition of NaCN in DMF at room temperature, affording compound XXVIII in a high yield. Treatment of XXVIII with methyliodide results in the formation of dimethylnitril derivative XXIX. The ester can be hydrolysed with lithiumhydroxide in a mixture of THF/MeOH and H₂O. This transformation can also be accomplished in the presence of other bases, such as sodium hydroxide in water. Benzoic acid XXX can be reacted in a sequence of reaction steps as is described in general synthetic scheme A and G to yield derivative VI.

Introduction of the cyclopropyl group in benzoic acid XXXII can be accomplished by a reaction of nitril derivative XXVIII with a dihalide-ethane derivative. Subsequent hydrolysis with a base such as lithiumhydroxide or potassium hydroxide in aqueous mixtures such as THF/H₂O mixtures results in the formation of benzoic acide XXXII. Benzoic acid XXXII can be reacted in a sequence of reaction steps as is described in general synthetic scheme A and G, to yield derivatives VI.

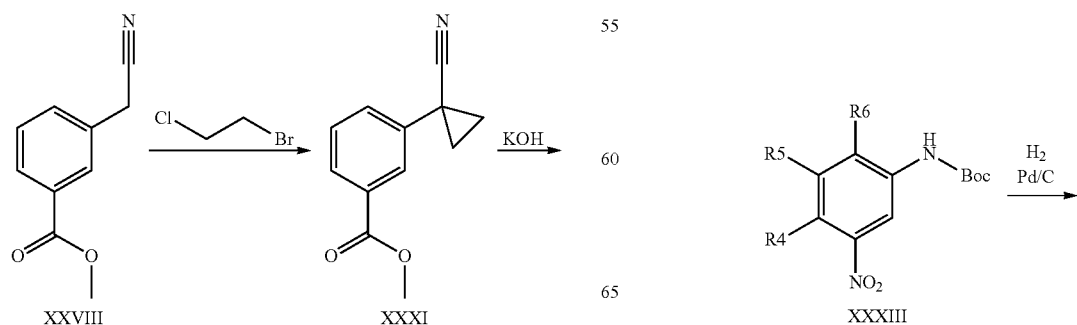

-continued

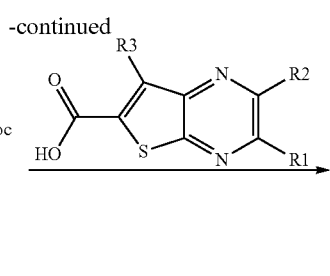

XXXIV

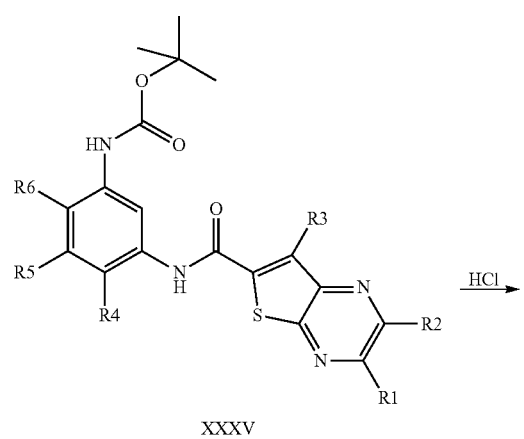

XXXV

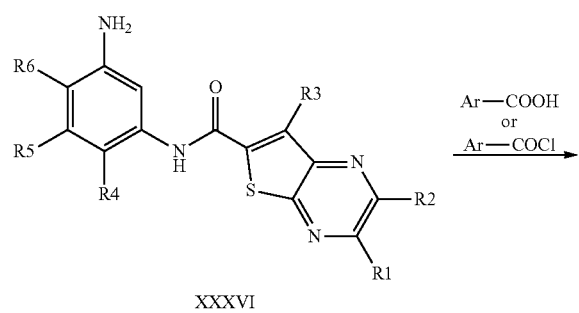

XXXVI

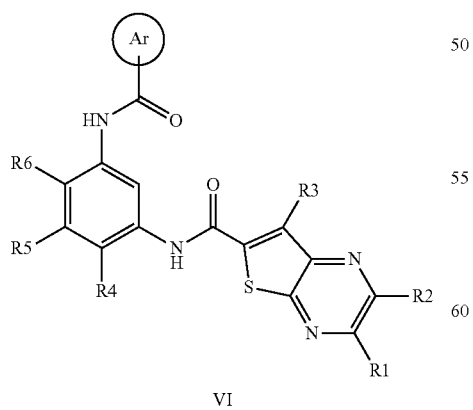

VI

The amine functionality of nitroaniline is protected with a protection group, such as a Boc-group. The nitro group can be reduced with reducing agents such as H₂ on Pd/C. The amine formed (XXXIV) can react with (substituted) thieno pyrazine carboxylic acid derivatives to yield XXXV. After deprotection, amine XXXVI can react with (substituted) benzoic acid and substituted heteroaromates with carboxylic acid groups or carboxylic chloride groups to afford VI.

Scheme H

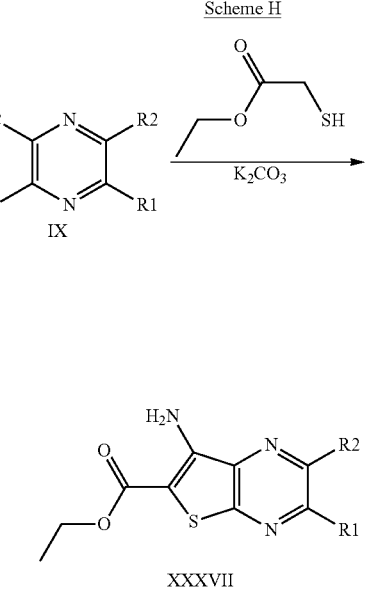

IX

XXXVII

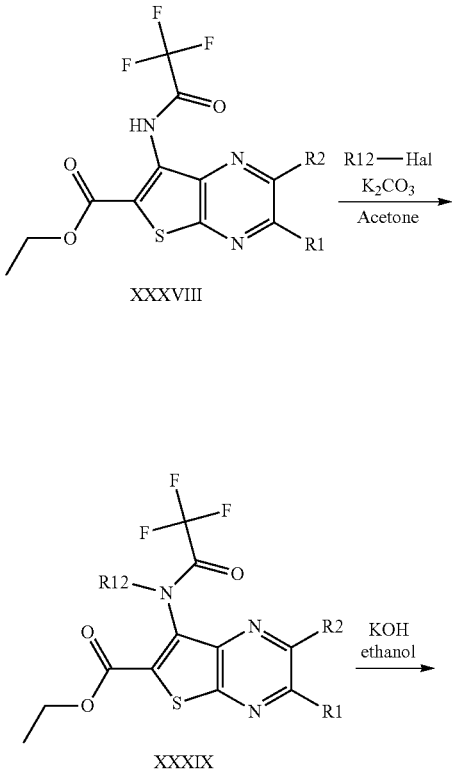

XXXVIII

XXXIX

-continued

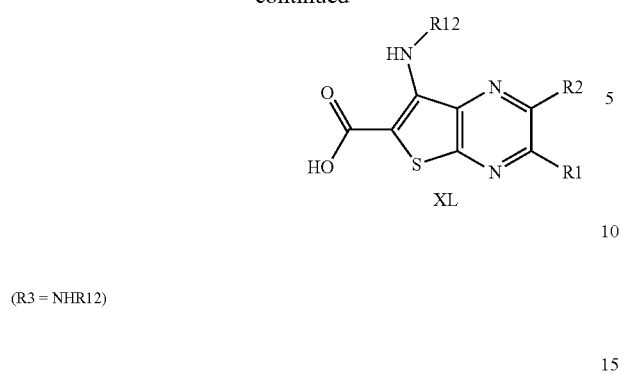

(R3 = NHR12)

-continued

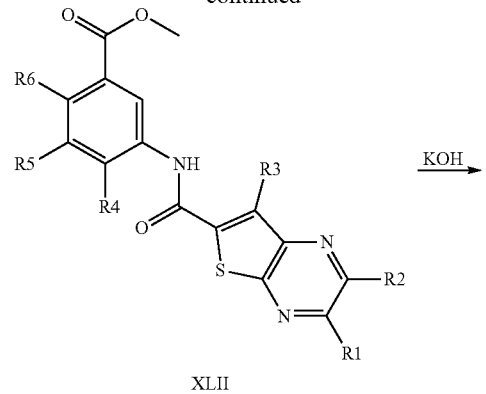

Conversion of bromo or chloro-nitril pyrazine derivative IX in (substituted) thienopyrazine XXXVII can be accomplished by the addition of ethyl mercapto acetate and heating to 50° C. Addition of trifluoroacetic anhydride at room temperature afforded XXXVIII, and subsequent alkylation with alkylhalides such as methyliodide will result in the formation of compounds XXXIX. After deprotection and hydrolysis, by the addition of a base such as potassium hydroxide and heating at 60° C., carboxylic acid XL (in which R3=NHR12) can be obtained. Carboxylic acid derivatives XL can react with amines IV to afford amide derivatives VI as is described in scheme A.

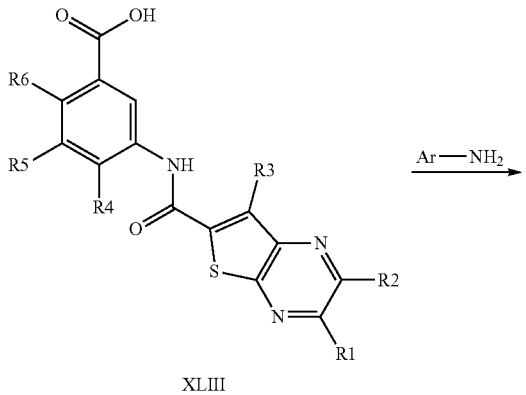

Scheme I

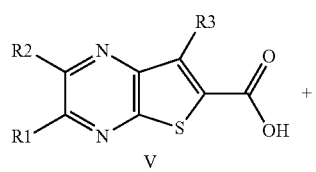

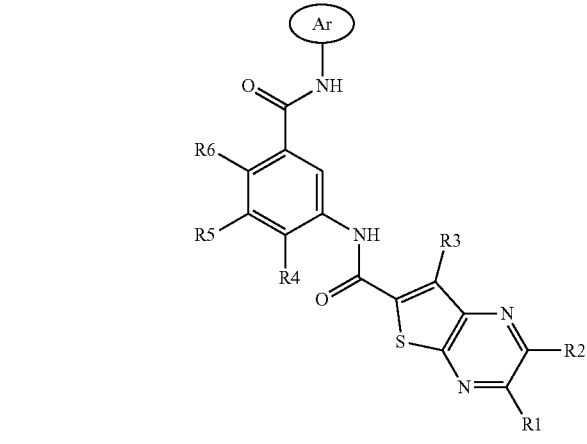

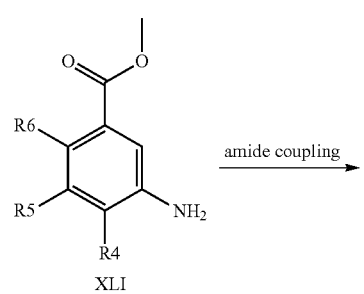

Carboxylic acid V can react with amine XLI in the presence of an amide coupling agent such as HATU or TBTU in the presence of a base such as DIPEA. XLII can be hydrolysed with a base such as potassium hydroxide, and the carboxylic acid formed can be subsequently react with (substituted) anilines and heteroaromatic amines to afford amide derivatives XLIV.

Scheme J

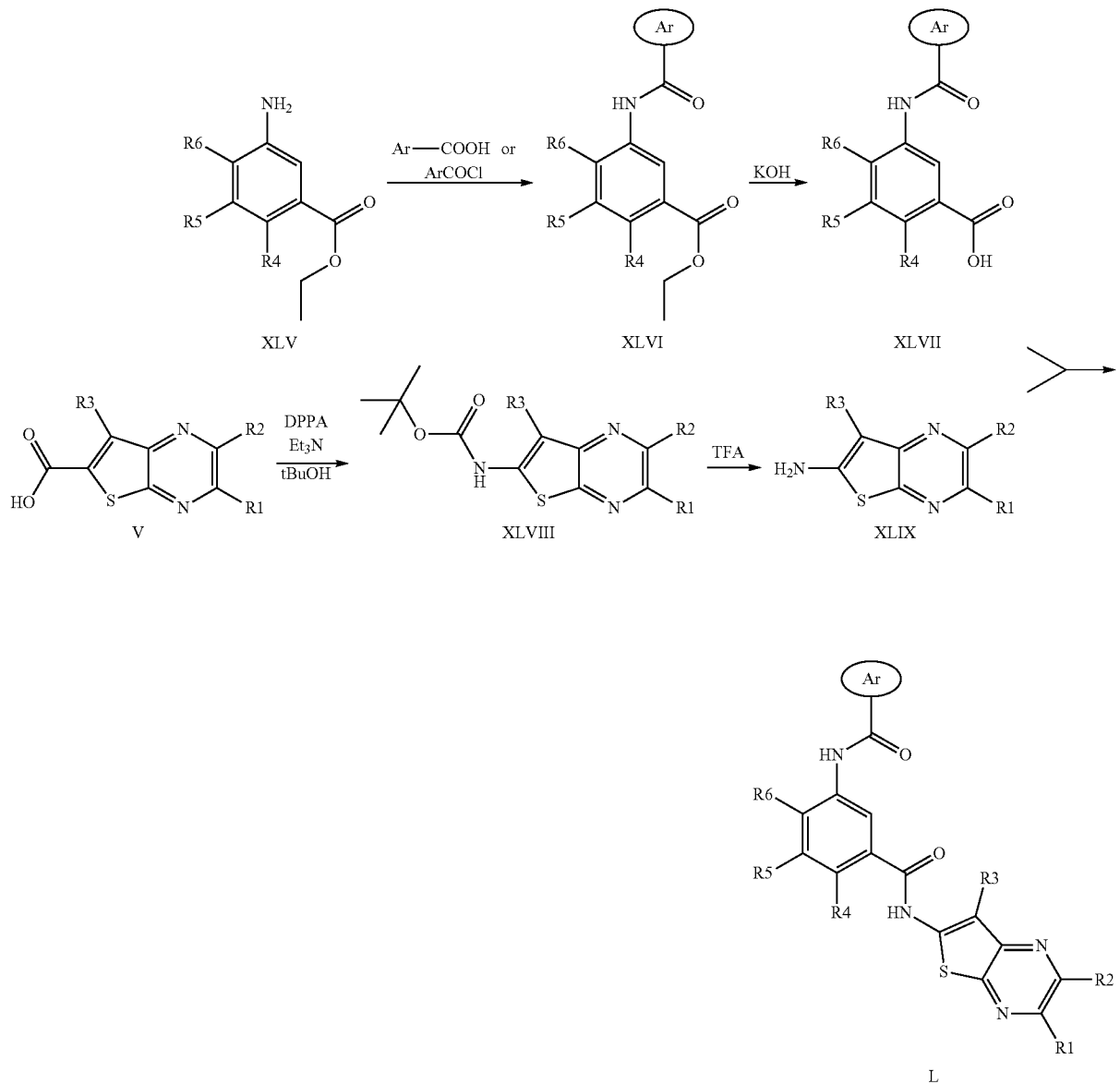

Reaction of amine derivatives XLV with (substituted) benzoic acids or heteroaromatic carboxylic acids in the presence of amide coupling agents such as TBTU or HATU and a base such as DIPEA affords amide derivatives XLVI. By hydrolysis of the ester, carboxylic acids XLVII can be obtained. The carboxylic acid group of thienopyrazines V can be transformed in an amine-functionality by a Curtius rearrangement in the presence of DPPA, a base such as triethylamine in tert-butanol. Subsequent deprotection with TFA will afford amine derivative XLIX. In a final step amides L can be obtained by a reaction of amine XLIX and carboxylic acid XLVII in the presence of amide coupling agents such as TBTU or HATU and a base such as DIPEA.

The compounds of the invention may form hydrates or solvates. It is known to those of skill in the art that charged compounds form hydrated species when lyophilized with water, or form solvated species when concentrated in a solution with an appropriate organic solvent. The compounds of this invention include the prodrugs, hydrates or solvates of the compounds listed.

A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g. by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contain both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula (I) may be atropisomers (e.g. substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The thieno(2,3b)pyrazine compounds of the invention were found to inhibit the B-Raf. Methods to determine Raf kinase inhibition as well as in vitro and in vivo assays to determine biological activity are well known. In one possible assay Raf kinase is incubated with the compound to be tested and inhibition of phosphorylation of one of the proteins in the kinase pathway is measured.

In another assay the B-Raf kinase activity can be determined by using an IMAP assay (Immobilized Metal Assay for Phosphochemicals-based coupled assay). IMAP is a homogeneous fluorescence polarization (FP) assay based on affinity capture of phosphorylated peptide substrates. IMAP uses fluorescein-labeled peptide substrates that, upon phosphorylation by a protein kinase, bind to so called IMAP nanoparticles, which are derivatized with trivalent metal complexes. Such binding causes a change in the rate of the molecular motion of the peptide, and results in an increase in the FP value observed for the fluorescein label attached to the substrate peptide. In such an assay, B-Raf phosphorylates unactive MEK1. The phosphorylated MEK1 is capable of phosphorylating ERK2, which subsequently phosphorylates the fluorescein-labeled peptide substrate.

The B-Raf activity can also be determined in a B-Raf mutated melanoma cell line, such as the A375 cell line. Inhibition of phosphorylation of ERK1/2 can be measured using a Fast Activated Cell-based ELISA (FACE) from Active Motif (Carlsbad, U.S.A., CA). E.g. A375 cells, which are cells containing a mutant form of B-Raf (V600E) and thus contain high levels of phosphorylated ERK, can be incubated with Raf inhibitors. Then cells can be incubated with anti-phospho-ERK antibody and subsequently with horse radish peroxidase (HRP)-labeled secondary antibody. Finally, chemiluminescence reagents can be added, which react with HRP, to give a luminescence signal.

The present invention also relates to a pharmaceutical composition comprising a thieno(2,3b)pyrazine derivative compounds or pharmaceutically acceptable salts thereof having the general formula I in admixture with a pharmaceutically acceptable auxiliary and optionally other therapeutic agents. The auxiliaries must be "acceptable" in the sense of being compatible with the other ingredients of the composition and not deleterious to the recipients thereof.

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: The Science and Practice of Pharmacy (20th Edition, Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general, parenteral administration requires lower dosages than other methods of administration which are more dependent upon absorption. However, a suitable dosage for humans may be 1-1000 mg per kg body weight, preferably between 10-300 mg per kg body weight. The desired dose may be presented as one dose or as multiple subdoses administered at appropriate intervals throughout the day. The actual dosage employed may be varied depending on the requirements of the patient and the severity of the condition being treated by judgement of the skilled clinician The compounds according to the invention can be used in therapy. They can be used for the treatment of cancer.

A further aspect of the invention resides in the use of thieno(2,3b)pyrazine compounds having the general formula I for the manufacture of a medicament to be used for the treatment of patients in need thereof or patients in which B-Raf activating mutations have been observed. In particular the compounds can be used to treat proliferative disorders. More in particular the compounds can be used for the treatment of melanomas, papillary thyroid tumors, ovarian, colon and lung cancers. Thus, patients in need thereof can be administered with suitable amounts of the compounds according to the invention.

In yet another aspect the invention resides in the use of thieno(2,3b)pyrazine compounds having the general formula I for the manufacture of a medicament to be used for the treatment of cancer.

The B-Raf inhibitory treatment defined hereinabove may be applied as a sole therapy or may involve, in addition to the compound of the invention, conventional surgery or radiotherapy or chemotherapy.

Methods for co-administration or treatment with a second therapeutic agent are well known in the art, see, e.g., Hardman, et al. (eds.), 2001, *Goodman and Gilman's The Pharmacological Basis of Therapeutics*, 10$^{th}$ ed., McGraw-Hill, New York, N.Y.; Poole and Peterson (eds.), 2001, *Pharmacotherapeutics for Advanced Practice: A Practical Approach*, Lippincott, Williams & Wilkins, Phila., PA; Chabner and Longo (eds.), 2001, *Cancer Chemotherapy and Biotherapy*, Lippincott, Williams & Wilkins, Phila., PA.

The pharmaceutical composition of the invention may also contain other agent, including but not limited to a cytotoxic, chemotherapeutic, cytostatic, anti-angiogenic or antimetabolite agent, a tumor targeted agent, an immune stimulating or immune modulating agent or an antibody conjugated to a cytotoxic, cytostatic, or otherwise toxic agent.

The invention is illustrated by the following examples:

EXAMPLES

Example 1

Synthesis of 7-amino-N-(5-(3-(2-cyanopropan-2-yl) benzamido)-2-methylphenyl)thieno[2,3-b]pyrazine-6-carboxamide (9)

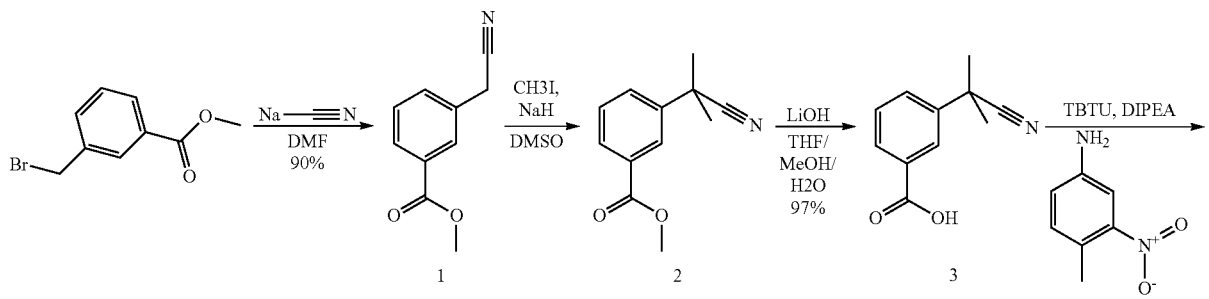

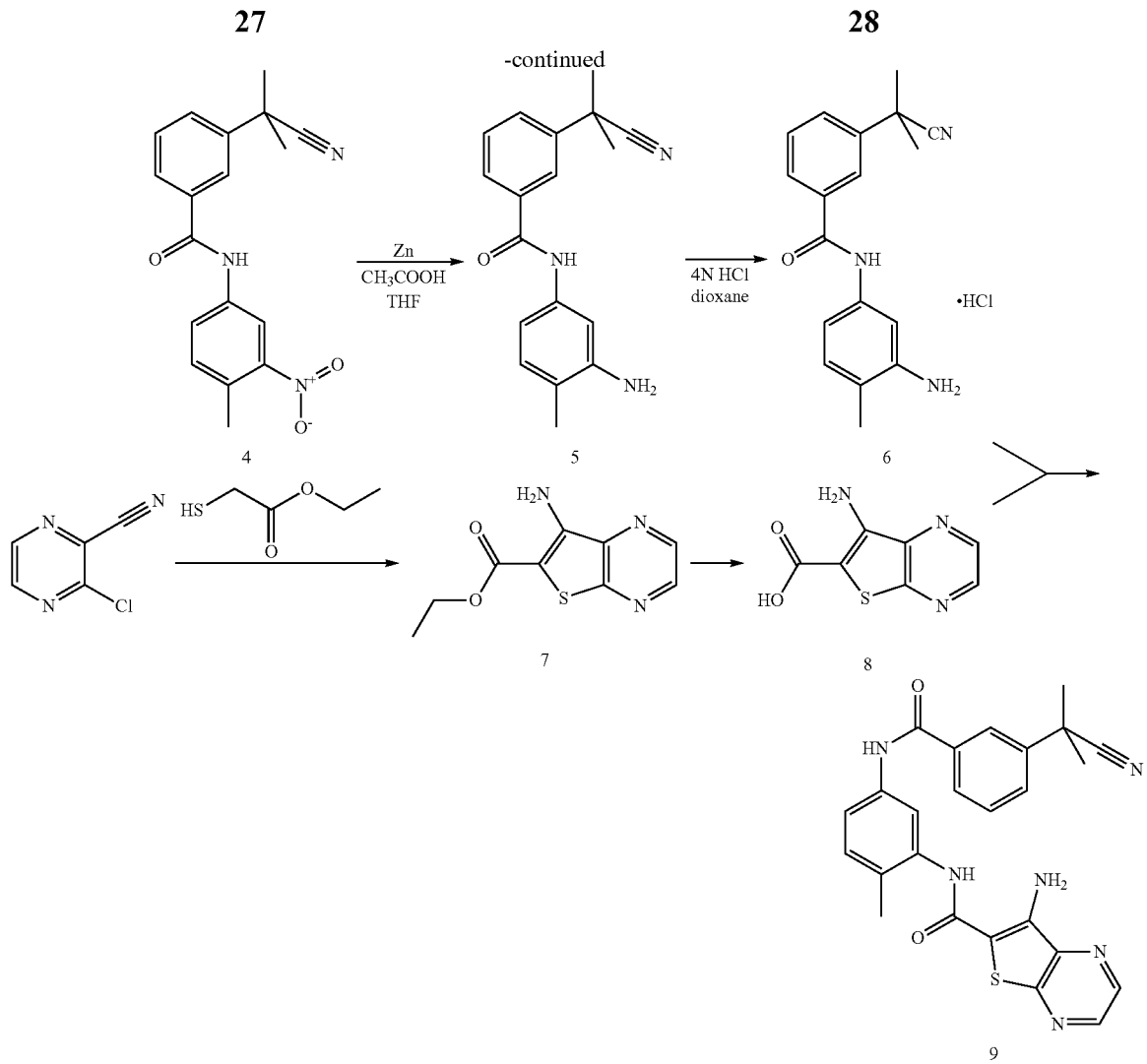

Step 1: synthesis of methyl 3-(cyanomethyl)benzoate (1)

To a solution of 3-(bromomethyl)benzoic acid methyl ester (25 g, 109 mmol) in DMF (250 mL) was added NaCN (5.4 g, 109 mmol). The reaction mixture was stirred overnight at rt. The mixture was poured into water (1.5 L), followed by the extraction with TBME (2×500 mL). The combined organic layers were washed with water, brine, dried (Na$_2$SO$_4$), filtered and evaporated under reduced pressure to yield methyl 3-(cyanomethyl)benzoate 1 (17 g, 89%). $^1$H-NMR (400 MHz, CDCl$_3$) 3.82 (s, 2H), 3.94 (s, 3H), 7.48 (m, 1H), 7.57 (m, 1H), 8.03 (m, 2H).

Step 2: synthesis of methyl 3-(2-cyanopropan-2-yl)benzoate (2)

A solution of 3-cyanomethyl-benzoic acid methyl ester 1 (53 g, 302 mmol) in DMSO (800 mL) was treated with sodium hydride (60%, 36.2 g, 907 mmol). To this deep-red suspension was then added methyl iodide (56.5 mL, 907 mmol) drop wise at 0° C. (under vigorous stirring). This resulting mixture was stirred overnight at 25° C. resulting in an orange solution. The reaction mixture was quenched with water (1000 mL) and extracted with EtOAc. The combined organic layers were dried with Na$_2$SO$_4$, filtrated and concentrated in vacuo to give crude methyl 3-(2-cyanopropan-2-yl) benzoate 2 (72 g, 100%). $^1$H-NMR (400 MHz, CDCl$_3$) 1.77 (s, 6H), 3.94 (s, 3H), 7.49 (t, J=7.5 Hz, 1H), 7.73 (m, 1H), 8.01 (m, 1H), 8.13 (m, 1H).

Step 3: synthesis of 3-(2-cyanopropan-2-yl)benzoic acid (3)

A solution of methyl 3-(2-cyanopropan-2-yl)benzoate 2 (72 g, 5.9 mmol) in THF (900 mL), MeOH (300 mL) and water 300 (mL) was treated with lithium hydroxide (47.6 g, 1.13 mol). The mixture was stirred overnight at rt. Concentrated to ±300 mL in vacuo and the resulting solution was acidified with 1N HCl solution. The resulting white precipitate was collected, washed with water and dried. Purification by column chromatography (5% methanol in CH$_2$Cl$_2$) gave pure 3-(2-cyanopropan-2-yl)benzoic acid 3 (20.7 g, 31%). $^1$H-NMR (400 MHz, CDCl$_3$) 1.78 (s, 6H), (t, J=7.5 Hz, 1H), 7.80 (m, 1H), 8.09 (m, 1H), 8.20 (m, 1H).

Step 4: synthesis of 3-(2-cyanopropan-2-yl)-N-(4-methyl-3-nitrophenyl)benzamide (4)

3-(2-cyanopropan-2-yl)benzoic acid 3 (25 g, 132 mmol), TBTU (63 g, 98 mmol), DIPEA (396 mmol, 65.4 mL) and 4-methyl-3-nitroaniline (20.1 g, 132 mmol) were dissolved in DMF (500 mL) and stirred for 72 h. The reaction mixture was poured into citric acid solution (3%) and extracted twice with EtOAc. The combined organic layers were washed with water (5×), brine (2×), dried, and evaporated. Purification by chromatography ($CH_2Cl_2$) gave 3-(2-cyanopropan-2-yl)-N-(4-methyl-3-nitrophenyl)benzamide 4 (27 g, 63%). $^1$H-NMR (400 MHz, $CDCl_3$) 1.78 (s, 6H), 2.60 (s, 3H), (d, J=8.5 Hz, 1H), 7.55 (t, J=7.6 Hz, 1H), 7.73 (m, 1H), 7.80 (m, 1H), 7.90 (m, 1H), 7.99 (m, 1H), 8.06 (br s, 1H), 8.28 (m, 1H).

Step 5: synthesis of N-(3-amino-4-methylphenyl)-3-(2-cyanopropan-2-yl)benzamide (5)

To a solution of 3-(2-cyanopropan-2-yl)-N-(4-methyl-3-nitrophenyl)benzamide 4 (27 g, 84 mmol) and $CH_3COOH$ (72 mL, 1.3 mol) in THF (300 mL) at rt was added zinc (1.68 mol, 109 g). The temperature was maintained at 20° C. by cooling with an ice bath. The reaction was stirred at 20° C. for 1 hour. After dilution with ether the organic layer was extracted with 1N NaOH solution, water, brine, dried and evaporated to give crude N-(3-amino-4-methylphenyl)-3-(2-cyanopropan-2-yl)benzamide 5 (24.7 g, 100%). $^1$H-NMR (400 MHz, $CDCl_3$) 1.77 (s, 6H), 2.15 (s, 3H), 3.68 (br s, 2H). 6.77 (dd, J=7.1 and 1.9 Hz, 1H), 7.02 (d, J=8.0 Hz, 1H), 7.27 (br s, 1H), 7.50 (t, J=8, 1H), 7.69 (m, 1H), 7.75 (m, 2H), 7.96 (m, 1H).

Step 6: synthesis of N-(3-amino-4-methylphenyl)-3-(2-cyanopropan-2-yl)benzamide hydrochloride (6)

To a solution of N-(3-amino-4-methylphenyl)-3-(2-cyanopropan-2-yl)benzamide 5 (18 g, 61 mmol) in dioxane was added 4N HCl in dioxane (1.1 eq) and stirred at 60° C. for 1 h. After cooling the precipitate was collected to give N-(3-amino-4-methylphenyl)-3-(2-cyanopropan-2-yl)benzamide hydrochloride 6 (16.7 g, 83%).

Step 7: synthesis of Ethyl 7-aminothieno[2,3-b]pyrazine-6-carboxylate (7)

A mixture of 3-chloropyrazine-2-carbonitrile (17.9 g, 128 mmol), sodium carbonate (17.7 g, 167 mmol) and ethyl-2-mercaptoacetate (18.4 mL, 167 mmol) in ethanol (120 mL) was heated to reflux for 4.5 h. Quenched with water (1.5 L) and stirred for 30 min. The resulting precipitate was collected and washed with water. The residue was dissolved in diethyl ether and a black precipitate was filtrated off. Ether was evaporated to give pure compound ethyl 7-aminothieno[2,3-b]pyrazine-6-carboxylate 7 (19.6 g, 68.5%). $^1$H-NMR (400 MHz, $CDCl_3$) 1.42 (t, J=7.2 Hz, 3H), 4.40 (q, J=7.2 Hz, 2H), 6.19 (br s, 1H), 8.58 (d, J=2.2 Hz, 1H), 8.63 (d, J=2.2 Hz, 1H).

Step 8: synthesis of 7-aminothieno[2,3-b]pyrazine-6-carboxylic acid (8)

A solution of ethyl 7-aminothieno[2,3-b]pyrazine-6-carboxylate 7 (10 g, 44.8 mmol) and potassium hydroxide (5.0 g, 90 mmol) in THF (50 mL), ethanol (50 mL) and water (20 mL) was stirred at 70° C. for 2 h. Quenched in a cold solution of 2N HCl, and the resulting precipitate was collected to give crude 7-aminothieno[2,3-b]pyrazine-6-carboxylic acid 8 (8.59 g, 98%). $^1$H-NMR (400 MHz, DMSO-d6) 7.03 (br s, 2H), 8.77 (s, 2H), 12.8 (br s, 1H).

Step 9: Synthesis of 7-amino-N-(5-(3-(2-cyanopropan-2-yl)benzamido)-2-methylphenyl)thieno[2,3-b]pyrazine-6-carboxamide (9)

A solution of 7-aminothieno[2,3-b]pyrazine-6-carboxylic acid (8) (1.6 g, 8.20 mmol), HATU (3.43 g, 9.02 mmol) and DIPEA (4.06 mL, 24.59 mmol) in DMF (20 mL) was stirred at rt for 20 min. N-(3-amino-4-methylphenyl)-3-(2-cyanopropan-2-yl)benzamide hydrochloride 6 (2.70 g, 8.20 mmol) was added and stirred overnight at 80° C. Quenched in cold citric acid solution and the resulting precipitate was collected and dried to give crude compound 9 (3.55 g). Triturating with acetonitrile, stirred in water at 90° C. for 30 min, filtrated and dried to yield the title compound 7-amino-N-(5-(3-(2-cyanopropan-2-yl)benzamido)-2-methylphenyl)thieno[2,3-b]pyrazine-6-carboxamide 9 (2.12 g, 55.0%). $^1$H-NMR (400 MHz, DMSO-d6) 1.77 (s, 6H), 2.23 (s, 3H), 7.06 (br s, 2H), 7.27 (d, J=8.6 Hz, 1H), 7.60 (t, J=7.8 Hz, 2H), 7.75 (m, 1H), 7.82 (br s, 1H), 7.95 (d, J=7.8 Hz, 1H), 8.05 (m, 1H), 8.78 (q, J=2.7 and 2.3 Hz, 2H), 9.47 (br s, 1H), 10.32 (br s, 1H). (m/z)=471 (M+H)$^+$.

Example 2

Synthesis of N-(5-(3-(2-cyanopropan-2-yl)benzamido)-2-methylphenyl)-7-(methylamino)thieno[2,3-b]pyrazine-6-carboxamide (13)

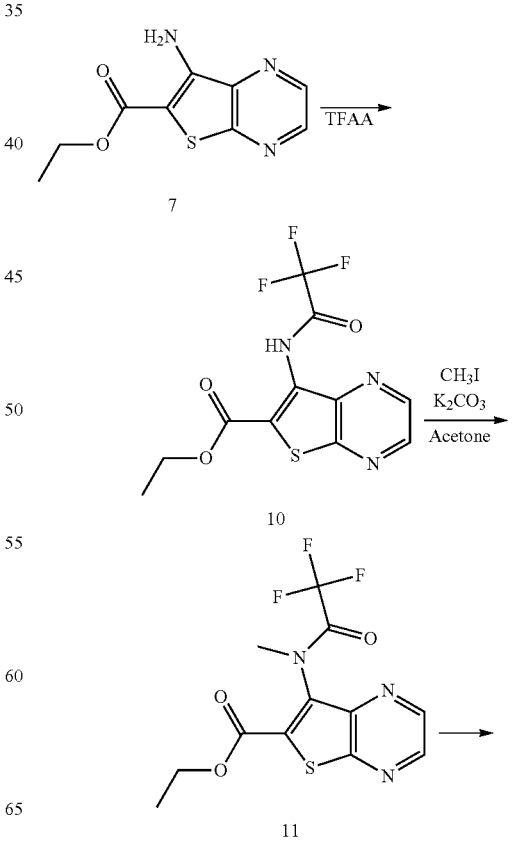

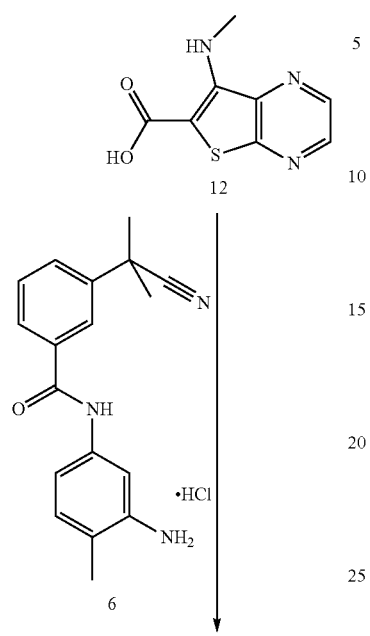

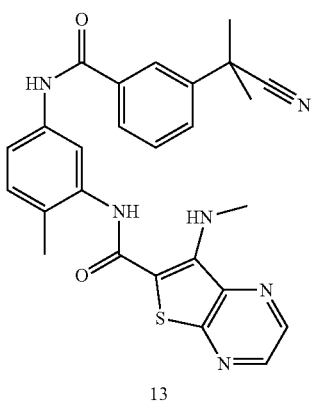 [SMILES: CNc1c(C(=O)Nc2cc(NC(=O)c3cccc(C(C)(C)C#N)c3)ccc2C)sc2nccnc12]

Step 1: synthesis of ethyl 7-(2,2,2-trifluoroacetamido)thieno[2,3-b]pyrazine-6-carboxylate (10)

To a solution of ethyl 7-aminothieno[2,3-b]pyrazine-6-carboxylate 7 (7 g, 31.4 mmol) in THF (40 mL) was added trifluoroacetic anhydride (6.97 mL, 50.2 mmol). The reaction was stirred at rt for 30 min. Concentrated by evaporation, quenched in ice/water and the resulting precipitate was collected. Purification by chromatography (0-10% EtOAc in $CH_2Cl_2$) gave pure ethyl 7-(2,2,2-trifluoroacetamido)thieno[2,3-b]pyrazine-6-carboxylate 10 (9.22 g, 92%). (m/z)=320 $(M+H)^+$.

Step 2: synthesis of ethyl 7-(2,2,2-trifluoro-N-methylacetamido)thieno[2,3-b]pyrazine-6-carboxylate (11)

To a solution of ethyl 7-(2,2,2-trifluoroacetamido)thieno[2,3-b]pyrazine-6-carboxylate 10 (9.22 g, 28.9 mmol) and potassium carbonate (7.98 g, 57.8 mmol) in acetone (140 mL) was added iodomethane (3.60 mL, 57.8 mmol). The reaction was stirred at 50° C. for 1 h. $NH_4Cl$ solution(aq) was added and extracted with EtOAc. Organic layer was washed with brine, dried and evaporated to give crude ethyl 7-(2,2,2-trifluoro-N-methylacetamido)thieno[2,3-b]pyrazine-6-carboxylate 11 (9.1 g, 95%). (m/z)=334 $(M+H)^+$.

Step 3: synthesis of 7-(methylamino)thieno[2,3-b]pyrazine-6-carboxylic acid (12)

A solution of 7-(2,2,2-trifluoro-N-methylacetamido)thieno[2,3-b]pyrazine-6-carboxylate 11 (9.1 g, 27.3 mmol) and KOH (3 eq) in THF (40 mL), ethanol (40 mL) and water (20 mL) was stirred overnight at 60° C. Concentrated by evaporation (±10 mL), ice cold citric acid solution was added (200 mL) and stirred for 10 min. The resulting precipitate was collected, washed with water and dried to give compound 7-(methylamino)thieno[2,3-b]pyrazine-6-carboxylic acid 12 (5.6 g, 98%). $^1$H-NMR (400 MHz, DMSO-d6) 3.49 (s, 3H), 7.59 (br s, 2H) 8.72 (d, J=2.3 Hz, 1H), 8.74 (d, J=2.3 Hz, 1H) 12.95 (br s, 1H). (m/z)=210 $(M+H)^+$.

Step 4: synthesis of N-(5-(3-(2-cyanopropan-2-yl)benzamido)-2-methylphenyl)-7-(methylamino)thieno[2,3-b]pyrazine-6-carboxamide (13)

A solution of 7-(methylamino)thieno[2,3-b]pyrazine-6-carboxylic acid 12 (1.6 g, 7.65 mmol), HATU (3.20 g, 8.41 mmol) and DIPEA (3.79 mL, 22.94 mmol) in DMF (20 mL) was stirred at rt for 30 min. N-(3-amino-4-methylphenyl)-3-(2-cyanopropan-2-yl)benzamide hydrochloride 6 (2.52 g, 7.65 mmol) was added and stirred overnight at 75° C. Quenched in ice/water and the resulting precipitate was collected. Purification by chromatography (10-20% EtOAc in $CH_2Cl_2$, co-evaporate with acetonitrile (2×), stirred in water at 70° C. for 1 h and filtrated to give the title compound N-(5-(3-(2-cyanopropan-2-yl)benzamido)-2-methylphenyl)-7-(methylamino)thieno[2,3-b]pyrazine-6-carboxamide 13 (2.06 g, 55.6%). $^1$H-NMR (400 MHz, DMSO-d6) 1.76 (s, 6H), 2.22 (s, 3H), 3.41 (d, J=5.5 Hz, 3H), 7.26 (d, J=8.6 Hz, 1H), 7.60 (t, J=7.8 Hz, 2H), 7.75 (d, J=7.8 Hz, 1H), 7.82 (d, J=1.9 Hz), 1H), 7.94 (d, J=7.8 Hz, 2H), 8.05 (m, 1H), 8.73 (d, J=2.3 Hz, 1H), 8.77 (d, J=2.3 Hz, 1H), 9.55 (br s, 1H), 10.31 (br s, 1H). (m/z)=485 $(M+H)^+$.

Example 3

Synthesis of 7-amino-2-bromo-N-(5-(3-(2-cyanopropan-2-yl)benzamido)-2-methylphenyl)thieno[2,3-b]pyrazine-6-carboxamide (17)

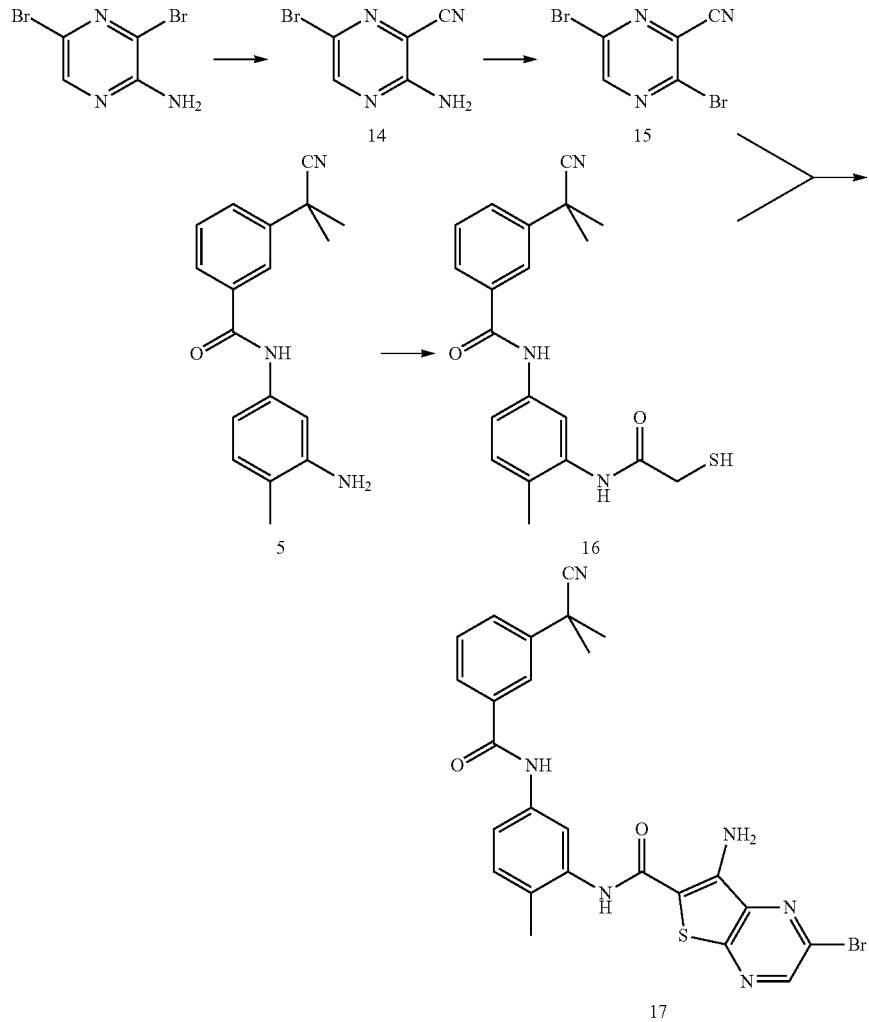

Step 1: synthesis of 3-amino-6-bromopyrazine-2-carbonitrile (14)

A solution of copper(i) cyanide (1.20 g, 13.42 mmol) and sodium cyanide (0.658 g, 13.42 mmol) in DMF (10 mL) was heated to 125° C. 2-amino-3,5-dibromo pyrazine (2.61 g, 10.32 mmol) was added in portions. The reaction was stirred at 125° C., and after 5 h quenched in ice cold NaHCO$_3$ solution. The black precipitate was filtrated off and the filtrate was extracted (3×) with EtOAc. The organic layer was washed with brine, dried and evaporated. Purification by chromatography (CH$_2$Cl$_2$) gave pure 3-amino-6-bromopyrazine-2-carbonitrile 14 (1.38 g, 67.2%). $^1$H-NMR (400 MHz, CDCl$_3$) 5.29 (br s, 2H), 8.30 (s, 1H). (m/z)=199 and 201 (M+H)$^+$.

Step 2: synthesis of 3,6-dibromopyrazine-2-carbonitrile (15)

To a solution of copper(ii) bromide (1.432 g, 6.41 mmol) and tert-butylnitrite (0.769 mL, 6.41 mmol) in acetonitrile (40 mL) was added 3-amino-6-bromopyrazine-2-carbonitrile 14 (1.16 g, 5.83 mmol) in portions (in 2 h). The reaction was stirred for 2 h at 50° C. Quenched with 2N HCl solution and the resulting precipitate was collected. Purification by chromatography (CH$_2$Cl$_2$) gave pure 3,6-dibromopyrazine-2-carbonitrile 15 (820 mg, 53.5%). $^1$H-NMR (400 MHz, CDCl$_3$) 8.66 (s, 1H). (m/z)=261, 263 and 265 (M+H)$^+$.

Step 3: synthesis of 3-(2-cyanopropan-2-yl)-N-(3-(2-mercaptoacetamido)-4-methylphenyl)benzamide (16)

A solution of N-(3-amino-4-methylphenyl)-3-(2-cyanopropan-2-yl)benzamide 5 (500 mg, 1.704 mmol) in mercaptoacetic acid (3 mL, 43.2 mmol) was stirred at 100° C. for 2 h. Quenched with water and extracted with EtOAc. Organic layer was washed with NaHCO$_3$ solution, brine, dried and evaporated. Purification by chromatography (0-4% methanol in CH$_2$Cl$_2$) gave pure 3-(2-cyanopropan-2-yl)-N-(3-(2-mercaptoacetamido)-4-methylphenyl)benzamide 16 (500 mg, 80%). $^1$H-NMR (400 MHz, CDCl$_3$) 1.78 (s, 6H), 2.31 (s, 3H), 3.45 (d, J=9.4 Hz, 2H), 7.21 (d, J=8.2 Hz, 1H), 7.52 (t, J=8.2 Hz, 1H), 7.70-7.79 (m, 3H), 7.92-8.08 (m, 3H), 8.67 (br s, 1H).

Step 4: synthesis of 7-amino-2-bromo-N-(5-(3-(2-cyanopropan-2-yl)benzamido)-2-methylphenyl)thieno[2,3-b]pyrazine-6-carboxamide (17)

To a solution of 3,6-dibromopyrazine-2-carbonitrile 15 (286 mg, 1.089 mmol) and 3-(2-cyanopropan-2-yl)-N-(3-(2-mercaptoacetamido)-4-methylphenyl)benzamide 16 (400 mg, 1.089 mmol) in ethanol (5 mL) was added potassium carbonate (211 mg, 1.524 mmol). The reaction was stirred 1 h at rt and 2 h at 50° C. Quenched in cooled 1N HCl solution (aq), the resulting precipitate was collected and dried to give crude compound 17 (588 mg). Purification by chromatography (0-10% EtOAc in CH$_2$Cl$_2$) gave pure 7-amino-2-bromo-N-(5-(3-(2-cyanopropan-2-yl)benzamido)-2-methylphenyl)thieno[2,3-b]pyrazine-6-carboxamide 17 (463 mg, 77%). $^1$H-NMR (400 MHz, DMSO-d6) 1.75 (s, 6H), 2.21 (s, 3H), 7.09 (br s, 2H), 7.27 (d, J=8.6 Hz, 1H), 7.60 (t, J=7.8 Hz, 2H), 7.75 (d, J=7.8 Hz, 1H), 7.81 (br s, 1H), 7.95 (d, J=7.0, 1H), 8.05 (s, 1H), 8.93 (br s, 1H), 9.58 (br s, 1H), 10.32 (br s, 1H). (m/z)=549 and 551 (M+H)$^+$.

Example 4

Synthesis of 7-amino-N-(5-(3-(2-cyanopropan-2-yl)benzamido)-2-methylphenyl)-2-(dimethylamino)thieno[2,3-b]pyrazine-6-carboxamide (18a) (R=dimethylamine)

General Procedure I

A solution of 7-amino-2-bromo-N-(5-(3-(2-cyanopropan-2-yl)benzamido)-2-methylphenyl)thieno[2,3-b]pyrazine-6-carboxamide 17 (1 eq), amine, and DIPEA or triethylamine, in butan-2-ol was stirred at 150° C. in microwave. Evaporated to dryness and purified by chromatography to give the title compounds 18a-i

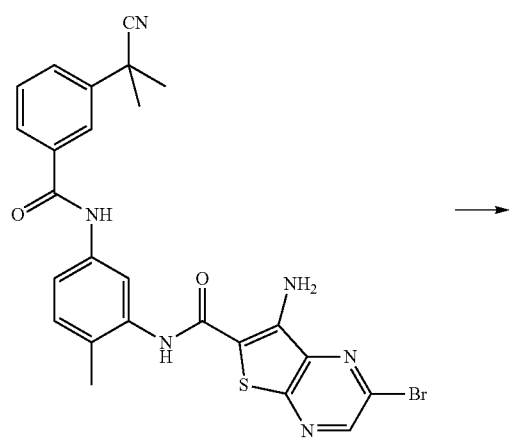

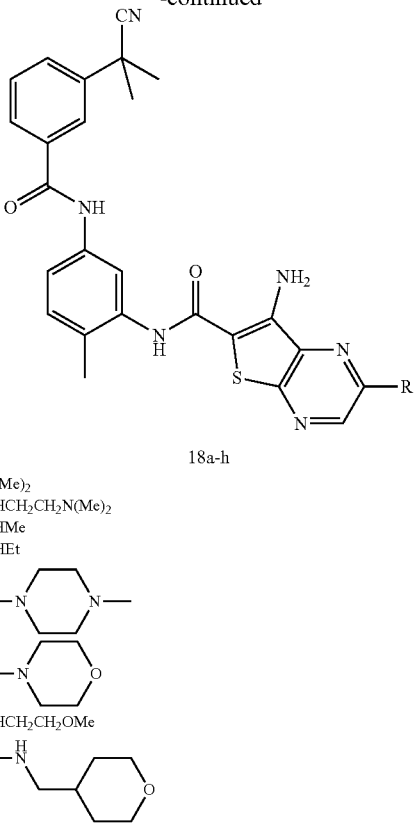

18a: R = N(Me)$_2$
18b: R = NHCH$_2$CH$_2$N(Me)$_2$
18c: R = NHMe
18d: R = NHEt

18e: R = —N⌒N—

18f: R = —N⌒O

18g: R = NHCH$_2$CH$_2$OMe

18h: R = —NH-CH$_2$-(tetrahydropyran-4-yl)

Synthesis of 7-amino-N-(5-(3-(2-cyanopropan-2-yl)benzamido)-2-methylphenyl)-2-(dimethylamino)thieno[2,3-b]pyrazine-6-carboxamide (18a) (R=dimethylamine)

Preparation as described in general procedure I by using dimethylamine (2N/THF), DIPEA (15 eq) in butan-2-ol (2 mL) 5 h. Purification by chromatography (0-20% EtOAc in CH$_2$Cl$_2$) gave the title compound 7-amino-N-(5-(3-(2-cyanopropan-2-yl)benzamido)-2-methylphenyl)-2-(dimethylamino)thieno[2,3-b]pyrazine-6-carboxamide 18a (30 mg, 80%). $^1$H-NMR (400 MHz, DMSO-d6) 1.75 (s, 6H), 2.22 (s, 3H), 3.19 (s, 6H), 6.67 (br s, 2H), 7.25 (d, J=8.2 Hz, 1H), 7.60 (m, 2H), 7.75 (m, 1H), 7.82 (d, J=1.9 Hz, 1H), 7.95 (d, J=7.8 Hz, 1H), 8.05 (t, J=1.9 Hz, 1H), 8.37 (s, 1H), 9.21 (s, 1H), 10.31 (s, 1H). (m/z)=514 (M+H)$^+$.

Example 5

Synthesis of 7-amino-N-(5-(3-(2-cyanopropan-2-yl)benzamido)-2-methylphenyl)-2-(2-(dimethylamino)ethylamino)thieno[2,3-b]pyrazine-6-carboxamide (18b) (R=1-amino-2-dimethylaminoethane)

Preparation analogous to general procedure I by using 1-amino-2-dimethylaminoethane in Butan-2-ol (1 mL), DIPEA (15 eq) 5 h. Purification by chromatography (10-40% MeOH in CH$_2$Cl$_2$) gave the title compound 7-amino-N-(5-(3-(2-cyanopropan-2-yl)benzamido)-2-methylphenyl)-2-(2-(dimethylamino)ethylamino) thieno[2,3-b]pyrazine-6-carboxamide 18b (12 mg, 74%). $^1$H-NMR (400 MHz, DMSO-d6) 1.76 (s, 6H), 2.21 (s, 9H), 2.48 (m, 2H), 3.49 (q, J=6.2 and 5.8 Hz, 2H), 6.56 (s, 2H), 7.24 (d, J=8.6 Hz, 1H), 7.31 (t, J=5.5, 1H), 7.57-7.63 (m, 2H), 7.75 (d, J=7.8 Hz, 1H), 7.82 (d, J=1.9 Hz, 1H), 7.94 (d, J=7.8 Hz, 1H), 8.05 (m, 1H), 8.15 (s, 1H), 9.18 (s, 1H), 10.31 (s, 1H). (m/z)=557 (M+H)$^+$.

Example 6

Synthesis of 7-amino-N-(5-(3-(2-cyanopropan-2-yl)benzamido)-2-methylphenyl)-2-(methylamino)thieno[2,3-b]pyrazine-6-carboxamide (18c) (R=methylamine)

Preparation analogous to general procedure I by using methylamine (33%/Ethanol) in butan-2-ol (1 mL), DIPEA (15 eq), 5 h. Purification by chromatography (10-30% EtOAc in $CH_2Cl_2$) gave the title compound 7-amino-N-(5-(3-(2-cyanopropan-2-yl)benzamido)-2-methylphenyl)-2-(methylamino)thieno[2,3-b]pyrazine-6-carboxamide 18c (11 mg, 60%). $^1$H-NMR (400 MHz, DMSO-d6) 1.76 (s, 6H), 2.22 (s, 3H), 2.92 (d, J=4.7 Hz, 3H), 6.57 (s, 2H), 7.25 (d, J=8.2 Hz, 1H), 7.39 (q, J=5.1 and 4.7 Hz, 1H), 7.58-7.63 (m, 2H), 7.75 (d, 7.8 Hz, 1H), 7.82 (d, J=1.9 Hz, 1H), 7.94 (d, J=7.4 Hz, 1H), 8.05 (m, 1H) 8.08 (s, 1H), 9.19 (s, 1H), 10.30 (s, 1H). (m/z)=500 (M+H)$^+$.

Example 7

Synthesis of 7-amino-N-(5-(3-(2-cyanopropan-2-yl)benzamido)-2-methylphenyl)-2-(ethylamino)thieno[2,3-b]pyrazine-6-carboxamide (18d) (R=ethylamine)

Preparation analogous to general procedure I by using ethylamine hydrochloride (20 eq), in Butan-2-ol (1 mL), DIPEA (15 eq), 12 h. Purification by chromatography (10-20% EtOAc in $CH_2Cl_2$) gave the title compound 7-amino-N-(5-(3-(2-cyanopropan-2-yl)benzamido)-2-methylphenyl)-2-(ethylamino)thieno[2,3-b]pyrazine-6-carboxamide 18d (4 mg, 21%). $^1$H-NMR (400 MHz, DMSO-d6) 1.21 (t, J=7.0 Hz, 3H), 1.75 (s, 6H), 2.21 (s, 3H), 3.41 (m, 2H), 6.55 (s, 2H), 7.25 (d, J=8.2 Hz, 1H), 7.40 (t, 5.4 Hz, 1H), 7.58-7.63 (m, 2H), 7.75 (d, 7.8 Hz, 1H), 7.81 (d, J=1.9 Hz, 1H), 7.95 (d, J=7.4 Hz, 1H), 7.95 (d, J=7.4 Hz, 1H), 9.18 (s, 1H), 10.30 (s, 1H). (m/z)=514 (M+H)$^+$.

Example 8

Synthesis of 7-amino-N-(5-(3-(2-cyanopropan-2-yl)benzamido)-2-methylphenyl)-2-(4-methylpiperazin-1-yl)thieno[2,3-b]pyrazine-6-carboxamide (18e) (R=1-methylpiperazine)

Preparation analogous to general procedure I by using 1-methylpiperazine (10 eq), DIPEA (15 eq) in Butan-2-ol (1 mL), 5 h. Purification by chromatography (10-30% EtOAc in $CH_2Cl_2$) gave the title compound 7-amino-N-(5-(3-(2-cyanopropan-2-yl)benzamido)-2-methylphenyl)-2-(4-methylpiperazin-1-yl)thieno[2,3-b]pyrazine-6-carboxamide 18e (20 mg, 97%). (m/z)=569 (M+H)$^+$.

Example 9

Synthesis of 7-amino-N-(5-(3-(2-cyanopropan-2-yl)benzamido)-2-methylphenyl)-2-morpholinothieno[2,3-b]pyrazine-6-carboxamide (18f) (R=morpholine)

Preparation analogous to general procedure I by using morpholine (10 eq), DIPEA (15 eq) in Butan-2-ol (1 mL), 5 h. Purification by chromatography (0-30% EtOAc in $CH_2Cl_2$) gave the title compound 7-amino-N-(5-(3-(2-cyanopropan-2-yl)benzamido)-2-methylphenyl)-2-morpholinothieno[2,3-b]pyrazine-6-carboxamide 18f (11 mg, 54%). $^1$H-NMR (400 MHz, DMSO-d6) 1.76 (s, 6H), 2.21 (s, 3H), 3.68 (m, 4H), 3.76 (m, 4H), 6.76 (s, 2H), 7.25 (d, J=8.2 Hz, 1H), 7.60 (m, 2H), 7.75 (m, 1H), 7.82 (d, J=1.9 Hz, 1H), 7.94 (d, J=7.8 Hz, 1H), 8.05 (s, 1H), 8.54 (s, 1H), 9.25 (s, 1H), 10.31 (s, 1H). (m/z)=556 (M+H)$^+$.

Example 10

Synthesis of 7-amino-N-(5-(3-(2-cyanopropan-2-yl)benzamido)-2-methylphenyl)-2-(2-methoxyethylamino)thieno[2,3-b]pyrazine-6-carboxamide (18g) (R=2-aminoethyl methyl ether)

Preparation analogous to general procedure I by using 2-aminoethyl methyl ether (30 eq), DIPEA (60 eq) in Butan-2-ol (1 mL), 20 h. Purification by chromatography (10-30% EtOAc in $CH_2Cl_2$) gave the title compound 7-amino-N-(5-(3-(2-cyanopropan-2-yl)benzamido)-2-methylphenyl)-2-(2-methoxyethylamino)thieno[2,3-b]pyrazine-6-carboxamide 18g (11 mg, 55%). NMR (400 MHz, DMSO-d6) 1.75 (s, 6H), 2.21 (s, 3H), 3.31 (s, 3H), 3.52-3.62 (m, 4H), 6.58 (s, 2H), 7.24 (d, J=8.2 Hz, 1H), 7.50 (m, 1H), 7.60 (m, 2H), 7.75 (d, J=7.8 Hz, 1H), 7.82 (d, J=1.9 Hz, 1H), 7.95 (d, J=7.8, 1H), 8.05 (m, 1H), 8.14 (s, 1H), 9.19 (s, 1H), 10.31 (s, 1H). (m/z)=544 (M+H)$^+$.

Example 11

Synthesis of 7-amino-N-(5-(3-(2-cyanopropan-2-yl)benzamido)-2-methylphenyl)-2-(tetrahydro-2H-pyran-4-ylamino)thieno[2,3-b]pyrazine-6-carboxamide (18h) (R=4-aminotetrahydropyran)

Preparation analogous to general procedure I by using 4-aminotetrahydropyran hydrochloride (30 eq), triethylamine (60 eq) in butan-2-ol (1 mL), 30 h. Purification by chromatography (10-30% EtOAc in $CH_2Cl_2$) gave the title compound 7-amino-N-(5-(3-(2-cyanopropan-2-yl)benzamido)-2-methylphenyl)-2-(tetrahydro-2H-pyran-4-ylamino)thieno[2,3-b]pyrazine-6-carboxamide 18h (7 mg, 33%). NMR (400 MHz, DMSO-d6) 1.47 (m, 2H), 1.75 (s, 6H), 1.99 (m, 2H), 2.21 (s, 3H), 3.47 (m, 2H), 3.9 (m, 2H), 4.08 (m, 2H), 6.59 (s, 2H), 7.24 (d, J=8.6 Hz, 1H), 7.40 (d, J=7.0, 1H), 7.60 (t, J=7.8 Hz, 2H), 7.75 (d, J=7.8 Hz, 1H), 7.83 (d, J=1.9 Hz, 1H), 7.94 (d, J=7.8 Hz, 1H), 8.05 (s, 1H), 8.07 (s, 1H), 9.18 (s, 1H), 10.30 (s, 1H). (m/z)=570 (M+H)$^+$.

Example 12

Synthesis of 2-chloro-N-(5-(3-(2-cyanopropan-2-yl)benzamido)-2-methylphenyl)thieno[2,3-b]pyrazine-6-carboxamide (24)

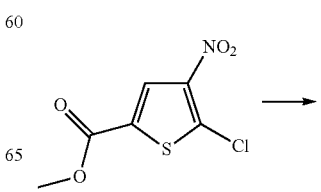

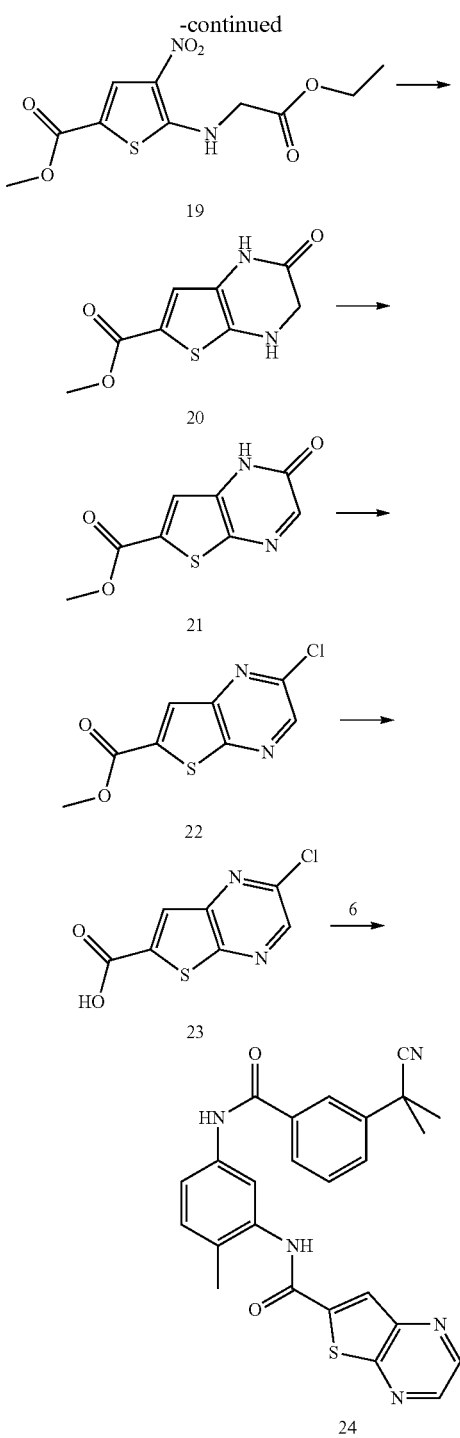

Step 1: synthesis of methyl 5-(2-ethoxy-2-oxoethylamino)-4-nitrothiophene-2-carboxylate (19)

A solution of 5-chloro-4-nitrothiophene-2-carboxylic acid methyl ester (6.03 g, 27.2 mmol), glycine ethyl ester hydrochloride (4.18 g, 29.9 mmol) and potassium carbonate (9.4 g, 68 mmol) in acetonitrile (200 mL) was stirred 4 h at 70° C. Quenched in ice/water. The resulting precipitation was collected by filtration, washed with water and dried to give methyl 5-(2-ethoxy-2-oxoethylamino)-4-nitrothiophene-2-carboxylate 19 (7.02 g, 89%). NMR (400 MHz, CDCl$_3$) 1.35 (t, J=7.0 Hz, 3H), 3.87 (s, 3H), 4.11 (d, J=5.5 Hz, 2H), 4.33 (q, J=14.0 and 7.0 Hz, 2H), 8.04 (s, 1H), 8.75 (br s, 1H). (m/z)=289 (M+H)$^+$.

Step 2: synthesis of methyl 2-oxo-1,2,3,4-tetrahydrothieno[3,2-b]pyrazine-6-carboxylate (20)

A mixture of methyl 5-(2-ethoxy-2-oxoethylamino)-4-nitrothiophene-2-carboxylate 19 (7.02 g, 24.35 mmol) and iron powder (4.08 g, 73.1 mmol) in acetic acid (100 mL) and water (15 mL) was stirred at 70° C. for 2 h. Quenched with ice/water and the resulting precipitate was collected by filtration to give crude methyl 2-oxo-1,2,3,4-tetrahydrothieno[3,2-b]pyrazine-6-carboxylate 20 (4.74 g, 92%). NMR (400 MHz, DMSO-d6) 3.69 (s, 3H), 3.87 (s, 2H), 7.06 (s, 1H), 7.21 (br s, 1H), 10.28 (br s, 1H). (m/z)=213 (M+H)$^+$.

Step 3: synthesis of methyl 2-oxo-1,2-dihydrothieno[3,2-b]pyrazine-6-carboxylate (21)

To a suspension of methyl 2-oxo-1,2,3,4-tetrahydrothieno[3,2-b]pyrazine-6-carboxylate 20 (515 mg, 2.427 mmol) in THF (30 mL) was added manganese(IV) oxide (2.11 g, 24.27 mmol). The reaction was stirred at rt for 30 min. manganese oxide was filtrated and washed with EtOAc. The filtrate was evaporated to give crude methyl 2-oxo-1,2-dihydrothieno[3,2-b]pyrazine-6-carboxylate 21 (483 mg, 95%). NMR (400 MHz, DMSO-d6) 3.90 (s, 3H), 7.62 (br s, 1H), 8.13 (s, 1H), 12.80 (br s, 1H). (m/z)=211 (M+H)$^+$.

Step 4: synthesis of methyl 2-chlorothieno[3,2-b]pyrazine-6-carboxylate (22)

A solution of methyl 2-oxo-1,2-dihydrothieno[3,2-b]pyrazine-6-carboxylate 21 (0.35 g, 1.665 mmol) in phosphorus oxychloride (10 mL, 107 mmol) was stirred at 105° C. for 5 h. Evaporated to dryness. Dissolved in EtOAc and washed with NaHCO3 solution, brine, dried and evaporated to give crude methyl 2-chlorothieno[3,2-b]pyrazine-6-carboxylate 22 (299 mg, 79%). NMR (400 MHz, CDCl$_3$) 4.02 (s, 3H), 8.11 (s, 1H), 8.61 (s, 1H). (m/z)=229 and 231 (M+H)$^+$.

Step 5: synthesis of 2-chlorothieno[3,2-b]pyrazine-6-carboxylic acid (23)

To a solution of methyl 2-chlorothieno[3,2-b]pyrazine-6-carboxylate 22 (1.23 g, 5.38 mmol) in THF (10 mL) and ethanol (10 mL) was added a solution of 2N sodium hydroxide (13.45 mL, 26.9 mmol). The reaction was stirred at rt for 1 h. The reaction mixture was poured in 2N HCl solution and the resulting precipitate was collected, washed with water and dried to give crude 2-chlorothieno[3,2-b]pyrazine-6-carboxylic acid 23 (1.027 g, 89%). NMR (400 MHz, DMSO-d6) 8.18 (s, 1H), 8.90 (s, 1H).

Step 6: synthesis of 2-chloro-N-(5-(3-(2-cyanopropan-2-yl)benzamido)-2-methylphenyl)thieno[2,3-b]pyrazine-6-carboxamide (24)

A solution of 2-chlorothieno[3,2-b]pyrazine-6-carboxylic acid 23 (350 mg, 1.631 mmol), HATU (744 mg, 1.957 mmol) and DIPEA (0.809 mL, 4.89 mmol) in DMF (8 mL) was stirred for 15 min. N-(3-amino-4-methylphenyl)-3-(2-cyanopropan-2-yl)benzamide hydrochloride 6 (538 mg, 1.631 mmol) was added and stirred overnight at rt. Quenched in citric acid solution (3%) and the resulting precipitate was collected. Triturating in acetonitrile gave the title compound 2-chloro-N-(5-(3-(2-cyanopropan-2-yl)benzamido)-2-methylphenyl)thieno[2,3-b]pyrazine-6-carboxamide 24 (450 mg, 56%). NMR (400 MHz, DMSO-d6) 1.76 (s, 6H), 2.26 (s, 3H), 7.32 (d, J=8.2 Hz, 1H), 7.58-7.68 (m, 2H), 7.76 (d, J=7.8 Hz, 1H), 7.87 (d, J=1.9, 1H), 7.95 (d, J=7.8 Hz, 1H), 8.05 (s, 1H), 8.49 (s, 1H), 8.89 (s, 1H), 10.38 (s, 1H), 10.59 (s, 1H). (m/z)=490 and 492 (M+H)+.

Example 13

Synthesis of N-(5-(3-(2-cyanopropan-2-yl)benzamido)-2-methylphenyl)-2-(ethylamino)thieno[2,3-b]pyrazine-6-carboxamide (25a) (R=ethylamine)

General Procedure II

A mixture of 24, amine and DIPEA or TEA in Butan-2-ol was stirred for 10 h at 150° C. in microwave. Water was added and extracted with EtOAc. Organic layer was washed with brine, dried and evaporated to give crude compound 25a-1 which was purified by HPLC to yield pure compound 25a-1.

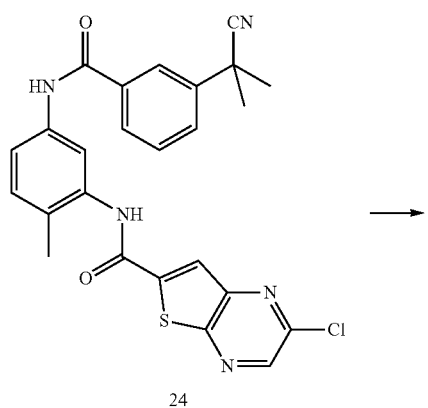

24

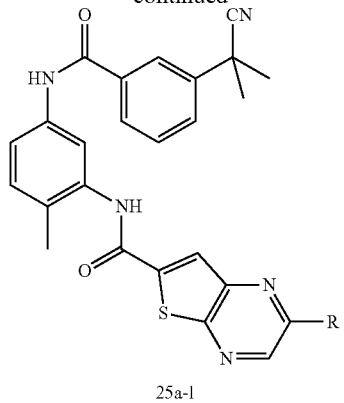

25a-1

25a: R = NHEthyl
25b: R = NHCH2CH2NMe2
25c: R = NMe2
25d: R = NHiPr
25e: R = NHMe 25f: R = —NH-CH2-(4-pyridyl)

25g: R = acetyl
25h: R = 3-pyridine
25i: R = 4-pyridine
25j: R = 3,5-pyrimidine

25k: R = 2-(dimethylamino)pyrimidin-5-yl

25l: R = Me

Synthesis of N-(5-(3-(2-cyanopropan-2-yl)benzamido)-2-methylphenyl)-2-(ethylamino)thieno[2,3-b]pyrazine-6-carboxamide (25a) (R=ethylamine)

Preparation analogous to general procedure II by using ethylamine hydrochloride (10 eq), triethylamine (25 eq) in butan-2-ol (3 mL) to give the title compound N-(5-(3-(2-cyanopropan-2-yl)benzamido)-2-methylphenyl)-2-(ethylamino)thieno[2,3-b]pyrazine-6-carboxamide 25a (102 mg, 66%). NMR (400 MHz, DMSO-d6) 1.21 (t, J=7.4 Hz, 3H), 1.76 (s, 6H), 2.25 (s, 3H), 3.35 (m, 2H), 7.29 (d, J=8.2 Hz, 1H), 7.45 (t, J=5 Hz, 1H), 7.58-7.67 (m, 2H), 7.75 (d, J=7.8 Hz, 1H), 7.85 (d, J=1.9 Hz, 1H), 7.95 (d, J=7.4 Hz, 1H), 8.05 (m, 2H), 8.13 (s, 1H), 10.18 (s, 1H), 10.35 (s, 1H). (m/z)=499 (M+H)+.

Example 14

Synthesis of N-(5-(3-(2-cyanopropan-2-yl)benzamido)-2-methylphenyl)-2-(2-(dimethylamino)ethylamino)thieno[2,3-b]pyrazine-6-carboxamide (25b) (R=1-amino-2-dimethylaminoethane)

Preparation analogous to general procedure II by using 1-amino-2-dimethylaminoethane (10 eq), triethylamine (10 eq) in Butan-2-ol (0.5 mL) to give the title compound N-(5-(3-(2-cyanopropan-2-yl)benzamido)-2-methylphenyl)-2-(2-(dimethylamino)ethylamino)thieno[2,3-b]pyrazine-6-carboxamide 25b (7 mg, 31%). NMR (400 MHz, DMSO-d6) 1.75 (s, 6H), 2.38 (br s, 2H), 3.33 (s, 6H), 3.50 (br s, 2H), 7.29 (d, J=8.2 Hz, 1H), 7.46 (br s, 1H), 7.61 (m, 2H), 7.76 (d, J=7.8 Hz, 1H), 7.85 (d, J=1.9 Hz, 1H), 7.95 (d, J=7.8 Hz, 1H), 8.05 (br s, 1H), 8.12 (s, 1H), 8.15 (s, 1H), 10.21 (s, 1H), 10.36 (s, 1H). (m/z)=542 (M+H)+.

Example 15

Synthesis of N-(5-(3-(2-cyanopropan-2-yl)benzamido)-2-methylphenyl)-2-(dimethylamino)thieno[2,3-b]pyrazine-6-carboxamide (25c) (R=dimethylamine)

Preparation analogous to general procedure II by using dimethylamine hydrochloride (10 eq), triethylamine (10 eq). The reaction mixture was quenched in water and the resulting precipitate was collected to give the title compound N-(5-(3-(2-cyanopropan-2-yl)benzamido)-2-methylphenyl)-2-(dimethylamino)thieno[2,3-b]pyrazine-6-carboxamide 25c (15 mg, 73%). NMR (400 MHz, DMSO-d6) 1.75 (s, 6H), 2.25 (s, 3H), 3.17 (s, 6H), 7.30 (d, J=8.2 Hz, 1H), 7.58-7.68 (m, 2H), 7.76 (d, J=7.8 Hz, 1H), 7.85 (s, 1H), 7.95 (d, J=7.8 Hz, 1H), 8.05 (s, 1H), 8.18 (s, 1H), 8.37 (s, 1H), 10.22 (s, 1H), 10.36 (s, 1H). (m/z)=499 (M+H)$^+$.

Example 16

Synthesis of N-(5-(3-(2-cyanopropan-2-yl)benzamido)-2-methylphenyl)-2-(isopropylamino)thieno[2,3-b]pyrazine-6-carboxamide (25d) (R=isopropylamine)

Preparation analogous to general procedure II by using isopropylamine (144 eq) in butan-2-ol (0.5 mL) to give the title compound N-(5-(3-(2-cyanopropan-2-yl)benzamido)-2-methylphenyl)-2-(isopropylamino)thieno[2,3-b]pyrazine-6-carboxamide 25d (7 mg, 33%). NMR (400 MHz, DMSO-d6) 1.22 (d, J=6.3 Hz, 6H), 1.75 (s, 6H), 2.25 (s, 3H), 4.05 (m, 1H), 7.29 (d, J=8.6 Hz, 1H), 7.34 (d, J=7.4 Hz, 1H), 7.58-7.66 (m, 2H), 7.75 (d, J=7.8 Hz, 1H), 7.85 (d, J=1.9 Hz, 1H), 7.95 (d, J=7.8, 1H), 8.01 (s, 1H), 8.05 (s, 1H), 8.13 (s, 1H), 10.16 (s, 1H), 10.35 (s, 1H). (m/z)=513 (M+H)$^+$.

Example 17

Synthesis of N-(5-(3-(2-cyanopropan-2-yl)benzamido)-2-methylphenyl)-2-(methylamino)thieno[2,3-b]pyrazine-6-carboxamide (25e) (R=methylamine)

Preparation analogous to general procedure II by using methylamine (10 eq), DIPEA (15 eq) in Butan-2-ol (1 mL). Purification by chromatography (10-30% EtOAc in CH$_2$Cl$_2$) gave the title compound N-(5-(3-(2-cyanopropan-2-yl)benzamido)-2-methylphenyl)-2-(methylamino)thieno[2,3-b]pyrazine-6-carboxamide 25e (5 mg, 25%). NMR (400 MHz, DMSO-d6) 1.76 (s, 6H), 2.25 (s, 3H), 2.87 (d, J=4.7 Hz, 3H), 7.3 (d, J=8.6 Hz, 1H), 7.44 (q, J=9.4 and 4.7 Hz, 1H), 7.58-7.367 (m, 2H), 7.76 (d, J=7.8 Hz, 1H), 7.85 (d, J=1.9 Hz, 1H), 7.95 (d, J=7.8 Hz, 1H), 8.05 (s, 2H), 8.14 (s, 1H), 10.19 (s, 1H), 10.35 (s, 1H). (m/z)=485 (M+H)$^+$.

Example 18

Synthesis of N-(5-(3-(2-cyanopropan-2-yl)benzamido)-2-methylphenyl)-2-(pyridin-4-ylmethylamino)thieno[2,3-b]pyrazine-6-carboxamide (25f) (R=4-(aminomethyl)pyridine)

Preparation analogous to general procedure II by using 4-(aminomethyl)pyridine (10 eq), DIPEA (15 eq), in Butan-2-ol (1 mL). Purification by chromatography (10-30% EtOAc in CH$_2$Cl$_2$) and HPLC gave the title compound N-(5-(3-(2-cyanopropan-2-yl)benzamido)-2-methylphenyl)-2-(pyridin-4-ylmethylamino)thieno[2,3-b]pyrazine-6-carboxamide 25f (7 mg, 20%). NMR (400 MHz, DMSO-d6) 1.76 (s, 6H), 2.23 (s, 3H), 4.61 (d, J=5.9 Hz, 2H), 7.27 (d, J=8.6 Hz, 1H), 7.37 (d, J=5.7 Hz, 1H), 7.57-7.65 (m, 2H), 7.75 (d, J=7.8 Hz, 1H), 7.82 (m, 1H), 7.94 (d, J=7.8 Hz, 1H), 8.03-8.15 (m, 3H), 8.19 (s, 1H), 8.50 (m, 2H), 10.15 (s, 1H), 10.34 (s, 1H). (m/z)=562 (M+H)$^+$.

Example 19

Synthesis of 2-acetyl-N-(5-(3-(2-cyanopropan-2-yl)benzamido)-2-methylphenyl)thieno[2,3-b]pyrazine-6-carboxamide (25g) (R=acetyl)

A solution of 2-chloro-N-(5-(3-(2-cyanopropan-2-yl)benzamido)-2-methylphenyl)thieno[2,3-b]pyrazine-6-carboxamide 24 (50 mg, 0.102 mmol), bis(triphenylphosphine)palladium(ii) chloride (7.16 mg, 10.2 μmol) and 1-ethoxyvinyltri-n-butyltin (0.103 mL, 0.306 mmol) toluene (3 mL) was stirred at 100° C. for 2 h. Cooled down to rt, 4N HCl in Dioxane (1 mL) was added and stirred for 1 h. Diluted with EtOAC, filtrated and evaporated. Purification by chromatography (0-10% EtOAc in CH$_2$Cl$_2$) gave the title compound 2-acetyl-N-(5-(3-(2-cyanopropan-2-yl)benzamido)-2-methylphenyl)thieno[2,3-b]pyrazine-6-carboxamide 25g (13 mg, 25.6%). NMR (400 MHz, DMSO-d6) 1.76 (s, 6H), 2.28 (s, 3H), 2.76 (s, 3H), 7.33 (d, J=8.2 Hz, 1H), 7.58-7.68 (m, 2H), 7.76 (d, J=7.8 Hz, 1H), 7.91 (d, J=1.9 Hz, 1H), 7.96 (d, J=7.8 Hz, 1H), 8.06 (s, 1H), 8.65 (s, 1H), 9.20 (s, 1H), 10.39 (s, 1H), 10.57 (s, 1H). (m/z)=498 (M+H)$^+$.

Example 20

Synthesis of N-(5-(3-(2-cyanopropan-2-yl)benzamido)-2-methylphenyl)-2-(pyridin-3-yl)thieno[2,3-b]pyrazine-6-carboxamide (25h) (R=3-pyridine)

A mixture of 24 (30 mg, 0.061 mmol), pyridine-3-boronic acid (11.2 mg, 0.092 mmol), tris(dibenzylideneacetone)dipalladium(0) (2.8 mg, 3.06 μmol), potassium phosphate, tribasic (26 mg, 0.122 mmol) and 2-dicyclohexylphosphino-2',4',6'-triisopropylbiphenyl (2.92 mg, 6.12 μmol) in butanol-2-ol was stirred at 100° C. for 30 min. Diluted with EtOAc and washed with water, brine, dried and evaporated. Triturating with acetonitrile gave the title compound N-(5-(3-(2-cyanopropan-2-yl)benzamido)-2-methylphenyl)-2-(pyridin-3-yl)thieno[2,3-b]pyrazine-6-carboxamide 25h (9 mg, 27.6%). NMR (400 MHz, DMSO-d6) 1.76 (s, 6H), 2.29 (s, 3H), 7.33 (d, J=8.2 Hz, 1H), 7.58-7.69 (m, 3H), 7.76 (d, J=7.8 Hz, 1H), 7.90 (s, 1H), 7.96 (d, J=7.8 Hz, 1H), 8.06 (s, 1H), 8.62 (m, 2H), 8.76 (d, J=4.7 Hz, 1H), 9.45 (m, 2H), 10.38 (s, 1H), 10.55 (s, 1H). (m/z)=533 (M+H)$^+$.

Example 21

Synthesis of N-(5-(3-(2-cyanopropan-2-yl)benzamido)-2-methylphenyl)-2-(pyridin-4-yl)thieno[2,3-b]pyrazine-6-carboxamide (25i) (R=4-pyridine)

Preparation analogous to the synthesis of 25h by using 2-(4-pyridyl)-5,5-dimethyl-1,2,3-dioxaborinane (1 eq). Purified by HPLC to give the title compound N-(5-(3-(2-cyano-propan-2-yl)benzamido)-2-methylphenyl)-2-(pyridin-4-yl)thieno[2,3-b]pyrazine-6-carboxamide 25i (4 mg, 18%). NMR (400 MHz, DMSO-d6) 1.76 (s, 6H), 2.28 (s, 3H), 7.33 (d, J=8.6 Hz, 1H), 7.58-7.68 (m, 2H), 7.76 (d, J=7.8 Hz, 1H), 7.90 (d, J=1.9 Hz, 1H), 7.95 (d, j=7.8 Hz, 1H0, 8.05 (s, 1H), 8.24 (m, 2H), 8.62 (s, 1H), 8.82 (m, 2H), 9.50 (s, 1H), 10.38 (s, 1H), 10.57 (s, 1H). (m/z)=533 (M+H)+.

Example 22

Synthesis of N-(5-(3-(2-cyanopropan-2-yl)benza-mido)-2-methylphenyl)-2-(pyrimidin-5-yl)thieno[2,3-b]pyrazine-6-carboxamide (25j) (R=5-pyrimidine)

Preparation analogous to the synthesis of 25h by using pyrimidine-5-boronic acid (1.5 eq). Purified by HPLC to give the title compound N-(5-(3-(2-cyanopropan-2-yl)benza-mido)-2-methylphenyl)-2-(pyrimidin-5-yl)thieno[2,3-b]pyrazine-6-carboxamide 25j (2 mg, 7%). NMR (400 MHz, DMSO-d6) 1.76 (s, 6H), 2.28 (s, 3H), 7.33 (d, J=8.6 Hz, 1H), 7.58-7.67 (m, 2H), 7.76 (d, J=7.8 Hz, 1H), 7.9 (d, J=1.9 Hz, 1H), 7.95 (d, J=8.2 Hz, 1H), 8.06 (s, 1H), 8.63 (br s, 1H), 9.37 (s, 1H), 9.51 (s, 1H), 9.61 (s, 2H), 10.38 (br s, 1H). (m/z)=534 (M+H)+.

Example 23

Synthesis of N-(5-(3-(2-cyanopropan-2-yl)benza-mido)-2-methylphenyl)-2-(2-(dimethylamino)pyri-midin-5-yl)thieno[2,3-b]pyrazine-6-carboxamide (25k) (R=2-dimethylamino-5-pyrimidine)

Preparation analogous to the synthesis of 25h by using 2-dimethylamino-pyrimidine-5-boronic acid pinacol ester (1.5 eq). Purified by HPLC to give the title compound N-(5-(3-(2-cyanopropan-2-yl)benzamido)-2-methylphenyl)-2-(2-(dimethylamino)pyrimidin-5-yl)thieno[2,3-b]pyrazine-6-carboxamide 25k (4 mg, 13%).

Example 24

Synthesis of N-(5-(3-(2-cyanopropan-2-yl)benza-mido)-2-methylphenyl)-2-methylthieno[2,3-b]pyra-zine-6-carboxamide (25l) (R=methyl)

A solution of 2-chloro-N-(5-(3-(2-cyanopropan-2-yl)ben-zamido)-2-methylphenyl)thieno[2,3-b]pyrazine-6-carboxa-mide 24 (40 mg, 0.082 mmol), potassium carbonate (22.56 mg, 0.163 mmol) and 1,1'-bis(diphenylphosphino)ferrocene-dichloro palladium(II) (5.91 mg, 8.16 μmol) in THF was heated to 60° C. for 6 h. The reaction mixture was poured in NH4Cl solution and extracted twice with EtOAc. Organic layer was washed with water, brine, dried and evaporated. Crude product triturated twice with CH2Cl2 to give N-(5-(3-(2-cyanopropan-2-yl)benzamido)-2-methylphenyl)-2-meth-ylthieno[2,3-b]pyrazine-6-carboxamide 25l (5 mg, 13%). NMR (400 MHz, DMSO-d6) 1.75 (s, 6H), 2.26 (s, 3H), 2.68 (s, 3H), 7.31 (d, J=8.2 Hz, 1H), 7.60 (t, J=7.8 Hz, 1H), 7.66 (d, J=8.6 Hz, 1H), 7.75 (m, 1H), 7.87 (d, J=2.3 Hz, 1H), 7.96 (d, J=7.4 Hz, 1H), 8.06 (s, 1H), 8.47 (s, 1H), 8.67 (s, 1H), 10.40 (s, 1H), 10.54 (br s, 1H). (m/z)=470 (M+H)+.

Example 25

Synthesis of N-(5-(2-(dimethylamino)isonicotina-mido)-2-methylphenyl)thieno[2,3-b]pyrazine-6-car-boxamide (31a) (R=dimethylamine)

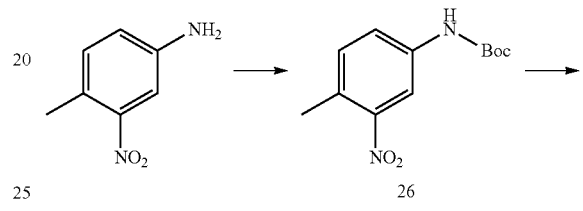

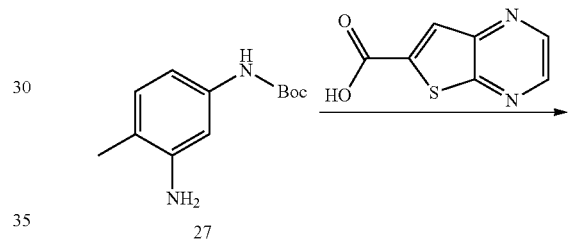

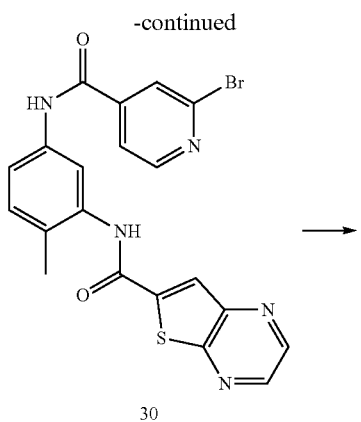

30

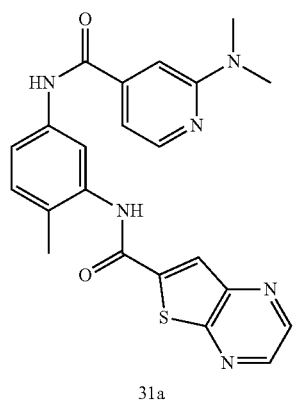 [SMILES: Cc1ccc(NC(=O)c2ccnc(N(C)C)c2)cc1NC(=O)c1cc2nccnc2s1]

31a

Step 1: synthesis of (4-Methyl-3-nitro-phenyl)-carbamic acid tert-butyl ester (26)

A solution of 4-methyl-3-nitroaniline (65 g, 427 mmol) in THF (1 L) was stirred at 65° C., and a solution of bis-(tert-butyl)anhydride (111 g, 511 mmol) was added. The reaction mixture was refluxed overnight, another amount of bis-(tert-butyl)anhydride (31 gram, 142 mol) was added and the mixture was refluxed for another 24 hours. After cooling, the reaction mixture was concentrated. Purified by chromatography (10% EtOAc in heptane) gave (4-Methyl-3-nitro-phenyl)-carbamic acid tert-butyl ester 26 (80 g, 74%).

Step 2: synthesis of (3-Amino-4-methyl-phenyl)-carbamic acid tert-butyl ester (27)

10% palladium on charcoal (6 g) was added to a solution of (4-methyl-3-nitro-phenyl)-carbamic acid tert-butyl ester 26 (60 g, 238 mmol) in ethanol (1200 mL). The mixture was hydrogenated at atmospheric pressure at room temperature for 18 h. The palladium catalyst was removed by filtration over celite and the solvent was removed by evaporation to give (3-Amino-4-methyl-phenyl)-carbamic acid tert-butyl ester 27 (51 g, 96%).

Step 3: synthesis of tert-butyl 4-methyl-3-(thieno[2,3-b]pyrazine-6-carboxamido)phenylcarbamate (28)

A solution of thieno[2,3-b]pyrazine-6-carboxylic acid (1.01 g, 5.61 mmol), HATU (1.8 g, 5.61 mmol) and DIPEA (1.953 mL, 11.21 mmol) in DMF (8 mL) was stirred for 15 min. (3-Amino-4-methyl-phenyl)-carbamic acid tert-butyl 27 (1.246 g, 5.61 mmol), DIPEA (1 eq) in DMF (8 mL) were added and stirred overnight at rt. Citric acid solution (3%) was added and extracted with EtOAc. Organic layer was washed with $NaHCO_3$ solution, brine, dried and evaporated. Purification by chromatography (0-20% EtOAc in $CH_2Cl_2$) gave tert-butyl 4-methyl-3-(thieno[2,3-b]pyrazine-6-carboxamido)phenylcarbamate 28 (1.43 g, 66.4%). (m/z)=385 $(M+H)^+$.

Step 4: synthesis of N-(5-amino-2-methylphenyl)thieno[2,3-b]pyrazine-6-carboxamide hydrochloride (29)

To a solution of tert-butyl 4-methyl-3-(thieno[2,3-b]pyrazine-6-carboxamido)phenylcarbamate 28 (5.36 g, 13.94 mmol) in dioxane (20 mL) was added 4N HCl/Dioxane (8.71 mL, 34.9 mmol). The reaction was stirred overnight at 60° C. Evaporated to dryness to give N-(5-amino-2-methylphenyl) thieno[2,3-b]pyrazine-6-carboxamide hydrochloride 29 (4.47 g, 100%). NMR (400 MHz, DMSO-d6) 2.32 (s, 3H), 7.25 (dd, J=8.2 and 2.3 Hz, 1H), 7.44 (d, J=8.6 Hz, 1H), 7.49 (d, J=1.9 Hz, 1H), 8.65 (s, 1H), 8.77 (d, J=2.3 Hz, 1H), 8.90 (d, J=2.3 Hz, 1H), 10.3 (br s, 2H), 10.70 (s, 1H).

Step 5: synthesis of N-(5-(2-bromoisonicotinamido)-2-methylphenyl)thieno[2,3-b]pyrazine-6-carboxamide (30)

A solution of 2-bromoisonicotinic acid (160 mg, 0.792 mmol), HATU (331 mg, 0.871 mmol) and DIPEA (0.655 mL, 3.96 mmol) in DMF (8 mL) was stirred at rt for 10 min. N-(5-amino-2-methylphenyl)thieno[2,3-b]pyrazine-6-carboxamide hydrochloride 29 (248 mg, 0.871 mmol) was added and stirred at rt for 3 h. Quenched in 3% citric acid solution and the resulting precipitate was collected. Triturating with acetonitrile gave N-(5-(2-bromoisonicotinamido)-2-methylphenyl)thieno[2,3-b]pyrazine-6-carboxamide (30) (163 mg, 44%). (m/z)=468 and 470 $(M+H)^+$.

Step 6: synthesis of N-(5-(2-(dimethylamino)isonicotinamido)-2-methylphenyl)thieno[2,3-b]pyrazine-6-carboxamide (31a) (R=dimethylamine)

To a solution of N-(5-(2-bromoisonicotinamido)-2-methylphenyl)thieno[2,3-b]pyrazine-6-carboxamide 30 (25 mg, 0.053 mmol) in ethanol (1 mL) was added dimethylamine HCl (24.07 mg, 0.534 mmol) and TEA (10 eq). The resulting mixture was heated at 80° C. overnight and 2 h at 150° C. in microwave. Quenched in 3% citric acid solution and extracted with $CH_2Cl_2$ (2×). The combined organic layers were dried with $Na_2SO_4$ and evaporated. Triturating with ethyl acetate/heptane gave the title compound N-(5-(2-(dimethylamino)isonicotinamido)-2-methylphenyl)thieno[2,3-b]pyrazine-6-carboxamide 31a (11.3 mg, 49%). NMR (400 MHz, DMSO-d6) 2.26 (s, 3H), 3.11 (s, 6H), 7.03 (d, J=5.1 Hz, 1H), 7.10 (br s, 1H), 7.31 (d, J=8.2 Hz, 1H), 7.63 (dd, J=8.2 and 1.9 Hz, 1H), 7.87 (d, J=1.9 Hz, 1H), 8.23 (d, J=5.1

Hz, 1H), 8.56 (br s, 1H), 8.76 (d, J=2.3 Hz, 1H), 8.89 (d, J=2.3 Hz, 1H), 10.39 (br s, 1H), 10.54 (br s, 1H). (m/z)=433 (M+H)⁺.

Example 26

Synthesis of N-(2-methyl-5-(2-(pyrrolidin-1-yl)isonicotinamido)phenyl)thieno[2,3-b]pyrazine-6-carboxamide (31b) (R=pyrrolidine)

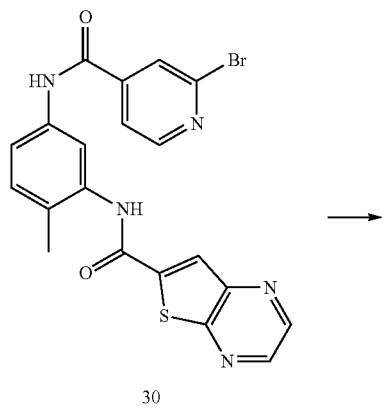

A mixture of N-(5-(2-bromoisonicotinamido)-2-methylphenyl)thieno[2,3-b]pyrazine-6-carboxamide 30 (25 mg, 0.053 mmol) in pyrrolidine (0.5 mL) was heated at 80° C. overnight. Quenched in 3% citric acid solution and extracted with CH₂Cl₂ (2×). The combined organic layers were dried with Na₂SO₄ and concentrated in vacuo. Purification by chromatography CH₂Cl₂/MeOH (97/3) and triturating with acetonitrile gave the title compound N-(2-methyl-5-(2-(pyrrolidin-1-yl)isonicotinamido)phenyl)thieno[2,3-b]pyrazine-6-carboxamide 31b (10.7 mg, 44%). NMR (400 MHz, DMSO-d6) 1.97 (m, 4H), 2.26 (s, 3H), 3.45 (m, 4H), 6.88 (s, 1H), 6.98 (dd, J=5.1 and 1.2 Hz, 1H), 7.30 (d, J=8.6 Hz, 1H), 7.62 (dd, J=8.23 and 1.6 Hz, 1H), 7.87 (d, J=2.3 Hz, 1H), 8.21 (d, J=5.1 Hz, 1H), 8.53 (br s, 1H), 8.75 (d, J=2.3 Hz, 1H), 8.88 (d, J=2.3 Hz, 1H), 10.33 (s, 1H), 10.52 (s, 1H). (m/z)=459 (M+H)⁺.

Example 27

Synthesis of N-(5-(3-(2-cyanopropan-2-yl)benzamido)-2-methylphenyl)thieno[2,3-b]pyrazine-6-carboxamide (32a)

General Procedure III

A solution of acid, TBTU or HATU and DIPEA in DMF was stirred for 15 min. N-(5-amino-2-methylphenyl)thieno[2,3-b]pyrazine-6-carboxamide hydrochloride 29 (1 eq) was added and stirred o/n at 60° C. Water was added and extracted with CH₂Cl₂. Organic layer was dried and evaporated to give crude compound 32 which was purified by chromatography, HPLC or triturating to give the title compounds 32.

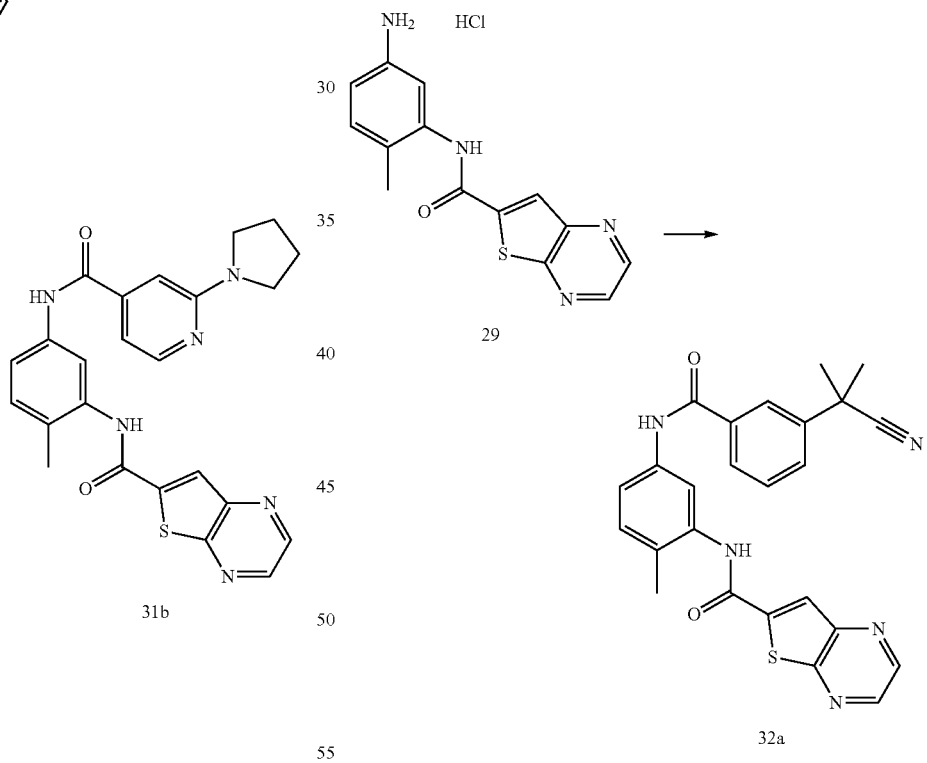

Preparation analogous to general procedure III by using 3-(2-cyanopropan-2-yl)benzoic acid 3 (1.2 eq), HATU (1.2 eq) and DIPEA (3 eq) in DMF (4 mL). The crude compound was purified by HPLC to give the title compound N-(5-(3-(2-cyanopropan-2-yl)benzamido)-2-methylphenyl)thieno[2,3-b]pyrazine-6-carboxamide 32a (120 mg, 56%). NMR (400 MHz, DMSO-d6) 1.76 (s, 6H), 2.26 (s, 3H), 7.32 (d, J=8.2 Hz, 1H), 7.58-7.66 (m, 2H), 7.76 (d, J=7.8 Hz, 1H), 7.87 (d, J=1.9, 1H), 7.95 (d, J=7.8 Hz, 1H), 8.05 (m, 1H), 8.55 (s, 1H), 8.76 (d, J=2.3 Hz, 1H), 8.89 (d, J=2.3 Hz, 1H), 10.38 (s, 1H), 10.53 (s, 1H). (m/z)=456 (M+H)⁺.

Example 28

Synthesis of N-(5-(4-methoxy-3-(trifluoromethyl)benzamido)-2-methylphenyl)thieno[2,3-b]pyrazine-6-carboxamide (32b)

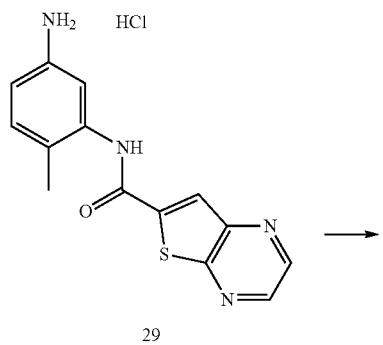

Example 29

Synthesis of N-(5-(3-(1-cyanocyclopropyl)benzamido)-2-methylphenyl)thieno[2,3-b]pyrazine-6-carboxamide (32c)

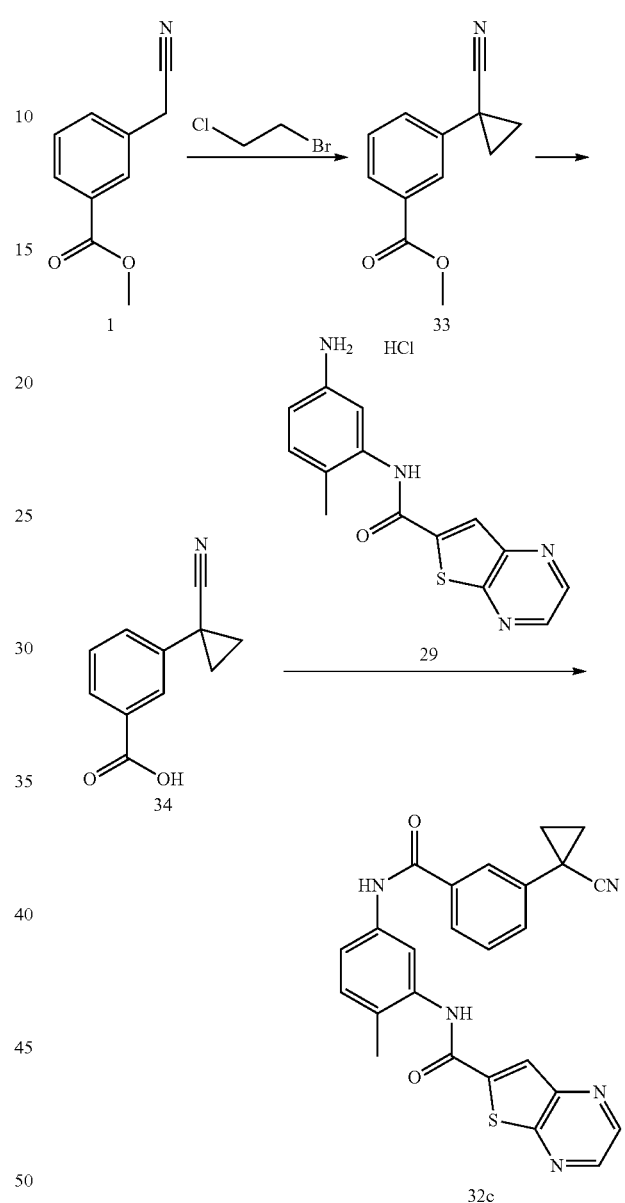

Preparation analogous to general procedure III by using 4-methoxy-3-(trifluoromethyl)benzoicacid (1.5 eq), TBTU (1.5 eq) and DIPEA (3 eq). The crude compound was purified by chromatography (20% EtOAc in $CH_2Cl_2$) to give the title compound N-(5-(4-methoxy-3-(trifluoromethyl)benzamido)-2-methylphenyl)thieno[2,3-b]pyrazine-6-carboxamide 32b (21 mg, 56%). NMR (400 MHz, DMSO-d6) 2.26 (s, 3H), 3.99 (s, 3H), 7.31 (d, J=8.6 Hz, 1H), 7.43 (d, J=8.6; H, 1H), 7.64 (dd, J=8.2 and 1.9 Hz, 1H), 7.87 (d, J=1.9 Hz, 1H), 8.24-8.32 (m, 2H), 8.55 (s, 1H), 8.76 (d, J=2.3 Hz, 1H), 8.89 (d, J=2.3 Hz, 1H), 10.36 (s, 1H), 10.51 (s, 1H). (m/z)=487 (M+H)$^+$.

Step 1: synthesis of methyl 3-(1-cyanocyclopropyl)benzoate (33)

To a solution of methyl 3-(cyanomethyl)benzoate 1 (2 g, 11.4 mmol) in DMSO (30 mL) was added NaH (60%, 913 mg, 23 mmol) in one portion. 1-bromo-2-chloroethane (1.164 mL, 11.4 mmol) was added slowly at 0° C. and stirring continued for 18 h at 25° C. The reaction was quenched with water, extracted with EtOAc, dried, and evaporated. Compound dissolved again in EtOAc and washed with $NaHCO_3$ solution, brine, dried and concentrated to affording methyl 3-(1-cyanocyclopropyl)benzoate 33 (1.56 g, 68%). NMR (400 MHz, $CDCl_3$) 1.47 (m, 2H), 1.78 (m, 2H), 3.93 (s, 3H), 7.45 (t, J=7.8 Hz, 1H), 7.59 (m, 1H), 7.88 (t, J=1.6 Hz, 1H), 7.97 (m, 1H).

Step 2: synthesis of 3-(1-cyanocyclopropyl)benzoic acid (34)

A solution of 33 (1.56 g, 7.75 mmol) in 25 mL of THF/MeOH/H$_2$O (3/1/1) was added lithium hydroxide (613 mg, 25.6 mmol) in water (5 mL). The mixture was stirred overnight at rt. Concentrated in vacuo and the resulting solution was acidified with 1N HCl (until pH=1). The resulting precipitate was collected and washed with water and dried to give 3-(1-cyanocyclopropyl)benzoic acid 34 (1.19 g, 82%). NMR (400 MHz, CDCl$_3$) 1.49 (m, 2H), 1.81 (m, 2H), 7.50 (t, J=7.8 Hz, 1H), 7.67 (m, 1H), 7.94 (m, 1H), 8.05 (m, 1H).

Step 3: synthesis of N-(5-(3-(1-cyanocyclopropyl)benzamido)-2-methylphenyl)thieno[2,3-b]pyrazine-6-carboxamide (32c)

Preparation analogous to general procedure III by using 3-(1-cyanocyclopropyl)benzoic 34 (1.5 eq), TBTU (1.5 eq) and DIPEA (3 eq). The crude compound was purified by chromatography (50% EtOAc in CH$_2$Cl$_2$) to give the title compound N-(5-(3-(1-cyanocyclopropyl)benzamido)-2-methylphenyl)thieno[2,3-b]pyrazine-6-carboxamide 32c (9 mg, 32%). NMR (400 MHz, DMSO-d6) 1.64 (m, 2H), 1.82 (m, 2H), 2.26 (s, 3H), 7.31 (d, J=8.2 Hz, 1H), 7.55-7.60 (m, 2H), 7.63 (dd, J=8.2 and 2.3 Hz, 1H), 7.83-7.92 (m, 3H), 8.55 (s, 1H), 8.76 (d, J=2.3 Hz, 1H), 8.89 (d, J=2.3 Hz, 1H), 10.35 (s, 1H), 10.52 (s, 1H). (m/z)=454 (M+H)$^+$.

Example 30

Synthesis of N-(5-(3-tert-butyl-1H-pyrazole-5-carboxamido)-2-methylphenyl)thieno[2,3-b]pyrazine-6-carboxamide (32d)

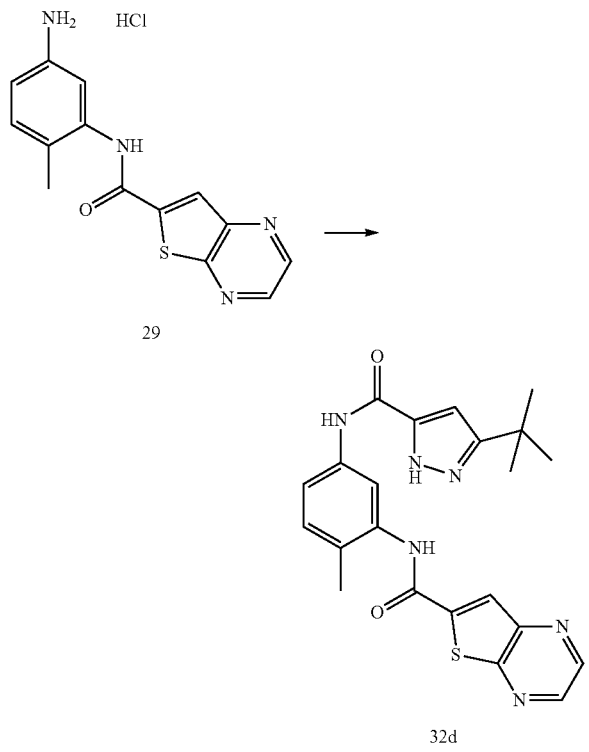

Preparation analogous to general procedure III by using 5-tert-butyl-2h-pyrazole-3-carboxylic acid (1.5 eq), TBTU (1.5 q) and DIPEA (3 eq). The crude compound was purified by chromatography (60% EtOAc in CH$_2$Cl$_2$) to give the title compound N-(5-(3-tert-butyl-1H-pyrazole-5-carboxamido)-2-methylphenyl)thieno[2,3-b]pyrazine-6-carboxamide 32d (13 mg, 48%). NMR (400 MHz, DMSO-d6) 1.2 (s, 9H), 2.23 (s, 3H), 6.51 (s, 1H), 7.25 (d, J=8.6 Hz, 1H), 7.63 (dd, J=8.6 and 1.9 Hz, 1H), 7.91 (s, 1H), 8.54 (s, 1H), 8.76 (d, J=2.3 Hz, 1H), 8.88 (d, J=2.3 Hz, 1H), 9.96 (s, 1H), 10.53 (s, 1H). (m/z)=435 (M+H)$^+$.

Example 31

Synthesis of N-(2-methyl-5-(4-methyl-3-(trifluoromethyl)benzamido)phenyl)thieno[2,3-b]pyrazine-6-carboxamide (32e)

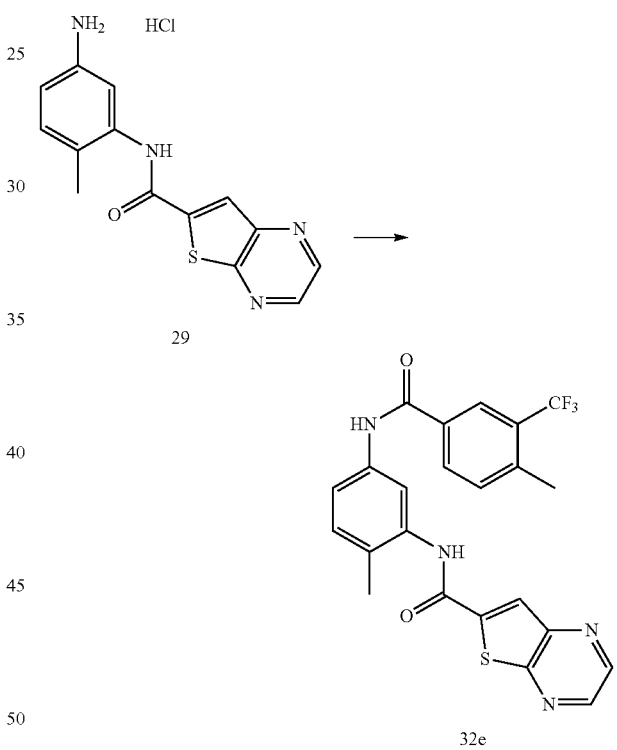

Preparation analogous to the general procedure by using 4-methyl-3-(trifluoromethyl)benzoicacid (0.9 eq), HATU (1.2 eq) and DIPEA (5 eq). The crude compound was triturated with acetonitrile to give the title compound N-(2-methyl-5-(4-methyl-3-(trifluoromethyl)benzamido)phenyl)thieno[2,3-b]pyrazine-6-carboxamide 32e (11.8 mg, 14%). NMR (400 MHz, DMSO-d6) 2.26 (s, 3H), 2.53 (s, 3H), 7.32 (d, J=8.6 Hz, 1H), 7.61-7.67 (m, 2H), 7.89 (d, J=2.3 Hz, 1H), 8.17 (d, J=7.8 Hz, 1H), 8.26 (s, 1H), 8.55 (s, 1H), 8.76 (d, J=2.3 Hz, 1H), 8.89 (d, J=2.3 Hz, 1H), 10.46 (s, 1H), 10.52 (s, 1H). (m/z)=471 (M+H)$^+$.

Example 32

Synthesis of N-(5-(3-fluoro-5-(trifluoromethyl)benzamido)-2-methylphenyl)thieno[2,3-b]pyrazine-6-carboxamide (32f)

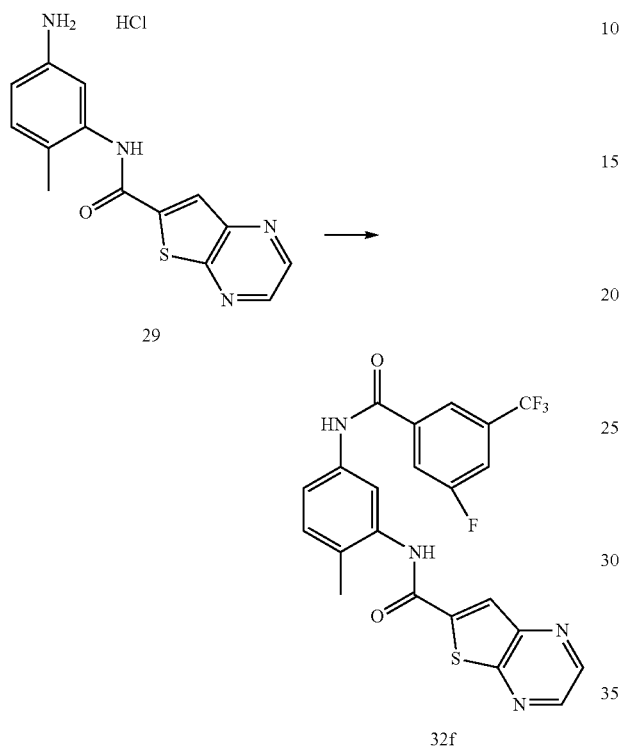

Preparation analogous to the general procedure by using 3-fluoro-5-(trifluoromethyl)benzoicacid (1.1 eq), HATU (1.2 eq), DIPEA (5 eq). The crude compound was triturated with acetonitrile to give the title compound N-(5-(3-fluoro-5-(trifluoromethyl)benzamido)-2-methylphenyl)thieno[2,3-b]pyrazine-6-carboxamide 32f (6.8 mg, 16%). NMR (400 MHz, DMSO) 2.27 (s, 3H), 7.33 (d, J=8.2 Hz, 1H), 7.64 (dd, J=8.2 and 2.3 Hz, 1H), 7.89 (d, J=1.9, 1H), 7.98 (d, J=8.6, 1H), 8.14 (d, J=9.3 Hz, 1H), 8.19 (s, 1H), 8.54 (br s, 1H), 8.76 (d, J=2.3 Hz, 1H), 8.88 (d, J=2.3 Hz, 1H), 10.53 (br s, 1H), 10.57 (br s, 1H). (m/z)=475 (M+H)+.

Example 33

Synthesis of N-(2-methyl-5-(4-((4-methylpiperazin-1-yl)methyl)-3-(trifluoromethyl)benzamido)phenyl)thieno[2,3-b]pyrazine-6-carboxamide (32g)

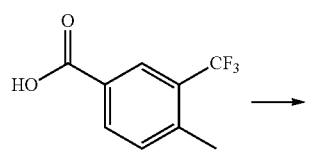

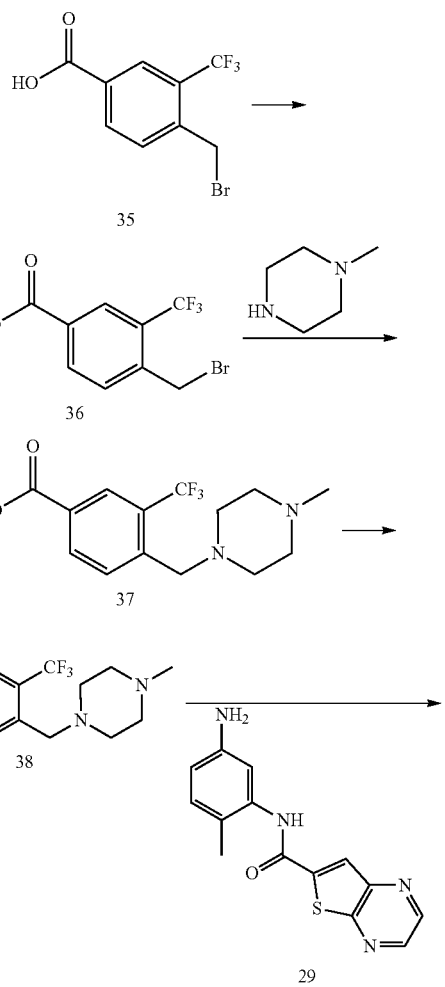

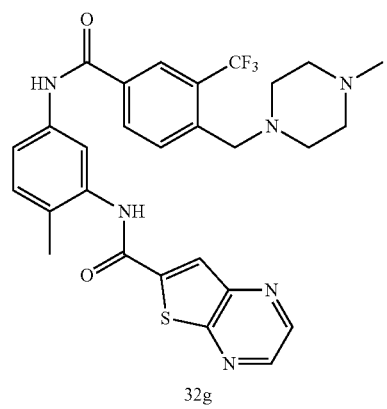

Step 1: synthesis of 4-(bromomethyl)-3-(trifluoromethyl)benzoic acid (35)

To a solution of sodium bromate (1109 mg, 7.35 mmol) in H$_2$O (3.3 mL) was added 4-methyl-3-trifluoromethyl-benzoic acid (500 mg, 2.449 mmol) in ethyl acetate (5 mL), followed by a solution of sodium bisulfite (765 mg, 7.35 mmol) in H$_2$O (9 mL) over a period of about 15 min. The mixture was stirred overnight at room temperature and overnight at 50° C. The mixture was poured in ether (50 mL). The aqueous layer was extracted twice with ether and the combined organic layer was washed with anhydrous Na$_2$S$_2$O$_3$ solution, dried, filtered and concentrated in vacuo to give the crude 4-(bromomethyl)-3-(trifluoromethyl)benzoic acid 35 (563 mg, 81%) which was used without further purification. (m/z)=282 and 284 (M+H)$^+$.

Step 2: synthesis of 4-bromomethyl-3-trifluoromethyl-benzoic acid ethyl ester (36)

4-(bromomethyl)-3-(trifluoromethyl)benzoic acid 35 (650 mg, 2.296 mmol) was dissolved in ethanol (30 mL). Concentrated H$_2$SO$_4$ (1.224 mL, 22.96 mmol) was slowly added. The resulting mixture was heated at 80° C. overnight. The reaction mixture was cooled and neutralized with saturated Na$_2$CO$_3$ Solution. The resulting precipitate was collected to give crude 4-bromomethyl-3-trifluoromethyl-benzoic acid ethyl ester 36 (550 mg, 77%) which was used without further purification. (m/z)=311 an 313 (M+H)$^+$.

Step 3: synthesis of 4-(4-methyl-piperazin-1-ylmethyl)-3-trifluoromethyl-benzoic acid ethyl ester (37)

To a solution of 4-bromomethyl-3-trifluoromethyl-benzoic acid ethyl ester 36 (120 mg, 0.386 mmol) in THF (4 mL) and DMF (1 mL) was added K$_2$CO$_3$ (80 mg, 0.579 mmol) and 3-(dimethylamino)pyrrolidine (0.043 mL, 38.6 mg, 0.386 mmol). The resulting mixture was stirred at rt for 4 h. The reaction mixture was poured out in water and extracted twice with ethyl acetate. The combined organic extracts were dried, filtered and concentrated in vacuo. The crude material was purified by chromatography CH$_2$Cl$_2$/MeOH (95/5) to give pure 4-(4-methyl-piperazin-1-ylmethyl)-3-trifluoromethyl-benzoic acid ethyl ester 37 (21 mg, 16%).

Step 4: synthesis of 4-(4-methyl-piperazin-1-ylmethyl)-3-trifluoromethyl-benzoic acid (38)

To a solution of 4-(4-methyl-piperazin-1-ylmethyl)-3-trifluoromethyl-benzoic acid ethyl ester 37 (21 mg, 0.064 mmol) in ethanol (5 mL) was added 2N NaOH (0.318 mL, 0.636 mmol). The resulting mixture was stirred at rt for 2 h. The reaction mixture was acidified with 2N HCl solution and concentrated in vacuo to give the crude 4-(4-methyl-piperazin-1-ylmethyl)-3-trifluoromethyl-benzoic acid 38 (20 mg, 104%) which was used without further purification.

Step 5: synthesis of N-(2-methyl-5-(4-((4-methylpiperazin-1-yl)methyl)-3-(trifluoromethyl)benzamido)phenyl)thieno[2,3-b]pyrazine-6-carboxamide (32g)

Preparation analogous to general procedure III by using 4-(4-methyl-piperazin-1-ylmethyl)-3-trifluoromethyl-benzoic acid 38 (0.83 eq), DIPEA (5 eq), HATU (1.2 eq) in DMF (2 mL). Purified by triturating with CH$_2$Cl$_2$ and the resulting white solid was washed with acetonitrile to give the title compound N-(2-methyl-5-(4-((4-methylpiperazin-1-yl)methyl)-3-(trifluoromethyl)benzamido)phenyl)thieno[2,3-b]pyrazine-6-carboxamide 32g (17 mg, 45%). NMR (400 MHz, DMSO-d6) 2.27 (s, 3H), 2.58-2.77 (m, 8H), 3.34 (s, 3H), 3.78 (s, 2H), 7.32 (d, J=8.2 Hz, 1H), 7.65 (dd, J=8.2 and 1.9 Hz, 1H), 7.88-7.96 (m, 2H), 8.24-8.32 (m, 2H), 8.56 (s, 1H), 8.77 (d, J=2.3 Hz, 1H), 8.89 (d, J=2.3 Hz, 1H), 10.52 (br s, 2H). (m/z)=569 (M+H)$^+$.

Example 34

Synthesis of N-(5-(3-(1H-pyrazol-1-yl)benzamido)-2-methylphenyl)thieno[2,3-b]pyrazine-6-carboxamide (32h)

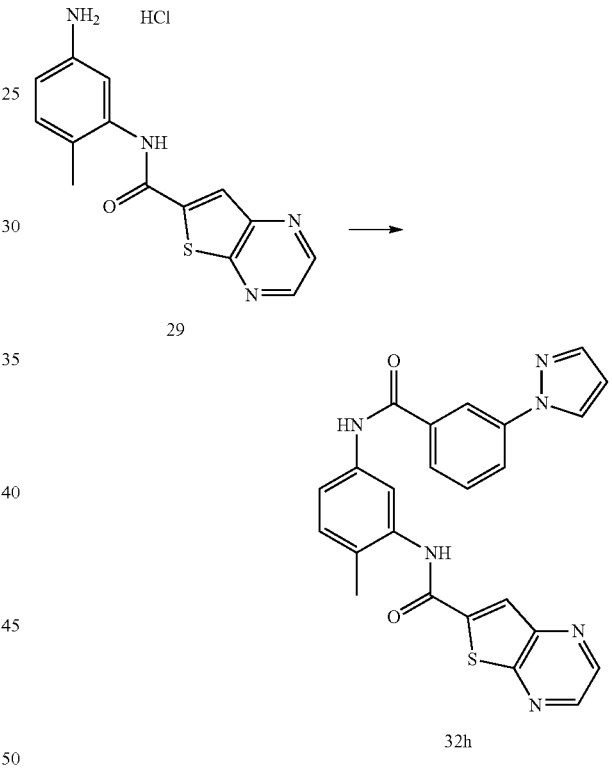

Preparation analogous to general procedure III by using 3-(1H-pyrazol-1-yl)benzoic acid (0.9 eq), HATU (1.1 eq) and DIPEA (5 eq) in DMF (2 mL). The crude compound was purified by chromatography (3% methanol in CH$_2$Cl$_2$) and triturated with acetonitrile to give the title compound N-(5-(3-(1H-pyrazol-1-yl)benzamido)-2-methylphenyl)thieno[2,3-b]pyrazine-6-carboxamide 32h (16 mg, 34%). NMR (400 MHz, DMSO-d6) 2.27 (s, 3H), 6.61 (s, 1H), 7.32 (d, J=8.6 Hz, 1H), 7.63-770 (m, 2H), 7.81 (s, 1H), 7.87-7.94 (m, 2H), 8.06 (d, J=7.8 Hz, 1H), 8.40 (s, 1H), 8.55 (s, 1H), 8.62 (d, J=2.7 Hz, 1H), 8.76 (d, J=2.3 Hz, 1H), 8.89 (d, J=2.3 Hz, 1H), 10.45 (s, 1H), 10.53 (s, 1H). (m/z)=455 (M+H)$^+$.

Example 35

Synthesis of N-(2-methyl-5-(3-(trifluoromethoxy)benzamido)phenyl)thieno[2,3-b]pyrazine-6-carboxamide (32i)

Example 36

Synthesis of N-(5-(3-(4-cyanotetrahydro-2H-pyran-4-yl)benzamido)-2-methylphenyl)thieno[2,3-b]pyrazine-6-carboxamide (32j)

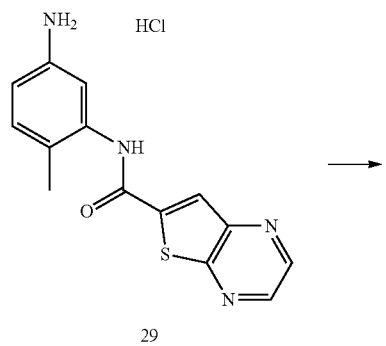

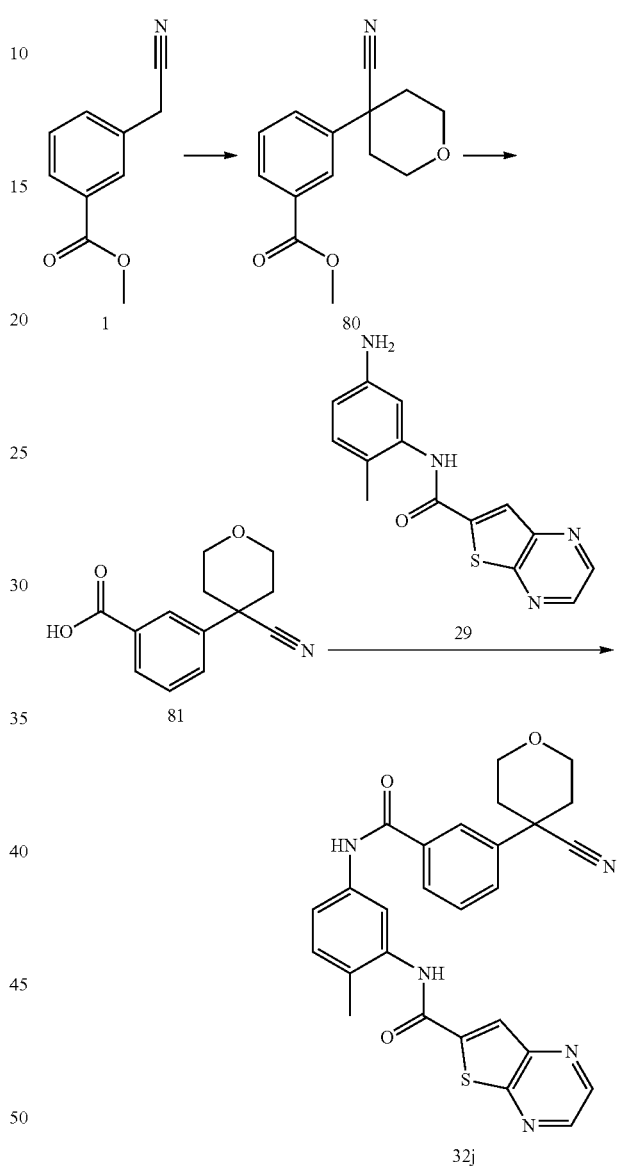

Preparation analogous to general procedure III by using 3-(trifluoromethoxy)benzoic acid (0.9 eq), HATU (1.1 eq) and DIPEA (5 eq) in DMF (2 mL). The crude compound was purified by chromatography (3% methanol in $CH_2Cl_2$) and triturated with acetonitrile to give the title compound N-(2-methyl-5-(3-(trifluoromethoxy)benzamido)phenyl)thieno[2,3-b]pyrazine-6-carboxamide 32i (19 mg, 42%). NMR (400 MHz, DMSO-d6) 2.27 (s, 3H), 7.32 (d, J=8.6 Hz, 1H), 7.60-7.74 (m, 3H), 7.89 (d, J=2.3 Hz, 1H), 7.93 (s, 1H), 8.03 (d, J=7.8 Hz, 1H), 8.55 (s, 1H), 8.76 (d, J=2.3 Hz, 1H), 8.89 (d, J=2.3 Hz, 1H), 10.44 (s, 1H), 10.52 (s, 1H). (m/z)=473 $(M+H)^+$.

Step 1: synthesis of methyl 3-(4-cyanotetrahydro-2H-pyran-4-yl)benzoate (80)

To a solution of methyl 3-(cyanomethyl)benzoate 1 (2 g, 11.4 mmol) in DMSO (20 mL) was added NaH (60%, 959 mg, 24.0 mmol) portion wise over 10 min. The reaction mixture was stirred for 40 min at rt and then bis(2-chloroethyl)ether (1.27 mL, 10.9 mmol) was added slowly and stirring continued for 18 hours. The reaction was poured into water and extracted with EtOAc/toluene (2:1). The combined extracts were washed with 2N HCl solution, water, brine, dried and evaporated the crude methyl 3-(4-cyanotetrahydro-2H-pyran-4-yl)benzoate 80 (1.25 g, 44%).

Step 2: synthesis of 3-(4-cyanotetrahydro-2H-pyran-4-yl)benzoic acid (81)

To a solution of methyl 3-(4-cyanotetrahydro-2H-pyran-4-yl)benzoate 80 (1.3 g, 5.3 mmol) in (25 mL) of THF/MeOH/H2O (3/1/1) was added lithium hydroxide (419 mg, 17.5 mmol) in water (5 mL) and stirred overnight at rt. The reaction mixture was concentrated and extracted with $CH_2Cl_2$ to remove the excess of bis(2-chloroethyl)ether. The aqueous layer was then acidified with 2N HCl solution to (pH=1) and extracted with $CH_2Cl_2$. Organic layer was washed with brine and evaporated to give 3-(4-cyanotetrahydro-2H-pyran-4-yl)benzoic acid 81 (526 mg, 42%).

Step 3: synthesis of N-(5-(3-(4-cyanotetrahydro-2H-pyran-4-yl)benzamido)-2-methylphenyl)thieno[2,3-b]pyrazine-6-carboxamide (32j)

Preparation analogous to general procedure III by using 3-(4-cyanotetrahydro-2H-pyran-4-yl)benzoic acid 81 (0.9 eq), HATU (1.1 eq) and DIPEA (5 eq) in DMF (2 mL). The crude compound was purified by chromatography (3% methanol in $CH_2Cl_2$) and triturated with acetonitrile to give the title compound N-(5-(3-(4-cyanotetrahydro-2H-pyran-4-yl)benzamido)-2-methylphenyl)thieno[2,3-b]pyrazine-6-carboxamide 32j (12 mg, 28%). NMR (400 MHz, DMSO-d6) 2.17 (m, 4H), 2.27 (s, 3H), 3.69 (m, 2H), 4.06 (m, 2H), 7.32 (d, J=8.6 Hz, 1H), 7.64 (m, 2H), 7.80 (d, J=7.8 Hz, 1H), 7.87 (d, J=1.9 Hz, 1H), 7.98 (d, J=7.8 Hz, !H), 8.09 (s, 1H), 8.55 (s, 1H), 8.76 (d, J=2.3 Hz, 1H), 8.89 (d, J=2.3 Hz, 1H), 10.37 (br s, 1H), 10.52 (br s, 1H). (m/z)=498 (M+H)$^+$.

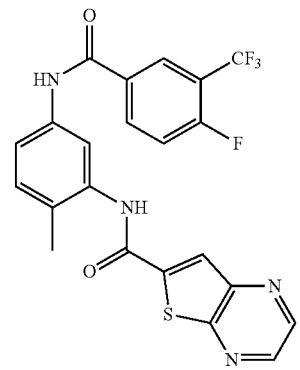

32k

Preparation analogous to general procedure III by using 4-fluoro-3-(trifluoromethyl)benzoic acid (0.9 eq), HATU (1.1 eq) and DIPEA (5 eq) in DMF (2 mL). The crude compound was purified triturating with acetonitrile to give the title compound N-(5-(4-fluoro-3-(trifluoromethyl)benzamido)-2-methylphenyl)thieno[2,3-b]pyrazine-6-carboxamide 32k (10 mg, 12%). NMR (400 MHz, DMSO) 2.26 (s, 1H), 7.32 (d, J=8.6 Hz, 1H), 7.63 (dd, J=8.2 and 1.9 Hz, 1H), 7.72 (m, 1H), 7.88 (d, J=2.3 Hz, 1H), 8.33-8.40 (m, 2H), 8.55 (s, 1H), 8.76 (d, J=2.3 Hz, 1H), 8.89 (d, J=2.3 Hz, 1H), 10.52 (br s, 2H). (m/z)=475 (M+H)$^+$.

Example 37

Synthesis of N-(5-(4-fluoro-3-(trifluoromethyl)benzamido)-2-methylphenyl)thieno[2,3-b]pyrazine-6-carboxamide (32k)

Example 38

Synthesis of N-(5-(2-fluoro-3-(trifluoromethyl)benzamido)-2-methylphenyl)thieno[2,3-b]pyrazine-6-carboxamide (32l)

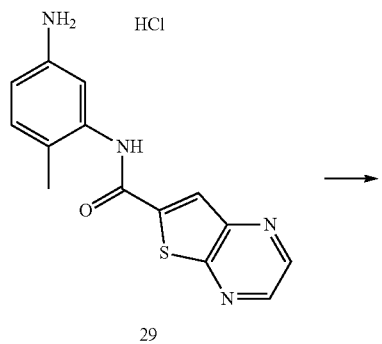

29

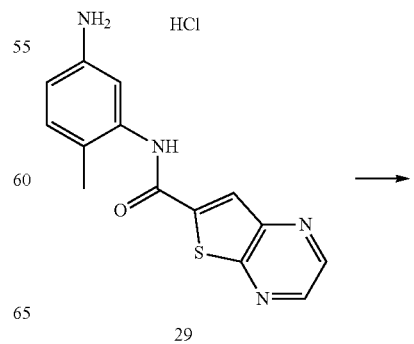

29

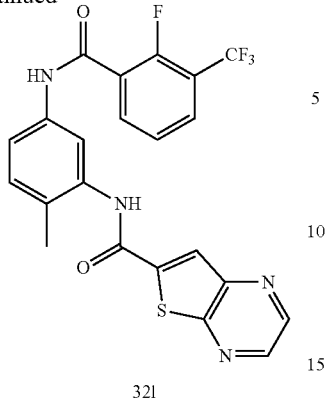

32l

Preparation analogous to general procedure III by using 2-fluoro-3-(trifluoromethyl)benzoicacid (1.5 eq), HATU (1.5 eq), DIPEA (3 eq) in DMF (1 mL). The crude compound was purified by chromatography (20% EtOAc in CH$_2$Cl$_2$) to give the title compound N-(5-(2-fluoro-3-(trifluoromethyl)benzamido)-2-methylphenyl)thieno[2,3-b]pyrazine-6-carboxamide 32l (11 mg, 37%). NMR (400 MHz, DMSO) 2.26 (s, 3H), 7.32 (d, J=8.6 Hz, 1H) 7.52-7.58 (m, 2H), 7.84 (d, J=1.9 Hz, 1H), 7.99 (m, 2H), 8.55 (s, 1H), 8.76 (d, J=2.3 Hz, 1H), 8.88 (d, J=2.3 Hz, 1H), 10.53 (s, 1H), 10.70 (s, 1H). (m/z)=475 (M+H)$^+$.

Example 39

Synthesis of N-(5-(2-fluoro-5-(trifluoromethoxy)benzamido)-2-methylphenyl)thieno[2,3-b]pyrazine-6-carboxamide (32m)

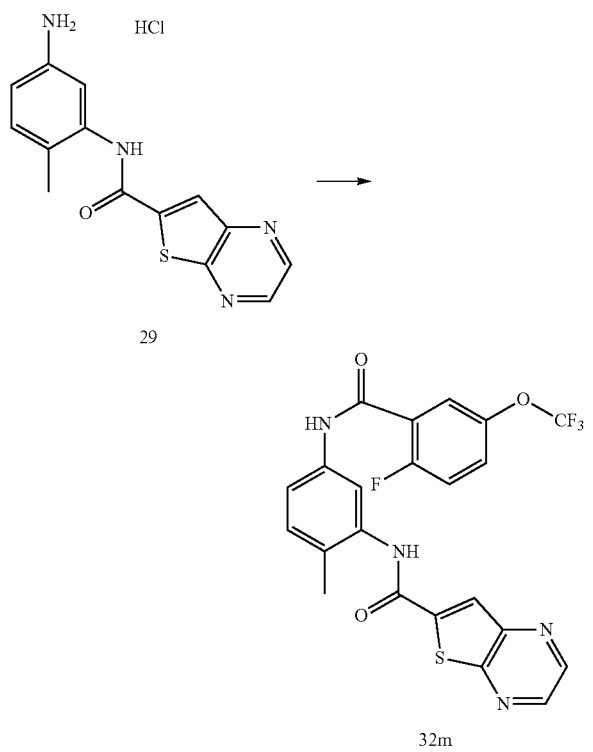

Preparation analogous to general procedure III by using 2-fluoro-5-(trifluoromethoxy)benzoic acid (1.5 eq), HATU (1.5 eq), DIPEA (3 eq) in DMF (1 mL). The crude compound was purified by chromatography (20% EtOAc in CH$_2$Cl$_2$) to give the title compound N-(5-(2-fluoro-5-(trifluoromethoxy)benzamido)-2-methylphenyl)thieno[2,3-b]pyrazine-6-carboxamide 32m (18 mg, 59%). NMR (400 MHz, DMSO) 2.26 (s, 3H), 7.31 (d, J=8.2 Hz, 1H), 7.51-5.57 (m, 2H), 7.63 (m, 1H), 7.71 (m, 1H), 7.83 (d, J=1.9 Hz, 1H), 8.54 (s, 1H), 8.76 (d, J=2.3 Hz, 1H), 8.89 (d, J=2.3 Hz, 1H), 10.52 (s, 1H), 10.62 (s, 1H). (m/z)=491 (M+H)$^+$.

Example 40

Synthesis of N-(5-(3-(3-(2-cyanopropan-2-yl)phenyl)ureido)-2-methylphenyl)thieno[2,3-b]pyrazine-6-carboxamide (40)

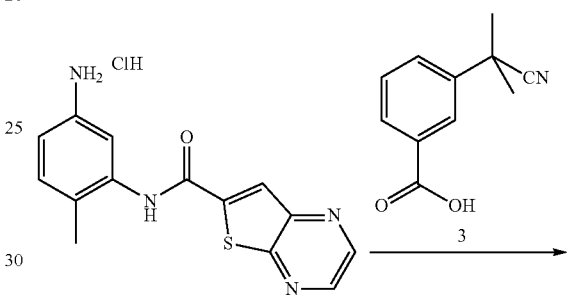

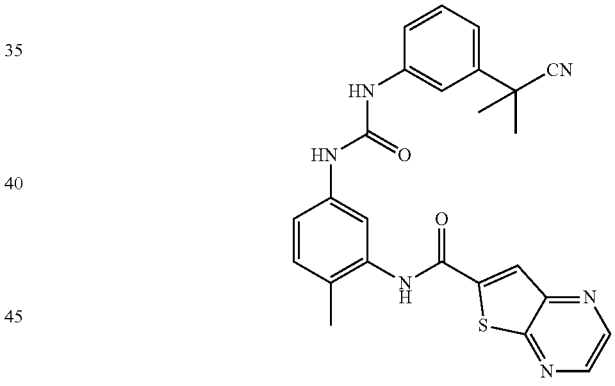

A solution of 3-(2-cyanopropan-2-yl)benzoic acid 3 (50 mg, 0.264 mmol), diphenylphosphoryl azide (0.074 mL, 95 mg, 0.344 mmol) and triethylamine (0.110 mL, 0.793 mmol) in toluene (1 mL) was stirred at 100° C. for 1 h. N-(5-amino-2-methylphenyl)thieno[2,3-b]pyrazine-6-carboxamide hydrochloride 29 (85 mg, 0.264 mmol) in THF (1 mL) was added and stirred at 90° C. for 1 h. Evaporated to dryness and purified by chromatography (0-50% EtOAc in CH$_2$Cl$_2$) to yield the title compound N-(5-(3-(3-(2-cyanopropan-2-yl)phenyl)ureido)-2-methylphenyl)thieno[2,3-b]pyrazine-6-carboxamide 40 (88 mg, 70.8%). NMR (400 MHz, DMSO) 2.21 (s, 3H), 7.11 (m, 1H), 7.23 (m, 2H), 7.33 (t, J=7.8 Hz, 1H), 7.40 (m, 1H), 7.63 (d, J=1.9 Hz, 1H), 7.69 (t, J=1.9 Hz, 1H), 8.53 (s, 1H), 8.73 (s, 1H), 8.76 (d, J=2.3 Hz, 1H), 8.83 (s, 1H), 8.88 (d, J=2.3 Hz, 1H), 10.47 (s, 1H). (m/z)=471 (M+H)$^+$.

Example 41

Step 2: synthesis of 7-bromo-N-(5-(3-(2-cyanopropan-2-yl)benzamido)-2-methylphenyl)thieno[2,3-b]pyrazine-6-carboxamide (42)

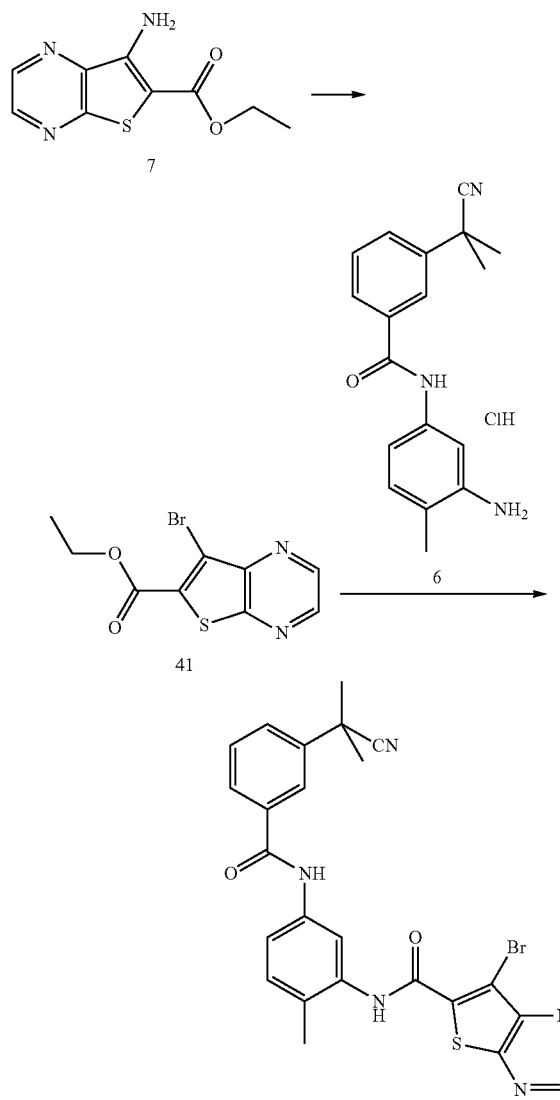

Step 1: synthesis of ethyl 7-bromothieno[3,2-b]pyrazine-6-carboxylate (41)

To a solution of copper(ii) bromide (3.08 g, 13.80 mmol) and tert-butylnitrite (2.172 mL, 16.30 mmol) in Acetonitrile (30 mL) was added Ethyl 7-aminothieno[2,3-b]pyrazine-6-carboxylate 7 (2.8 g, 12.54 mmol) in portions over 2 h and stirred at rt for 2 h. The reaction mixture was poured in 2N HCl solution (60 mL). The resulting precipitate was collected, washed with water. Dissolved in acetonitrile and the black precipitate was filtrated off. Acetonitrile was evaporated to give the crude ethyl 7-bromothieno[3,2-b]pyrazine-6-carboxylate 41 (2.69 g, 74.7%). NMR (400 MHz, CDCl$_3$) 1.48 (t, J=7.0 Hz, 3H), 4.51 (q, J=14.0 and 7.0 Hz, 2H), 8.70 (d, J=2.3 Hz, 1H), 8.84 (d, J=2.3 Hz, 1H). (m/z)=287 and 289 (M+H)$^+$.

Step 2: synthesis of 7-bromo-N-(5-(3-(2-cyanopropan-2-yl)benzamido)-2-methylphenyl)thieno[2,3-b]pyrazine-6-carboxamide (42)

To a solution of N-(3-amino-4-methylphenyl)-3-(2-cyanopropan-2-yl)benzamide hydrochloride 6 (230 mg, 0.697 mmol) in toluene (4 mL) was added trimethylaluminum (1.393 mL, 2.79 mmol). After stirring for 15 min, ethyl 7-bromothieno[3,2-b]pyrazine-6-carboxylate 41 (200 mg, 0.697 mmol) in toluene (4 mL) was added and stirred overnight at 60° C. Quenched with 0.5N NaOH solution and extracted with EtOAc. Organic layer was washed with brine, dried and evaporated. Purification by chromatography (0-10% EtOAc in CH$_2$Cl$_2$) gave the title compound 7-bromo-N-(5-(3-(2-cyanopropan-2-yl)benzamido)-2-methylphenyl)thieno[2,3-b]pyrazine-6-carboxamide 42 (268 mg, 72.0%). NMR (400 MHz, CDCl$_3$) 1.80 (s, 6H), 2.49 (s, 3H), 7.31 (d, J=8.2 Hz, 1H), 7.54 (t, J=7.8 Hz, 1H), 7.74 (m, 1H), 7.80 (d, J=7.8 Hz, 2H), 7.95 (s, 1H), 8.00 (s, 1H), 8.36 (d, J=2.3 Hz, 1H), 8.71 (d, J=2.3 Hz, 1H), 8.84 (d, J=2.3 Hz, 1H), 9.10 (s, 1H). (m/z)=534 and 536 (M+H)$^+$.

Example 42

Synthesis of N-(5-(3-(2-cyanopropan-2-yl)benzamido)-2-methylphenyl)-7-methylthieno[2,3-b]pyrazine-6-carboxamide (43a)

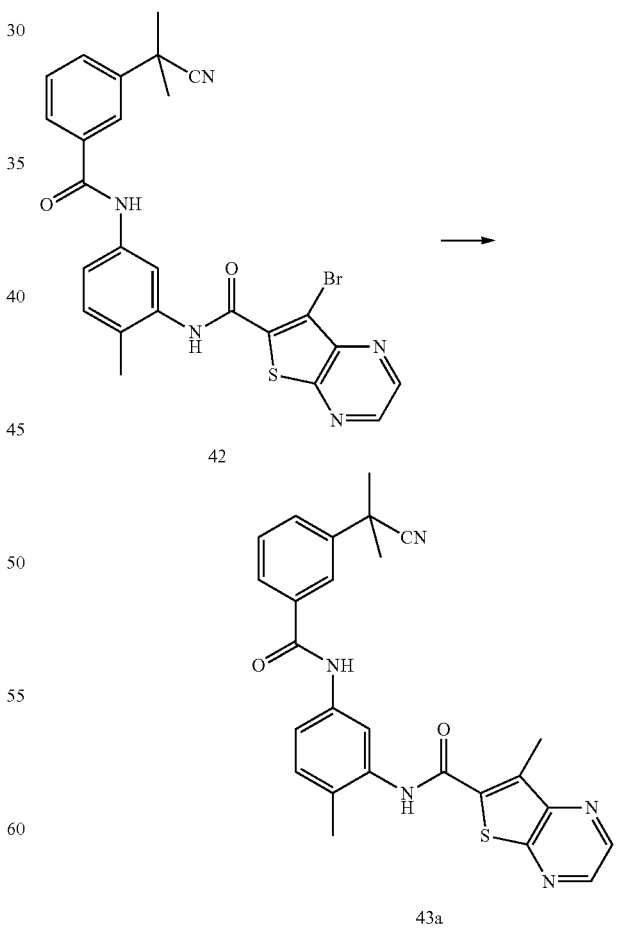

To a solution of 7-bromo-N-(5-(3-(2-cyanopropan-2-yl)benzamido)-2-methylphenyl)thieno[2,3-b]pyrazine-6-carboxamide 42 (20 mg, 0.037 mmol) and 1,1'-bis(diphenylphosphino) ferrocene palladium (ii) chloride, complex with dichloromethane (1.513 mg, 1.871 μmol) in THF (1 mL) was added methylzinc chloride (0.037 mL, 0.075 mmol). The reaction was stirred at 60° C. for 2 h. Water was added and the resulting precipitate was collected. Purification by chromatography (20% EtOAc in CH$_2$Cl$_2$) gave the title compound N-(5-(3-(2-cyanopropan-2-yl)benzamido)-2-methylphenyl)-7-methylthieno[2,3-b]pyrazine-6-carboxamide 43a (4 mg, 22%) NMR (400 MHz, CDCl$_3$) 2.38 (s, 3H), 2.89 (s, 3H), 7.29 (m, 1H), 7.55 (m, 1H), 7.70-7.83 (m, 4H), 7.91 (s, 1H), 7.99 (m, 1H), 8.26 (d, J=1.9 Hz, 1H), 8.64 (d, J=2.3 Hz, 1H), 8.76 (d, J=2.3 Hz, 1H). (m/z)=470 (M+H)$^+$.

Example 43

Synthesis of 7-cyano-N-(5-(3-(2-cyanopropan-2-yl)benzamido)-2-methylphenyl)thieno[2,3-b]pyrazine-6-carboxamide (43b)

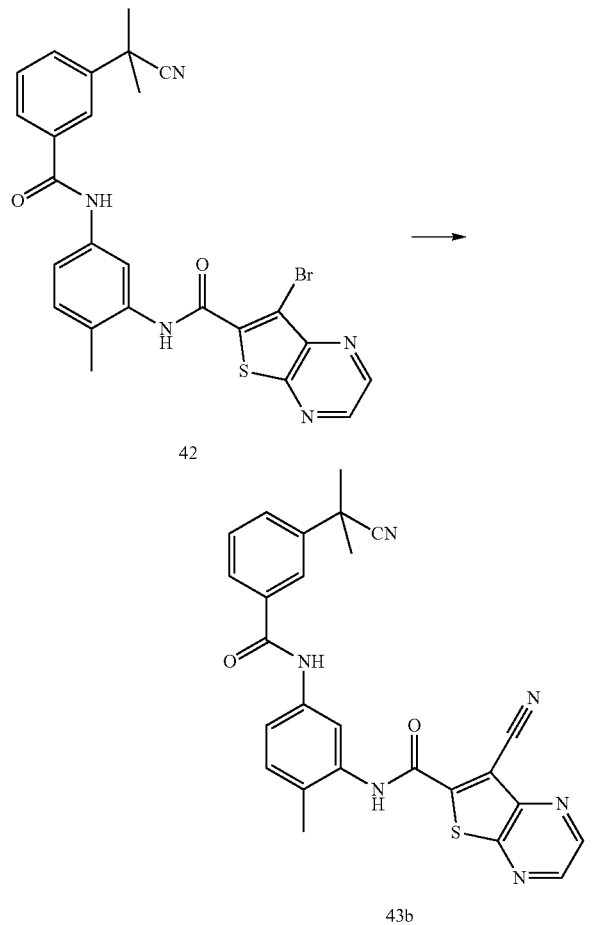 [SMILES: Cc1ccc(NC(=O)c2cccc(C(C)(C)C#N)c2)cc1NC(=O)c1sc2nccnc2c1Br ; Cc1ccc(NC(=O)c2cccc(C(C)(C)C#N)c2)cc1NC(=O)c1sc2nccnc2c1C#N]

42

43b

A solution of 7-bromo-N-(5-(3-(2-cyanopropan-2-yl)benzamido)-2-methylphenyl)thieno[2,3-b]pyrazine-6-carboxamide 42 (20 mg, 0.037 mmol), copper(i) cyanide (3.35 mg, 0.037 mmol) and copper(i) iodide (7.13 mg, 0.037 mmol) in NMP (1 mL) was stirred 10 min at 150° C. in microwave with cooling. Poured in NH$_4$OH solution and extracted with EtOAc. Organic layer was washed with brine, dried and evaporated. Purification by chromatography (20% EtOAc in CH$_2$Cl$_2$) gave the title compound 7-cyano-N-(5-(3-(2-cyanopropan-2-yl)benzamido)-2-methylphenyl)thieno[2,3-b]pyrazine-6-carboxamide 43b (7 mg, 38.9%). NMR (400 MHz, DMSO-d6) 2.31 (s, 3H), 7.33 (d, J=8.2 Hz, 1H), 7.58-7.69 (m, 2H), 7.76 (d, J=7.8 Hz, 1H), 7.94-8.00 (m, 2H), 8.06 (m, 1H), 8.95 (d, J=2.3 Hz, !H), 9.06 (d, J=2.3 Hz, 1H), 10.41 (s, 1H), 10.77 (s, 1H). (m/z)=481 (M+H)$^+$.

Example 44

Synthesis of N-(5-(3-(2-cyanopropan-2-yl)benzamido)-2-methylphenyl)-7-vinylthieno[2,3-b]pyrazine-6-carboxamide (43c) (R=vinyl)

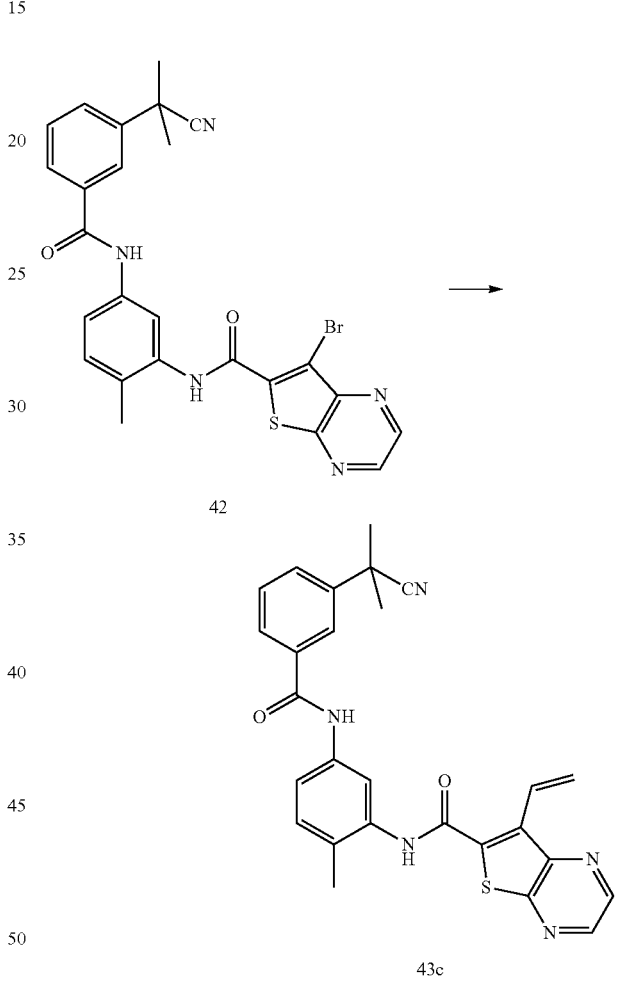

42

43c

A solution of 7-bromo-N-(5-(3-(2-cyanopropan-2-yl)benzamido)-2-methylphenyl)thieno[2,3-b]pyrazine-6-carboxamide 42 (22 mg, 0.041 mmol), bis(triphenylphosphine)palladium(II) chloride (1.445 mg, 2.058 μmol) and tributyl(vinyl)tin (0.024 mL, 0.082 mmol) in toluene (1 mL) was stirred for 30 min at 110° C. in microwave. After filtration, diluted with toluene and washed with water, brine, dried and evaporated. Purification by HPLC gave the title compound N-(5-(3-(2-cyanopropan-2-yl)benzamido)-2-methylphenyl)-7-vinylthieno[2,3-b]pyrazine-6-carboxamide 43c (2 mg, 10.09%). NMR (400 MHz, DMSO-d6) 2.27 (s, 3H), 5.76 (dd, J=12.0 and 2.3 Hz, 1H), 8.85-8.91 (dd, J=17.6 and 1.9 Hz, 1H), 7.28-7.38 (m, 2H), 7.58-7.68 (m, 2H), 7.76 (d, J=7.8 Hz, 1H), 7.91 (d, J=1.9 Hz, 1H), 7.96 (d, J=7.8 Hz, 1H), 8.05 (t, J=1.9

Hz, 1H), 8.80 (d, J=2.3, 1H), 8.94 (d, J=2.3 Hz, 1H), 10.37 (s, 1H), 10.38 (s, 1H). (m/z)=482 (M+H)+.

Example 45

Synthesis of N-(5-(3-(2-cyanopropan-2-yl)benzamido)-2-methylphenyl)-7-(2,2,2-trifluoroacetamido)thieno[2,3-b]pyrazine-6-carboxamide (44)

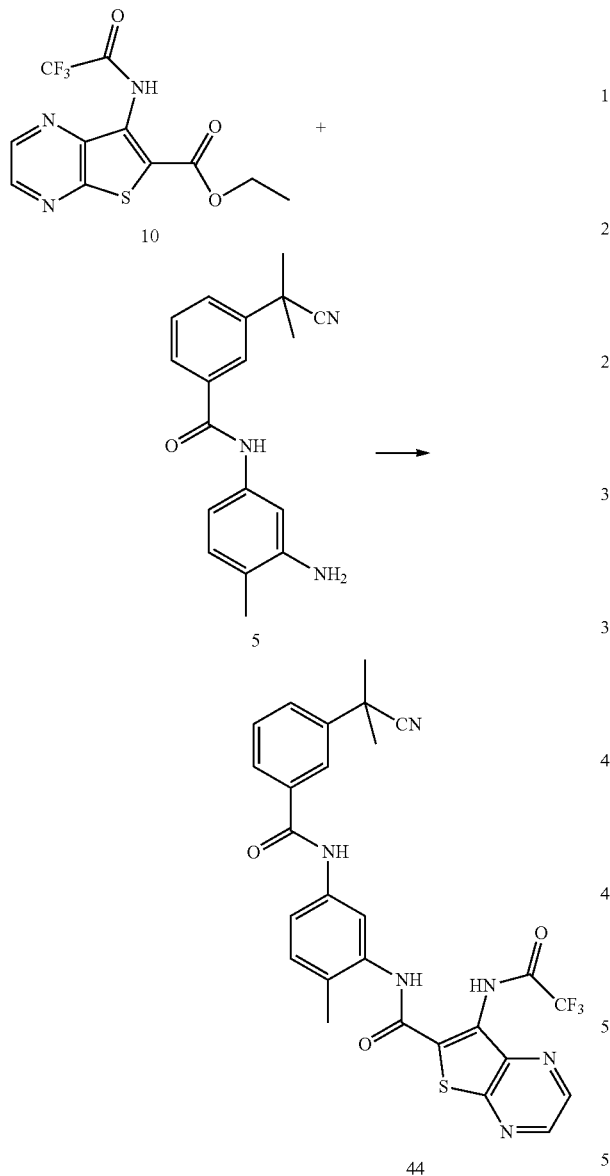

A solution of N-(3-amino-4-methylphenyl)-3-(2-cyanopropan-2-yl)benzamide 5 (25 mg, 0.085 mmol) and trimethylaluminum (0.170 mL, 0.341 mmol) in toluene (1 mL) was stirred for 30 min. Ethyl 7-(2,2,2-trifluoroacetamido)thieno[2,3-b]pyrazine-6-carboxylate 10 (27.2 mg, 0.085 mmol) in toluene (1 mL) was added and stirred overnight at 60° C. Poured in NaHCO3 solution and extracted with EtOAc. Organic layer was washed with brine, dried and evaporated. Purification by chromatography (20->80 ethylacetate in CH2Cl2) gave the title compound N-(5-(3-(2-cyanopropan-2-yl)benzamido)-2-methylphenyl)-7-(2,2,2-trifluoroacetamido)thieno[2,3-b]pyrazine-6-carboxamide 44 (10 mg, 20%). NMR (400 MHz, DMSO-d6) 1.76 (s, 6H), 2.26 (s, 3H), 7.29 (d, J=8.2 Hz, 1H), 7.58-7.66 (m, 2H), 7.76 (d, J=8.2 Hz, 1H), 7.91-7.98 (m, 2H), 8.05 (s, 1H), 8.85 (s, 1H), 8.94 (s, 1H), 10.20 (br s, 1H), 10.38 (s, 1H), 11.80 (br s, 1H). (m/z)=567 (M+H)+.

Example 46

Synthesis of N-(5-(3-(2-cyanopropan-2-yl)benzamido)-2-methylphenyl)-7-(ethylamino)thieno[2,3-b]pyrazine-6-carboxamide (46)

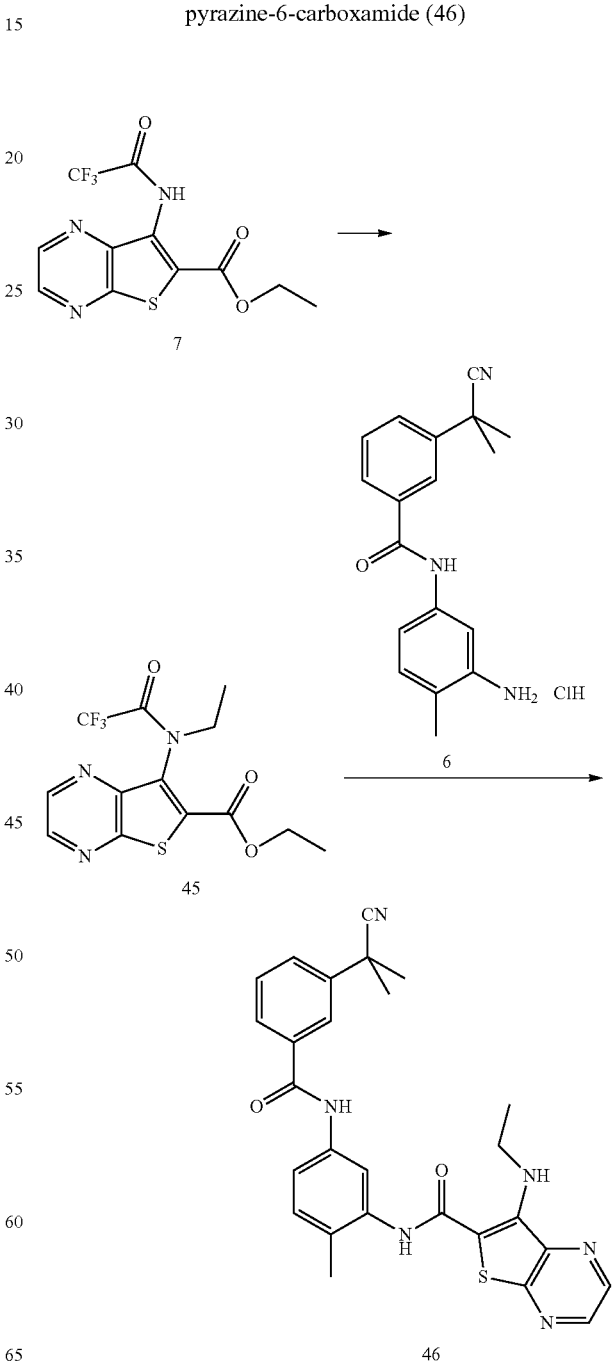

Step 1: synthesis of ethyl 7-(N-ethyl-2,2,2-trifluoro-acetamido)thieno[2,3-b]pyrazine-6-carboxylate (45)

To a solution of Ethyl 7-aminothieno[2,3-b]pyrazine-6-carboxylate 7 (50 mg, 0.157 mmol) and potassium carbonate (43.3 mg, 0.313 mmol) in Acetone (2 mL) was added 1-iodoethane (0.025 mL, 0.313 mmol). The reaction was stirred at 50° C. for 2 h. NH$_4$Cl solution was added and extracted with EtOAc. Organic layer was washed with brine, dried and evaporated. Purification by chromatography (0-5% EtOAc in CH$_2$Cl$_2$) gave ethyl 7-(N-ethyl-2,2,2-trifluoroacetamido)thieno[2,3-b]pyrazine-6-carboxylate 45 (40 mg, 73.5%). (m/z)=348 (M+H)$^+$.

Step 2: synthesis of N-(5-(3-(2-cyanopropan-2-yl)benzamido)-2-methylphenyl)-7-(ethylamino)thieno[2,3-b]pyrazine-6-carboxamide (46)

To a suspension of N-(3-amino-4-methylphenyl)-3-(2-cyanopropan-2-yl)benzamide hydrochloride 6 (40 mg, 0.121 mmol) in toluene (1 mL) was added trimethylaluminum (0.243 mL, 0.485 mmol) and stirred for 15 at rt. 7-(N-ethyl-2,2,2-trifluoroacetamido)thieno[2,3-b]pyrazine-6-carboxylate 45 (42.1 mg, 0.121 mmol) in toluene (1 mL) was added and the reaction was stirred overnight at 70° C. Diluted with EtOAc and washed with seignette salt solution. Organic layer was washed with brine, dried and evaporated. Purification by HPLC gave the title compound N-(5-(3-(2-cyanopropan-2-yl)benzamido)-2-methylphenyl)-7-(ethylamino)thieno[2,3-b]pyrazine-6-carboxamide 46 (3 mg, 4.96%). NMR (400 MHz, DMSO-d6) 1.20 (t, J=7.4 Hz, 3H), 1.75 (s, 6H), 2.22 (s, 1H), 3.98 (q, J=14.0 and 6.5 Hz, 12H), 7.26 (d, J=8.2 Hz, 1H), 7.58-7.64 (m, 2H), 7.75 (d, J=7.8 Hz, 1H), 7.82 (d, J=1.9 Hz, 1H), 7.95 (d, J=7.8 Hz, 1H), 8.04-8.11 (m, 2H), 8.74 (d, J=2.3 Hz, 1H), 8.78 (d, J=2.3 Hz, 1H), 9.53 (s, 1H), 10.32 (s, 1H). (m/z)=499 (M+H)$^+$.

Example 47

Synthesis of 3-(2-cyanopropan-2-yl)-N-(4-methyl-3-(thieno[2,3-b]pyrazin-6-ylmethylamino)phenyl)benzamide (48)

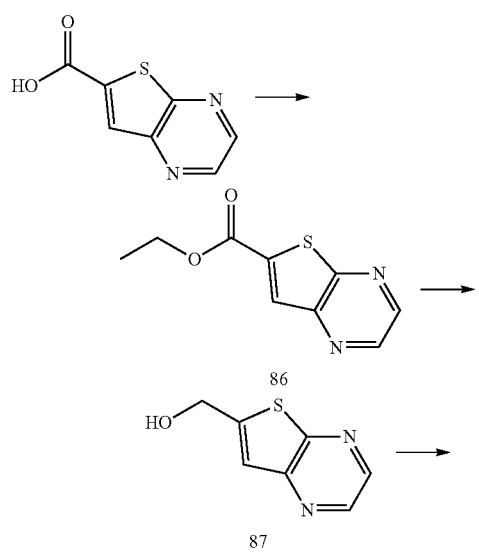

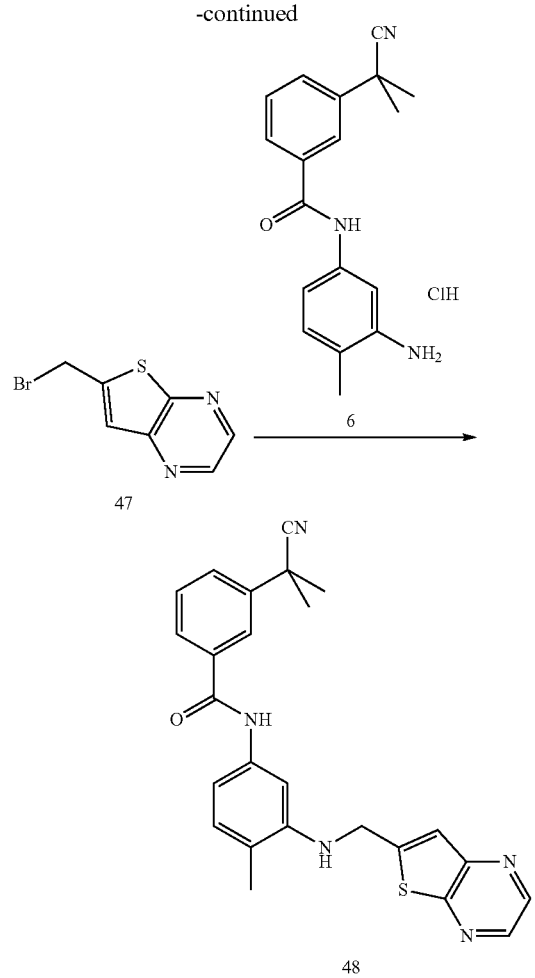

Step 1: synthesis of ethyl thieno[3,2-b]pyrazine-6-carboxylate (86)

Thieno[3,2-b]pyrazine-6-carboxylic acid (2 g, 11.10 mmol) was dissolved in ethanol (30 mL). Concentrate H$_2$SO$_4$ (5.92 mL, 111 mmol) was slowly added. The resulting mixture was heated at 80° C. overnight. The reaction mixture was cooled en neutralized with saturated Na$_2$CO$_3$ solution. The resulting precipitate was collected to give ethyl thieno[3,2-b]pyrazine-6-carboxylate 86 (1.85 g, 80%) as a brown solid. (m/z)=209 (M+H)$^+$.

Step 2: synthesis of thieno[3,2-b]pyrazin-6-ylmethanol (87)

To a solution of ethyl thieno[3,2-b]pyrazine-6-carboxylate 86 (600 mg, 2.88 mmol) in THF (3 mL) and methanol (3 mL) was added sodium borohydride (1.09 g, 28.8 mmol). The reaction was stirred at rt for 30 min. Poured in NH$_4$Cl solution and extracted with EtOAc. Organic layer was washed with brine, dried and evaporated to give the crude thieno[3,2-b]pyrazin-6-ylmethanol 87 (438 mg, 91%) which was used without further purification.

Step 3: synthesis of 6-(bromomethyl)thieno[3,2-b]pyrazine (47)

To a suspension of thieno[3,2-b]pyrazin-6-ylmethanol 87 (408 mg, 2.455 mmol) in CH$_2$Cl$_2$ (8 mL) and THF (8 mL) was added phosphorus tribromide (1/166 mL, 12.27 mmol) and stirred overnight at rt. Water was added, alkalized with 2N NaOH and extracted with EtOAc. Organic layer was washed with NaHCO$_3$ (aq) solution, brine, dried and evaporated. Purification by chromatography (CH$_2$CL$_2$) gave pure 6-(bromomethyl)thieno[3,2-b]pyrazine 47 (356 mg, 63%). NMR (400 MHz, CDCl$_3$) 4.80 (s, 2H), 7.71 (s, 1H), 8.49 (d, J=2.3 Hz, 1H), 8.64 (d, J=2.3 Hz, 1H). (m/z)=229 and 231 (M+H)$^+$.

Step 4: synthesis of 3-(2-cyanopropan-2-yl)-N-(4-methyl-3-(thieno[2,3-b]pyrazin-6-ylmethylamino) phenyl)benzamide (48)

A solution of 6-(bromomethyl)thieno[3,2-b]pyrazine 47 (50 mg, 0.218 mmol), N-(3-amino-4-methylphenyl)-3-(2-cyanopropan-2-yl)benzamide hydrochloride 6 (72 mg, 0.218 mmol) and potassium carbonate (90 mg, 0.655 mmol) in acetonitrile (2 mL) was stirred overnight at 50° C. Water was added and extracted with EtOAc. Organic layer was washed with brine, dried and evaporated. Purification by HPLC gave the title compound 3-(2-cyanopropan-2-yl)-N-(4-methyl-3-(thieno[2,3-b]pyrazin-6-ylmethylamino)phenyl)benzamide 48 (6 mg, 6.23%). NMR (400 MHz, DMSO-d6) 1.71 (s, 6H), 2.16 (s, 3H), 4.72 (d, J=5.5 Hz, 2H), 6.02 (t, J=6.2 Hz, 1H), 6.98 (s, 2H), 7.08 (s, 1H), 7.54 (m, 2H), 7.70 (d, J=7.8 Hz, 1H), 7.83 (d, J=7.8 Hz, 1H), 7.92 (t, J=1.6 Hz, 1H), 8.50 (d, J=2.3 Hz, 1H), 8.66 (d, J=2.3 Hz, 1H), 10.00 (s, 1H). (m/z)=442 (M+H)$^+$.

Example 48

Synthesis of N-(2-methyl-5-(3-(trifluoromethyl)phenylcarbamoyl)phenyl)-thieno[2,3-b]pyrazine-6-carboxamide (51)

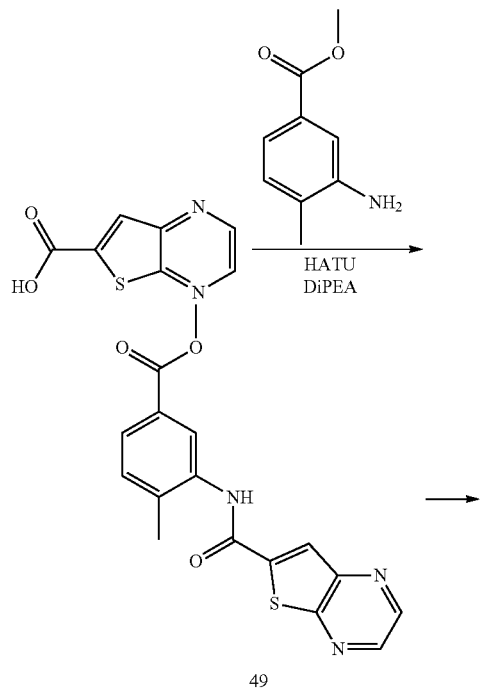

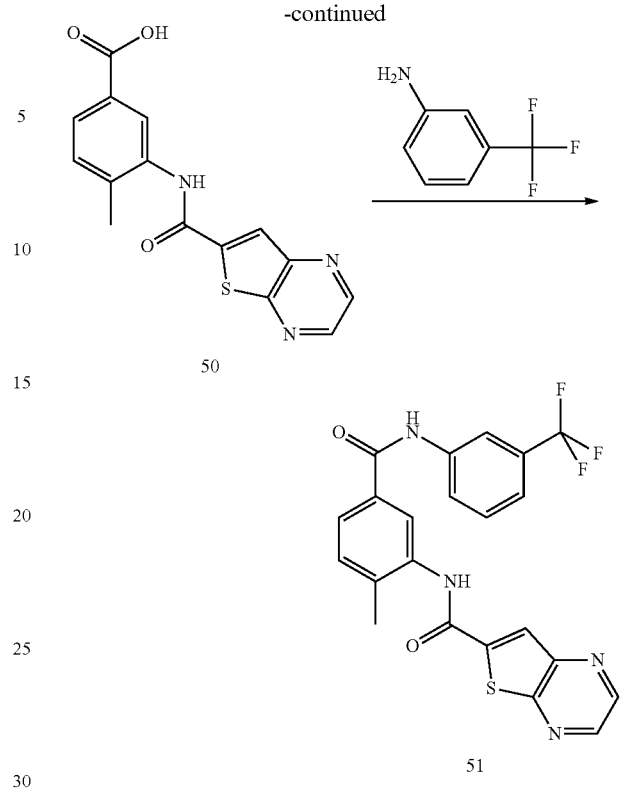

Step 1: synthesis of methyl 4-methyl-3-(thieno[2,3-b]pyrazine-6-carboxamido)benzoate (49)

Thieno[2,3-b]pyrazine-6-carboxylic acid (500 mg, 2.77 mmol) was dissolved in DMF (15 mL). HATU (1266 mg, 3.33 mmol) and DIPEA (2.293 mL, 13.87 mmol) were added and the mixture was stirred for 10 min at rt.
methyl 3-amino-4-methylbenzoate (550 mg, 3.33 mmol) was added and the reaction mixture was heated at 60° C. overnight. The mixture was poured in 3% citric acid solution (100 mL) and extracted with ethyl acetate (2×). Combined organic extracts were dried, and evaporated. Purification by chromatography heptane/EtOAc (6:4) gave methyl 4-methyl-3-(thieno[2,3-b]pyrazine-6-carboxamido)benzoate 49 (260 mg, 52%). (m/z)=328 (M+H)$^+$.

Step 2: synthesis of 4-methyl-3-(thieno[2,3-b]pyrazine-6-carboxamido)benzoic acid (50)

To a solution of methyl 4-methyl-3-(thieno[2,3-b]pyrazine-6-carboxamido)benzoate 49 (480 mg, 1.466 mmol) in ethanol (30 mL) was added 2NaOH (7.33 mL, 14.66 mmol). The mixture was stirred overnight at rt. The mixture was acidified with 2N HCl solution and cooled on ice. the resulting precipitation was collected to give 4-methyl-3-(thieno[2,3-b]pyrazine-6-carboxamido)benzoic acid 50 (310 mg, 67%). NMR (400 MHz, DMSO-d6) 2.36 (s, 3H), 7.46 (d, J=7.8 Hz, 1H), 7.79 (dd, J=7.8 Hz and 1.6 Hz, 1H), 7.96 (d, J=1.6 Hz, 1H), 8.54 (s, 1H), 8.77 (d, J=2.3 Hz, 1H), 8.89 (d, J=2.3 Hz, 1H), 10.57 (s, 1H), 13.01 (br s, 1H). (m/z)=314 (M+H)$^+$.

Step 3: synthesis of N-(2-methyl-5-(3-(trifluoromethyl)phenylcarbamoyl)phenyl)thieno[2,3-b]pyrazine-6-carboxamide (51)

A solution of 4-methyl-3-(thieno[2,3-b]pyrazine-6-carboxamido)benzoic acid 50 (25 mg, 0.080 mmol), 3-aminobenzotrifluoride (9.87 μl, 12.86 mg, 0.080 mmol), TBTU (38.4 mg, 0.120 mmol) and DIPEA (0.039 mL, 0.239 mmol) in DMF (1 mL) under a nitrogen atmosphere was stirred overnight at 40° C. The reaction mixture was poured into 3% citric acid solution. The resulting precipitation was collected and washed with water to give the title compound N-(2-methyl-5-(3-(trifluoromethyl)phenylcarbamoyl)phenyl)thieno[2,3-b]pyrazine-6-carboxamide 51 (19 mg, 53%). NMR (400 MHz, DMSO-d6) 2.38 (s, 3H), 7.46 (d, J=7.4 Hz, 1H), 7.53 (d, J=8.2 Hz, 1H), 7.61 (t, J=7.8 Hz, 1H), 7.90 (dd, J=7.8 and 1.6 Hz, 1H), 8.04 (d, J=1.6 Hz, 1H), 8.09 (d, J=8.6 Hz, 1H), 8.25 (s, 1H), 8.57 (s, 1H), 8.77 (d, J=2.3 Hz, 1H), 8.90 (d, J=2.3 Hz, 1H), 10.55 (s, 1H), 10.66 (s, 1H). (m/z)=457 (M+H)+.

Example 49

Synthesis of 7-amino-2-cyano-N-(5-(3-(2-cyanopropan-2-yl)benzamido)-2-methylphenyl)thieno[2,3-b]pyrazine-6-carboxamide (53)

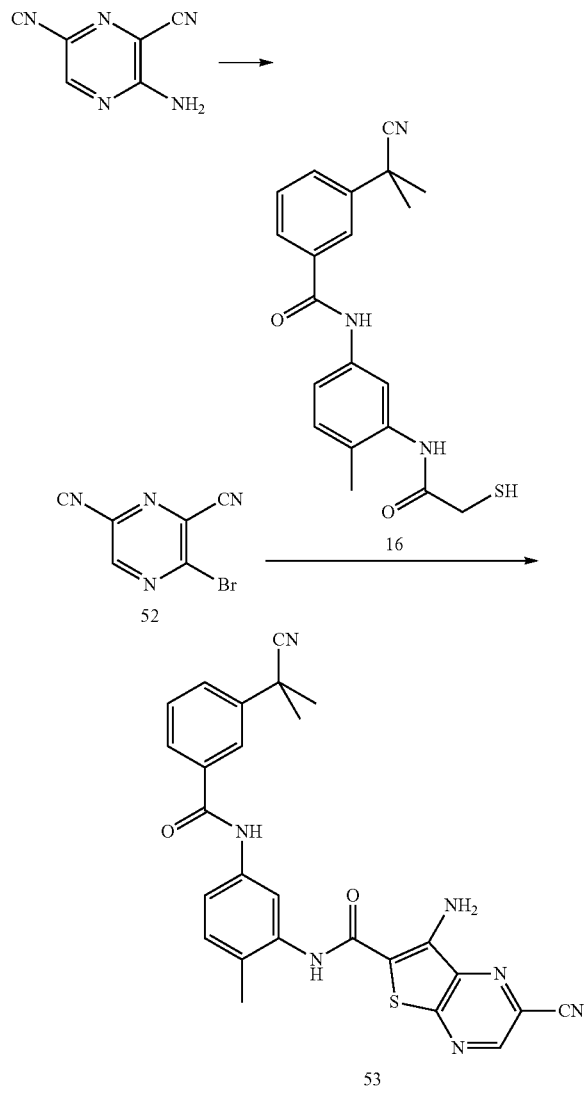

Step 1: synthesis of 3-bromopyrazine-2,6-dicarbonitrile (52)

To a solution of copper(ii) bromide (462 mg, 2.067 mmol) and tert-butylnitrite (0.248 mL, 2.067 mmol) in acetonitrile (5 mL) at 60° C. was added 3-aminopyrazine-2,6-dicarbonitrile (100 mg, 0.689 mmol) in portions (in 2 h). The reaction was stirred for 2 h at 70° C. Quenched with water and extracted with $CH_2Cl_2$. Organic layer was washed with brine, dried and evaporated. Purification by chromatography ($CH_2Cl_2$) gave 3-bromopyrazine-2,6-dicarbonitrile 52 (102 mg, 70.8%). NMR (400 MHz, CDCl3) 8.85 (s, 1H). (m/z)=210 (M+H)+.

Step 2: synthesis of 7-amino-2-cyano-N-(5-(3-(2-cyanopropan-2-yl)benzamido)-2-methylphenyl)thieno[2,3-b]pyrazine-6-carboxamide (53)

A solution of 3-bromopyrazine-2,6-dicarbonitrile 52 (17.06 mg, 0.082 mmol), 3-(2-cyanopropan-2-yl)-N-(3-(2-mercaptoacetamido)-4-methylphenyl)benzamide 16 (0.082 mmol, 30 mg) and potassium carbonate (13.54 mg, 0.098 mmol) in ethanol (1 mL) was stirred at 40° C. for 1 h. Quenched in 2N HCl solution and extracted with $CH_2Cl_2$. Organic layer was washed with brine, dried and evaporated. Purification by chromatography (5-10% EtOAc in $CH_2Cl_2$) gave the title compound 7-amino-2-cyano-N-(5-(3-(2-cyanopropan-2-yl)benzamido)-2-methylphenyl)thieno[2,3-b]pyrazine-6-carboxamide 53 (6 mg, 14.83%). NMR (400 MHz, DMSO-d6) 1.75 (s, 6H), 2.22 (s, 3H), 7.29 (m, 2H), 7.60 (t, J=7.8 Hz, 2H), 7.75 (m, 1H), 7.81 (d, 2.0 Hz, 1H), 7.94 (d, J=Hz, J=7.8 Hz, 1H), 8.05 (t, J=2.0 Hz, 1H), 9.65 (s, 1H), 10.34 (s, 1H). (m/z)=496 (M+H)+.

Example 50

Synthesis of 7-amino-N-(5-(3-(2-cyanopropan-2-yl)benzamido)-2-methylphenyl)-2-(furan-2-yl)thieno[2,3-b]pyrazine-6-carboxamide (60)

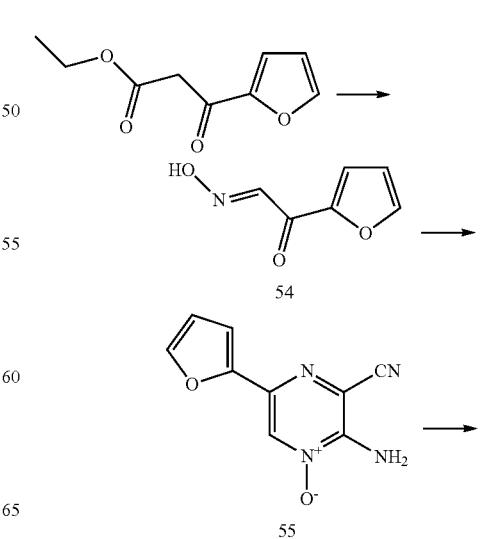

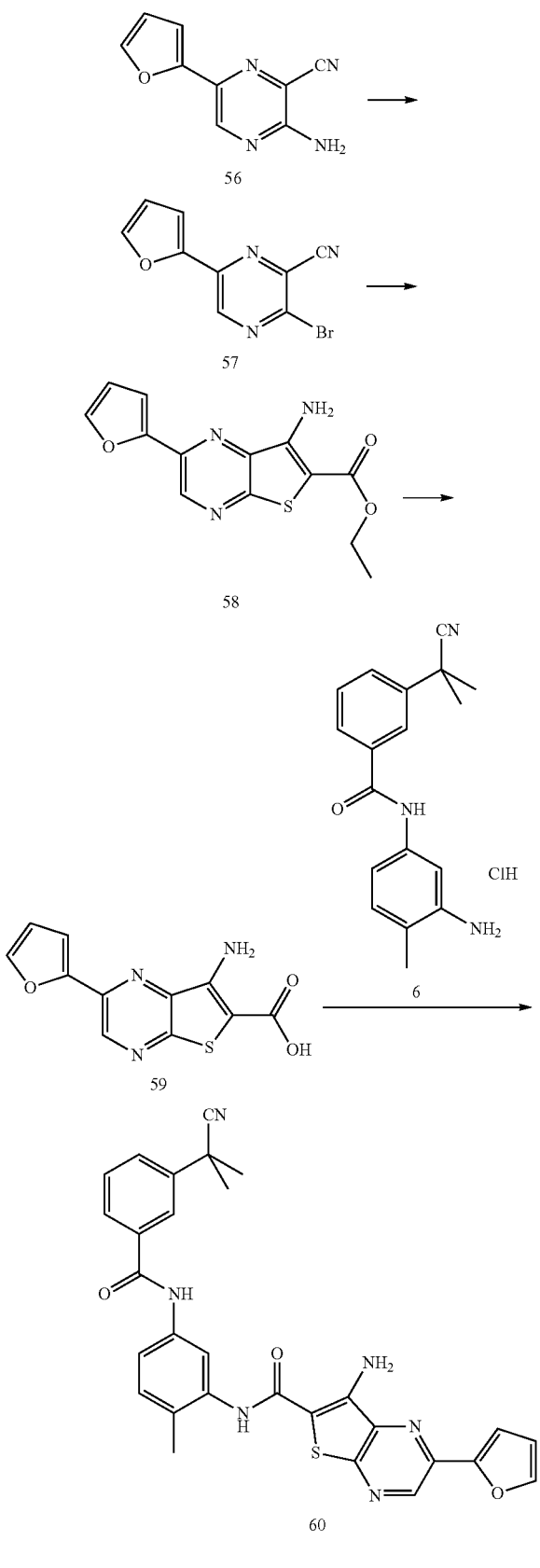

Step 1: synthesis of (E)-2-(furan-2-yl)-2-oxoacetaldehyde oxime (54)

A solution of ethyl 2-(fur-2-oyl)acetate (5.38 g, 29.5 mmol) and potassium hydroxide (2.70 mL, 2.7 g, 48.1 mmol) in water (70 mL) was stirred overnight at rt. sodium nitrite (2.038 g, 29.5 mmol) in water (10 mL) was added and cooled down to 0° C. A solution of 6N sulfuric acid in water (14 mL) was added drop wise and stirred for 15 min (precipitate was formed). Ether was added and the water layer was extracted twice with ether. The combined organic layers were washed with water, dried and evaporated. Crystallization with $CH_2Cl_2$ gave (E)-2-(furan-2-yl)-2-oxoacetaldehyde oxime 54 (2.52 g, 61.3%). NMR (400 MHz, $CDCl_3$) 6.59 (q, J=3.5 and 1.5 Hz, 1H), 7.55 (dd, J=3.5 and 0.8 Hz, 1H), 7.72 (m, 1H), 7.96 (s, 1H), 8.27 (br s, 1H).

Step 2: synthesis of 2-amino-3-cyano-5-(furan-2-yl)pyrazine 1-oxide (55)

A mixture of (E)-2-(furan-2-yl)-2-oxoacetaldehyde oxime 54 (2.52 g, 18.12 mmol) and aminomalononitrile p-toluenesulfonate (4.59 g, 18.12 mmol) in 2-Propanol (35 mL) was stirred at rt for 70 h. Cooled down with ice bad with stirring. The resulting precipitate was collected by filtration, washed with 2-propanol and dried to give 2-amino-3-cyano-5-(furan-2-yl)pyrazine 1-oxide 55 (3.37 g, 92%). NMR (400 MHz, DMSO-d6) 6.65 (m, 1H), 7.10 (m, 1H), 7.83 (m, 1H), 8.09 (br s, 2H), 8.87 (s, 1H).

Step 3: synthesis of 3-amino-6-(furan-2-yl)pyrazine-2-carbonitrile (56)

triethyl phosphite (20 mL, 19.20 g, 116 mmol) was heated to 130° C. and 2-amino-3-cyano-5-(furan-2-yl)pyrazine 1-oxide 55 (3.37 g, 13.34 mmol) was added in portions (±20 min). The reaction was stirred for 1 h, cooled down to 70° C., water (40 mL) was added and stirred for 30 min at 70° C. Cooled down with ice bad and the resulting precipitate was collected, washed with water and dried to give 3-amino-6-(furan-2-yl)pyrazine-2-carbonitrile 56 (2.46 g, 99%). NMR (400 MHz, DMSO-d6) 6.64 (m, 1H), 6.99 (d, J=3.5 Hz, 1H), 7.51 (br s, 1H), 7.80 (m, 1H), 8.70 (s, 1H). (m/z)=187 (M+H)+.

Step 4: synthesis of 3-bromo-6-(furan-2-yl)pyrazine-2-carbonitrile (57)

To a solution of copper(ii) bromide (2.88 g, 12.89 mmol) in DMF (10 mL) at 55° C. was added tert-butylnitrite (3.09 mL, 2.66 g, 25.8 mmol). A solution of 3-amino-6-(furan-2-yl)pyrazine-2-carbonitrile 56 (2.4 g, 12.89 mmol) in DMF (10 mL) was added drop wise (in 30 min). After addition was complete, the reaction was stirred for 20 min. Quenched with 60 mL 3N HCl contain 4 mL concentrated $H_2SO_4$ at −20° C. The resulting precipitate was collected. Purification by chromatography (toluene) gave 3-bromo-6-(furan-2-yl)pyrazine-2-carbonitrile 57 (1.28 g, 39.7%). NMR (400 MHz, $CDCl_3$) 6.63 (q, J=3.5 and 1.5 Hz, 1H), 7.30 (dd, J=3.5 and 0.8 Hz, 1H), 7.66 (dd, J=2.0 and 0.8 Hz, 1H), 8.86 (s, 1H). (m/z)=250 and 252 (M+H)+.

Step 5: synthesis of ethyl 7-amino-2-(furan-2-yl)thieno[2,3-b]pyrazine-6-carboxylate (58)

A solution of 3-bromo-6-(furan-2-yl)pyrazine-2-carbonitrile 57 (1.21 g, 4.84 mmol), ethyl-2-mercaptoacetate (0.587 mL, 0.640 g, 5.32 mmol) and sodium carbonate (0.564 g, 5.32 mmol) in ethanol (20 mL) was stirred 1 h at rt, 1 h at 40° C. and 1 h at 50° C. Cooled down to −10° C., the resulting precipitate was collected, washed with cold ethanol (5 mL) and dried to give ethyl 7-amino-2-(furan-2-yl)thieno[2,3-b]pyrazine-6-carboxylate 58 (1.4 g, 100%). NMR (400 MHz, DMSO-d6) 1.32 (t, J=7.0, 3H), 4.33 (q, J=14.0 and 7.0 Hz, 2H), 6.78 (dd, J=3.5 and 2.0, 1H), 7.05 (br s, 2H), 7.47 (dd, J=3.5 and 0.8 Hz, 1H), 8.00 (dd, J=2.0 and 0.8 Hz, 1H), 9.16 (s, 1H). (m/z)=290 (M+H)$^+$.

Step 6: synthesis of 7-amino-2-(furan-2-yl)thieno[2,3-b]pyrazine-6-carboxylic acid (59)

A suspension of ethyl 7-amino-2-(furan-2-yl)thieno[2,3-b]pyrazine-6-carboxylate 58 (100 mg, 0.346 mmol) and potassium hydroxide (97 mg, 1.728 mmol) in ethanol (5 mL) and water (1 mL) was stirred at 70° C. for 1 h. Quenched in ice cold citric acid solution. The resulting precipitate was collected, washed with water and dried to 7-amino-2-(furan-2-yl)thieno[2,3-b]pyrazine-6-carboxylic acid 59 (66 mg, 73.1%). (m/z)=262 (M+H)$^+$.

Step 7: synthesis of 7-amino-N-(5-(3-(2-cyanopropan-2-yl)benzamido)-2-methylphenyl)-2-(furan-2-yl)thieno[2,3-b]pyrazine-6-carboxamide (60)

A solution of 7-amino-2-(furan-2-yl)thieno[2,3-b]pyrazine-6-carboxylic acid 59 (66 mg, 0.253 mmol), HATU (106 mg, 0.278 mmol) and DIPEA (0.104 mL, 0.632 mmol) in DMF (2 mL) was stirred at rt for 30 min. N-(3-amino-4-methylphenyl)-3-(2-cyanopropan-2-yl)benzamide hydrochloride 6 (83 mg, 0.253 mmol) was added and stirred overnight at 80° C. Quenched in 2N HCl solution, the resulting precipitate was collected and dried. Purification by HPLC gave the title compound 7-amino-N-(5-(3-(2-cyanopropan-2-yl)benzamido)-2-methylphenyl)-2-(furan-2-yl)thieno[2,3-b]pyrazine-6-carboxamide 60 (47 mg, 34%). NMR (400 MHz, DMSO-d6) 1.76 (s, 6H), 2.23 (s, 3H), 6.79 (dd, J=1.6 and 3.5 Hz, 1H), 7.01 (s, 2H), 7.27 (d, J=8.2 Hz, 1H), 7.46 (d, J=3.5 Hz, 1H), 7.60 (t, J=7.8 Hz, 2H), 7.75 (m, 1H), 7.82 (d, J=1.9 Hz, 1H), 7.95 (m, 1H), 8.01 (m, 1H), 8.05 (m, 1H), 9.16 (s, 1H), 9.48 (s, 1H), 10.33 (s, 1H). (m/z)=537 (M+H)$^+$.

Example 51

Synthesis of N-(2-bromo-5-(3-(2-cyanopropan-2-yl)benzamido)phenyl)thieno[2,3-b]pyrazine-6-carboxamide (64)

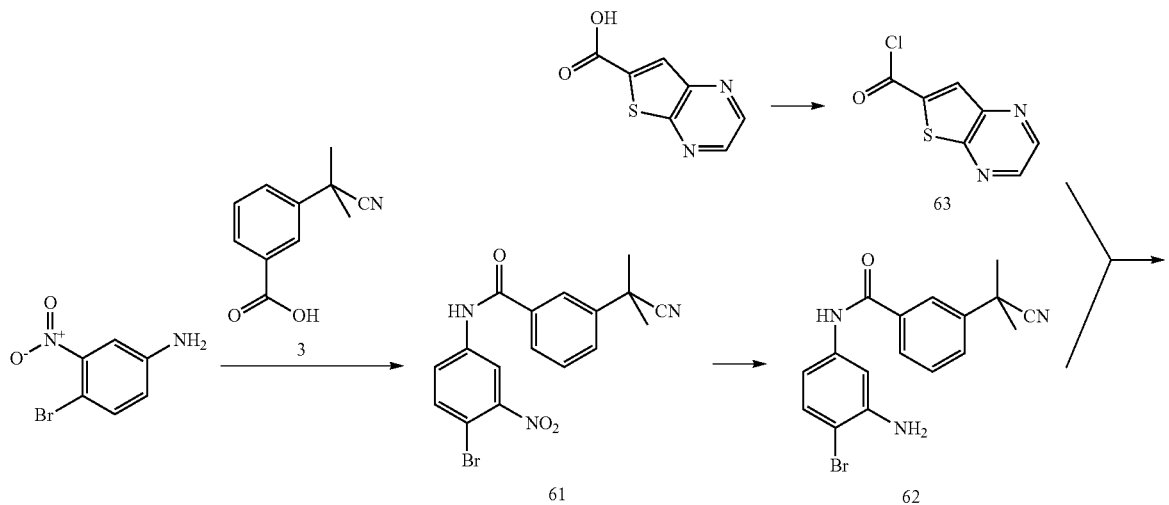

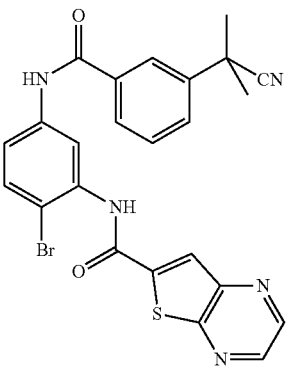

Step 1: synthesis of N-(4-bromo-3-nitrophenyl)-3-(2-cyanopropan-2-yl)benzamide (61)

A solution of 3-(2-cyanopropan-2-yl)benzoic acid 3 (436 mg, 2.304 mmol), HATU (1.051 g, 2.76 mmol) and DIPEA (0.762 mL, 4.61 mmol) in DMF (9 mL) was stirred 15 min at rt. 4-bromo-3-nitroaniline (200 mg, 0.922 mmol) was added and stirred overnight at 60° C. The reaction mixture was cooled to rt and extracted with $CH_2Cl_2$. Organic layer was washed (3×) with water, dried and evaporated. Purification by chromatography heptane:EtOAc (1:1) gave N-(4-bromo-3-nitrophenyl)-3-(2-cyanopropan-2-yl)benzamide 61 (894 mg, 89%). (m/z)=388 and 390 $(M+H)^+$.

Step 2: synthesis of N-(3-amino-4-bromophenyl)-3-(2-cyanopropan-2-yl)benzamide (62)

To a mixture of N-(4-bromo-3-nitrophenyl)-3-(2-cyanopropan-2-yl)benzamide 61 (400 mg, 1.030 mmol) and ZINC (1.011 g, 15.46 mmol) in THF (10 mL) at −5° C., acetic acid (1.180 mL, 20.61 mmol) was added. The reaction mixture was stirred at −5° C. for 30 min and 1 h at rt. Ethanol and acetonitrile were added and filtered off over filter. To the filtrate was added $NaHCO_3$ solution and extracted with $CH_2Cl_2$. Organic layer was dried and evaporated to give crude N-(3-amino-4-bromophenyl)-3-(2-cyanopropan-2-yl)benzamide 62 (319 mg, 86%). (m/z)=358 and 360 $(M+H)^+$.

Step 3: synthesis of thieno[2,3-b]pyrazine-6-carbonyl chloride (63)

A solution of thieno[2,3-b]pyrazine-6-carboxylic acid (400 mg, 2.220 mmol) in thionyl chloride (1.6 mL, 22.20 mmol) was heated to 80° C. for 2 h. Concentrated to dryness and coevaporated with toluene to give thieno[2,3-b]pyrazine-6-carbonyl chloride 63 (441 mg, 100%).

Step 4: synthesis of N-(2-bromo-5-(3-(2-cyanopropan-2-yl)benzamido)phenyl)thieno[2,3-b]pyrazine-6-carboxamide (64)

A mixture of N-(3-amino-4-bromophenyl)-3-(2-cyanopropan-2-yl) 62 (215 mg, 0.600 mmol) and thieno[2,3-b]pyrazine-6-carbonyl chloride 63 (238 mg, 1.2 mmol) in dioxane (1 mL) was stirred for 2 h in microwave at 100° C. The reaction mixture was poured out in water, precipitate filtered off and washed with water and dried. Crystallization with acetonitrile gave crude compound 64 (340 mg, 109%). A sample of compound 64 was purified by HPLC to give the title compound N-(2-bromo-5-(3-(2-cyanopropan-2-yl)benzamido)phenyl)thieno[2,3-b]pyrazine-6-carboxamide 64. NMR (400 MHz, DMSO-d6) 1.76 (s, 6H), 7.62 (t, d=7.8 Hz, 1H), 7.72-7.80 (m, 3H), 7.96 (d, J=7.8 Hz, 1H), 8.06 (m, 2H), 8.57 (s, 1H), 8.77 (d, J=2.3 Hz, 1H), 8.90 (d, J=2.3 Hz, 1H), 10.55 (s, 1H), 10.76 (s, 1H).

Example 52

Synthesis of N-(2-cyano-5-(3-(2-cyanopropan-2-yl)benzamido)phenyl)thieno[2,3-b]pyrazine-6-carboxamide (65)

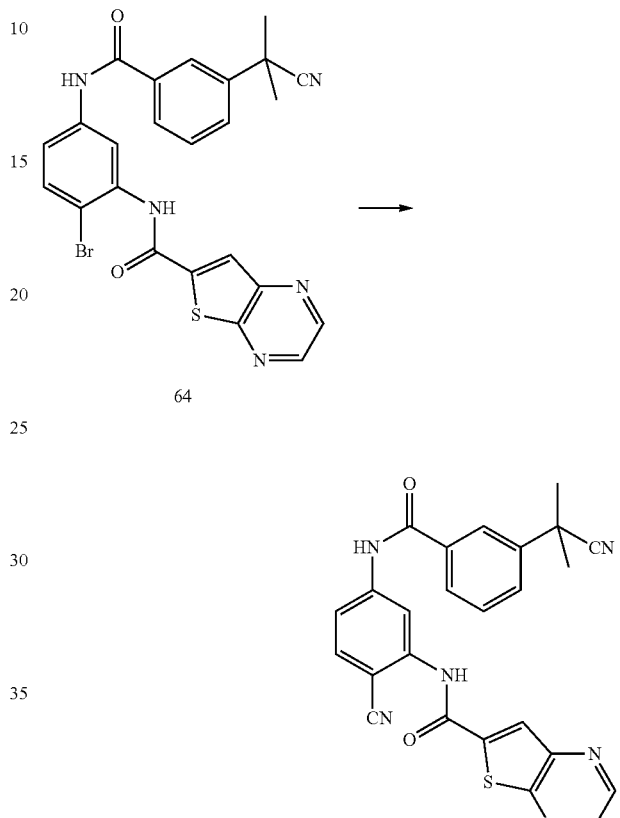

A solution of N-(2-bromo-5-(3-(2-cyanopropan-2-yl)benzamido)phenyl)thieno[2,3-b]pyrazine-6-carboxamide 64 (80 mg, 0.154 mmol), copper(I) iodide (29.3 mg, 0.154 mmol) and copper(I) cyanide (13.77 mg, 0.154 mmol) in NMP (1.5 mL) was stirred 10 min in microwave at 150° C. with cooling on. The reaction mixture was poured out in $NH_4Cl$ solution and extracted with EtOAc. Organic layer was washed (3×) with water, brine, dried, and evaporated. Purification by chromatography $CH_2Cl_2$: MeOH (9:1) and then crystallization in acetonitrile gave the title compound N-(2-cyano-5-(3-(2-cyanopropan-2-yl)benzamido)phenyl)thieno[2,3-b]pyrazine-6-carboxamide 65 (12 mg, 16%). NMR (400 MHz, DMSO-d6) 1.76 (s, 6H), 7.64 (t, d=7.8 Hz, 1H), 7.80 (d, J=7.8 Hz, 1H), 7.87 (dd, J=8.6 and 1.9 Hz, 1H), 7.92-7.99 (m, 2H), 8.05 (m, 1H), 8.21 (d, J=1.9 Hz, 1H), 8.58 (s, 1H), 8.79 (d, J=2.3 Hz, 1H), 8.91 (d, J=2.3 Hz, 1H), 10.82 (s, 1H), 11.25 (s, 1H). (m/z)=467 $(M+H)^+$.

Example 53

Synthesis of N-(2-methyl-5-(3-(trifluoromethyl)benzamido)phenyl)-2-(pyridin-3-yl)thieno[2,3-b]pyrazine-6-carboxamide (69)

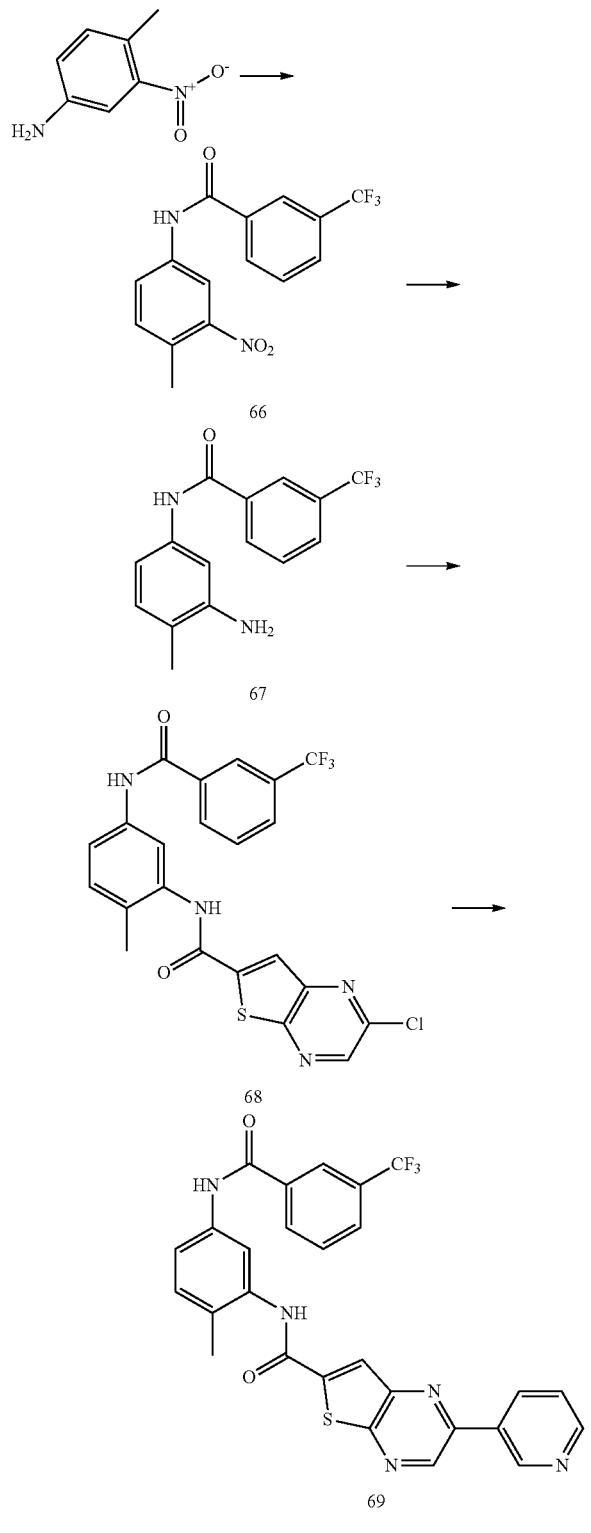

Step 1: synthesis of N-(4-methyl-3-nitrophenyl)-3-(trifluoromethyl)benzamide (66)

A solution of 3-(trifluoromethyl)benzoic acid (8 g, 42.1 mmol), HATU (19.20 g, 50.5 mmol) and DIPEA (13.91 mL, 84 mmol) in DMF (350 mL) was stirred for 15 min at rt. 4-methyl-3-nitroaniline (6.40 g, 42.1 mmol) was added and stirred overnight at 60° C. After cooling to room temperature the reaction was quenched with $H_2O$. After stirring for 10 minutes the resulting precipitate was collected and washed with water to give compound N-(4-methyl-3-nitrophenyl)-3-(trifluoromethyl)benzamide 66 (12 g, 88%). (m/z)=325 (M+H)$^+$.

Step 2: synthesis of N-(3-amino-4-methylphenyl)-3-(trifluoromethyl)benzamide (67)

To a mixture of N-(4-methyl-3-nitrophenyl)-3-(trifluoromethyl)benzamide 66 (12 g, 37.0 mmol) and palladium on activated carbon (0.438 g, 3.70 mmol) in methanol (800 mL), hydrogen (gas) was bubbled through for 2 h. Excess of Pd/C (5 g) was added and stirred for additional 2 h. Filtered over decalite and concentrated to give N-(3-amino-4-methylphenyl)-3-(trifluoromethyl)benzamide 67 (12 g, 88%). (m/z)=295 (M+H)$^+$.

Step 3: synthesis of 2-chloro-N-(2-methyl-5-(3-(trifluoromethyl)benzamido)phenyl)thieno[2,3-b]pyrazine-6-carboxamide (68)

A solution of 2-chlorothieno[3,2-b]pyrazine-6-carboxylic acid 23 (219 mg, 1.019 mmol), HATU (465 mg, 1.223 mmol) and DIPEA (0.337 mL, 2.039 mmol) in DMF (6 mL) was stirred for 15 min at rt. N-(3-amino-4-methylphenyl)-3-(trifluoromethyl)benzamide 67 (300 mg, 1.019 mmol) was added and stirred overnight at rt and overnight at 60° C. The reaction mixture was poured out in 3% citric acid solution and the resulting precipitate was collected and washed with water to give compound 2-chloro-N-(2-methyl-5-(3-(trifluoromethyl)benzamido)phenyl)thieno[2,3-b]pyrazine-6-carboxamide 68 (389 mg, 78%). (m/z)=491 (M+H)$^+$.

Step 4: synthesis of N-(2-methyl-5-(3-(trifluoromethyl)benzamido)phenyl)-2-(pyridin-3-yl)thieno[2,3-b]pyrazine-6-carboxamide (69)

A mixture of 2-chloro-N-(2-methyl-5-(3-(trifluoromethyl)benzamido)phenyl)thieno[2,3-b]pyrazine-6-carboxamide 68 (100 mg, 0.204 mmol), pyridine-3-boronic acid (37.6 mg, 0.306 mmol), potassium phosphate, tribasic (86 mg, 0.407 mmol), tris(dibenzylideneacetone)dipalladium(0) (9.33 mg, 10.19 µmol) and 2-dicyclohexylphosphino-2',4',6'-triisopropylbiphenyl (9.71 mg, 0.020 mmol) in butane-2-ol was stirred was stirred at 100° C. for 30 min in microwave. Water was added and extracted with EtOAc. Organic layer was washed with water, brine, dried and evaporated. Crystallization with acetonitrile gave the title compound N-(2-methyl-5-(3-(trifluoromethyl)benzamido)phenyl)-2-(pyridin-3-yl)thieno[2,3-b]pyrazine-6-carboxamide 69 (10 mg, 9%). NMR (400 MHz, DMSO-d6) 2.29 (s, 3H), 7.33 (d, J=8.6 Hz, 1H), 7.65 (m, 2H), 7.80 (t, J=7.8 Hz, 1H), 7.92 (d, J=2.0 Hz, 1H), 7.98 (d, J=8.2 Hz, 1H), 8.28 (d, J=7.8 Hz, 1H), 8.32 (s, 1H), 8.61 (s, 1H), 8.63 (t, J=1.6 Hz, 1H), 8.76 (dd, J=4.7 Hz and 1.6 Hz, 1H), 9.43 (d, J=2.0 Hz, 1H), 9.46 (s, 1H), 10.54 (s, 1H), 10.55 (s, 1H). (m/z)=535 (M+H)$^+$.

Example 54

Synthesis of 7-amino-N-(2-methyl-5-(3-(trifluoromethyl)benzamido)phenyl)thieno[2,3-b]pyrazine-6-carboxamide (70)

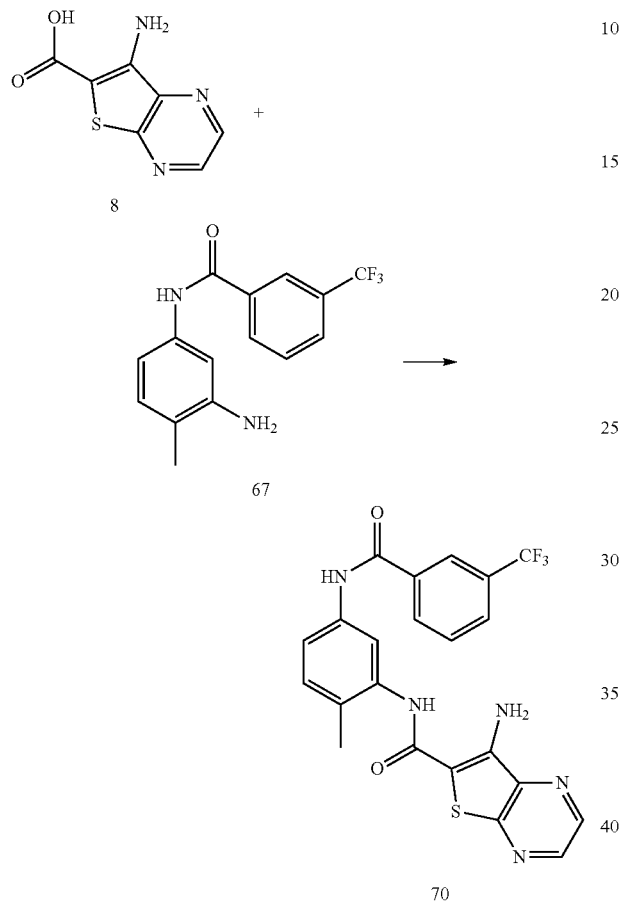

A solution of 7-aminothieno[2,3-b]pyrazine-6-carboxylic acid 8 (32 mg, 0.164 mmol), HATU (74.8 mg, 0.197 mmol) and DIPEA (0.054 mL, 0.328 mmol) in DMF (2 mL) was stirred for 15 at rt. N-(3-amino-4-methylphenyl)-3-(trifluoromethyl)benzamide 67 (48.2 mg, 0.164 mmol) was added and stirred overnight at 80° C. The reaction mixture was poured in cold citric acid solution and the resulting precipitate was collected. Purification by HPLC gave the title compound 7-amino-N-(2-methyl-5-(3-(trifluoromethyl)benzamido)phenyl)thieno[2,3-b]pyrazine-6-carboxamide 70 (14 mg, 18%). NMR (400 MHz, DMSO-d6) 2.23 (s, 3H), 7.07 (s, 2H), 7.28 (d, J=8.2 Hz, 1H), 7.62 (dd, J=8.2 Hz and 2.0 Hz, 1H), 7.79 (t, J=7.8 Hz, 1H), 7.84 (d, J=2.0 Hz, 1H), 7.97 (d, J=7.8 Hz, 1H), 8.28 (d, J=8.2 Hz, 1H), 8.31 (s, 1H), 8.78 (dd, J=5.1 Hz and 2.3 Hz, 2H), 9.48 (s, 1H), 10.49 (s, 1H). (m/z)=472 (M+H)+.

Example 55

Synthesis of N-(5-(3-(2-cyanopropan-2-yl)benzamido)-2,4-difluorophenyl)thieno[2,3-b]pyrazine-6-carboxamide (74)

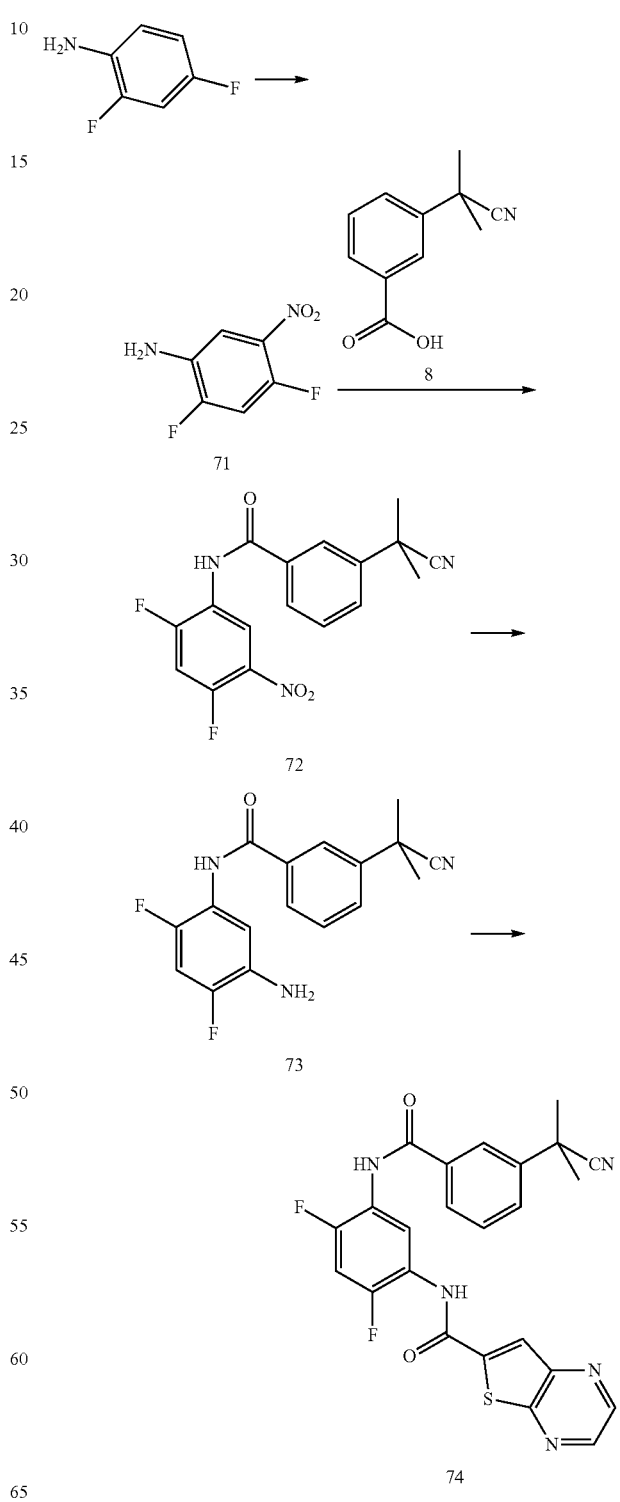

Step 1: synthesis of 2,4-difluoro-5-nitroaniline (71)

To a solution of 2,4-difluoroaniline (0.394 mL, 3.87 mmol) in concentrated sulfuric acid (5 mL, 94 mmol) at 0° C. was added drop wise nitric acid (0.272 mL, 375 mg, 3.87 mmol) in 20 min. The reaction was stirred under 5° C. for 30 min. The reaction mixture was poured in ice cold water and extracted with ether. Organic layer was washed with saturated NaHCO₃ solution, dried and evaporated to give 2,4-difluoro-5-nitroaniline 71 (467 mg, 69.3%). NMR (400 MHz, CDCl₃) 3.91 (br s, 2H), 6.98 (t, J=10.2 Hz, 1H), 7.51 (dd, J=8.6 Hz and 7.0 Hz, 1H).

Step 2: synthesis of 3-(2-cyanopropan-2-yl)-N-(2,4-difluoro-5-nitrophenyl)benzamide (72)

A solution of 7-aminothieno[2,3-b]pyrazine-6-carboxylic acid 8 (179 mg, 0.948 mmol), HATU and DIPEA (0.313 mL, 1.895 mmol) in DMF (6 mL) was stirred at rt for 15 min. 2,4-difluoro-5-nitroaniline 71 (165 mg, 0.948 mmol) was added and stirred overnight at 60° C. Citric acid solution (3%) was added and extracted with EtOAc. Organic layer was washed twice water, brine, dried and evaporated. Purification by chromatography (20% EtOAc in heptane) gave 3-(2-cyanopropan-2-yl)-N-(2,4-difluoro-5-nitrophenyl)benzamide 72 (157 mg, 48%). (m/z)=346 (M+H)⁺.

Step 3: synthesis of N-(5-amino-2,4-difluorophenyl)-3-(2-cyanopropan-2-yl)benzamide (73)

To a mixture of 3-(2-cyanopropan-2-yl)-N-(2,4-difluoro-5-nitrophenyl)benzamide 72 (155 mg, 0.449 mmol) and zinc (440 mg, 6.73 mmol) in THF (5 mL) at −5° C., acetic acid (0.514 mL, 539 mg, 8.98 mmol) was added. The reaction was stirred 30 min at −5° C. and 1 h at rt. Ethanol and acetonitrile were added and filtrated. The filtrate was diluted with CH₂Cl₂ and washed with saturated NaHCO₃ solution to give N-(5-amino-2,4-difluorophenyl)-3-(2-cyanopropan-2-yl)benzamide 73 (100 mg, 70%). (m/z)=316 (M+H)⁺.

Step 4: synthesis of N-(5-(3-(2-cyanopropan-2-yl)benzamido)-2,4-difluorophenyl)thieno[2,3-b]pyrazine-6-carboxamide (74)

A mixture of thieno[2,3-b]pyrazine-6-carboxylic acid (57.1 mg, 0.317 mmol), HATU (145 mg, 0.381 mmol) and DIPEA (0.105 mL, 0.634 mmol) in DMF (3 mL) was stirred for 15 min. N-(5-amino-2,4-difluorophenyl)-3-(2-cyanopropan-2-yl)benzamide 73 (100 mg, 0.317 mmol) was added and stirred for 2 h at 80° C. Citric acid solution (3%) was added and the resulting precipitate was collected. Purification by HPLC gave the title compound N-(5-(3-(2-cyanopropan-2-yl)benzamido)-2,4-difluorophenyl)thieno[2,3-b]pyrazine-6-carboxamide 74 (31 mg, 20%). NMR (400 MHz, DMSO-d6) 1.76 (s, 6H), 7.61 (m, 2H), 7.79 (m, 1H), 7.85 (t, J=7.8 Hz, 1H), 7.97 (d, J=7.8 Hz, 1H), 8.10 (t, J=2.0 Hz, 1H), 8.56 (s, 1H), 8.77 (d, J=2.3 Hz, 1H), 8.89 (d, J=2.3 Hz, 1H), 10.35 (s, 1H), 10.80 (br s, 1H). (m/z)=478 (M+H)⁺.

Example 56

Synthesis of (E)-N-(5-(3-(2-cyanopropan-2-yl)benzamido)-2-methylphenyl)thieno[2,3-b]pyrazine-6-carbimidoyl cyanide (79)

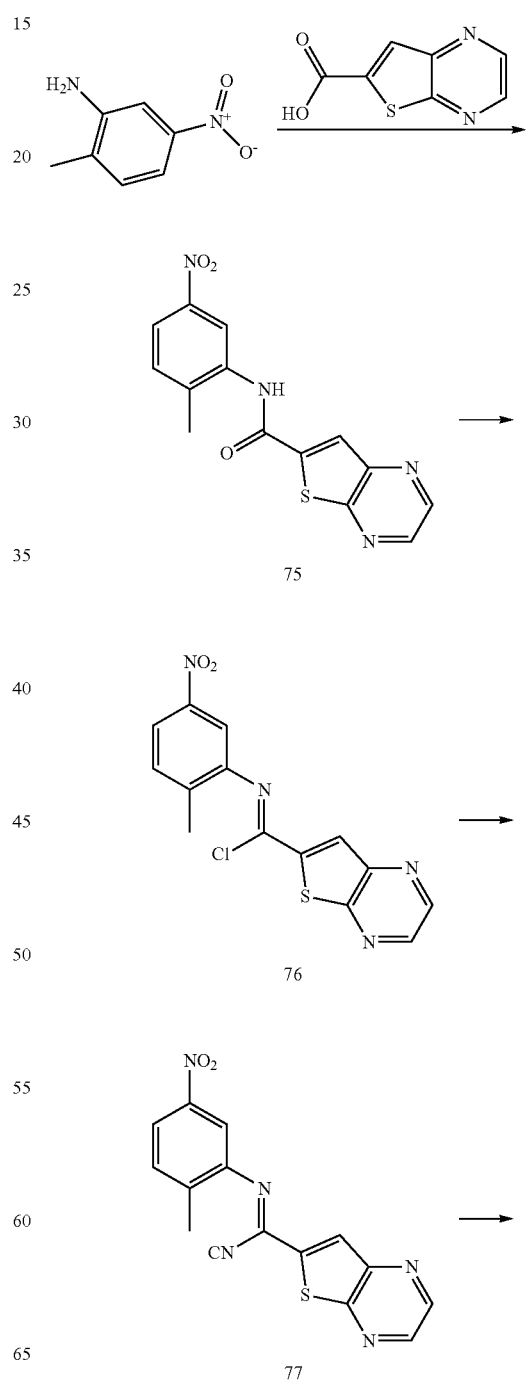

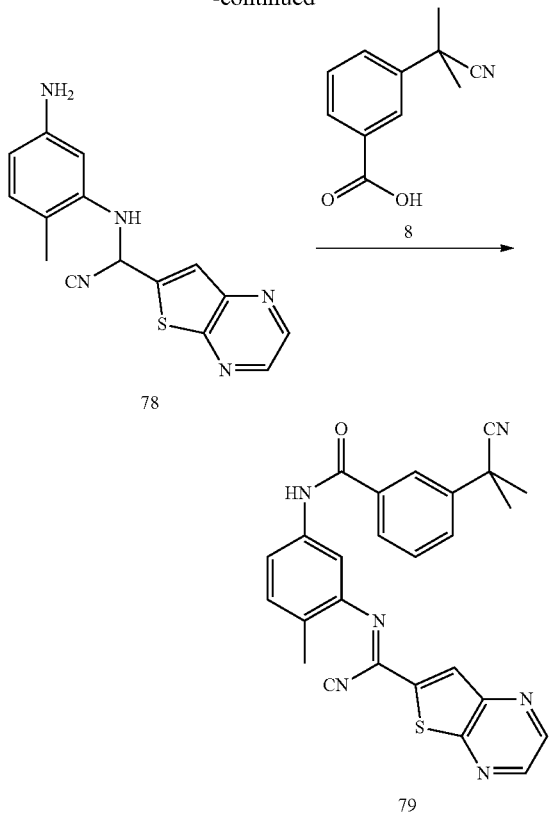

Step 1: synthesis of N-(2-methyl-5-nitrophenyl) thieno[2,3-b]pyrazine-6-carboxamide (75)

A solution of thieno[2,3-b]pyrazine-6-carboxylic acid (250 mg, 1.387 mmol), HATU (633 mg, 1.665 mmol) and DIPEA (0.459 mL, 2.77 mmol) in DMF (5 mL) was stirred for 15 min. 2-methyl-5-nitroaniline (211 mg, 1.387 mmol) was added and stirred at 60° C. for 4 h. Quenched in citric acid solution and the resulting precipitate was collected to give N-(2-methyl-5-nitrophenyl)thieno[2,3-b]pyrazine-6-carboxamide 75 (400 mg, 92%). (m/z)=315 (M+H)$^+$.

Step 2: synthesis of (Z)—N-(2-methyl-5-nitrophenyl)thieno[2,3-b]pyrazine-6-carbimidoyl chloride (76)

A solution of N-(2-methyl-5-nitrophenyl)thieno[2,3-b]pyrazine-6-carboxamide 75 (400 mg, 1.273 mmol) in phosphorus oxychloride (15 mL, 161 mmol) was stirred at 105° C. for 7 h. POCl$_3$ was evaporated to dryness and co evaporated with toluene. Triturating with acetonitrile gave crude (Z)—N-(2-methyl-5-nitrophenyl)thieno[2,3-b]pyrazine-6-carbimidoyl chloride 76 (474 mg, 112%) which was used without further purification. (m/z)=333 (M+H)$^+$.

Step 3: synthesis of (E)-N-(2-methyl-5-nitrophenyl) thieno[2,3-b]pyrazine-6-carbimidoyl cyanide (77)

To a solution of (Z)—N-(2-methyl-5-nitrophenyl)thieno[2,3-b]pyrazine-6-carbimidoyl chloride 76 (100 mg, 0.301 mmol) in THF (15 mL), water (0.5 mL) and acetonitrile (15 mL) was added potassium cyanide (98 mg, 1.503 mmol). The reaction was stirred at rt for 6 h. Quenched in NaHCO$_3$ solution and resulting precipitate was collected to give crude (E)-N-(2-methyl-5-nitrophenyl)thieno[2,3-b]pyrazine-6-carbimidoyl cyanide 77 (62 mg, 63.8%) which was used without further purification. (m/z)=324 (M+H)$^+$.

Step 4: synthesis of 2-(5-amino-2-methylphenylamino)-2-(thieno[2,3-b]pyrazin-6-yl)acetonitrile (78)

To a solution of sodium hydrosulfite (434 mg, 2.493 mmol) in water (3 mL) was added ammonia (0.561 mL, 3.64 mmol) and then compound 77 (62 mg, 0.192 mmol) in dioxane (3 mL). The reaction was stirred at rt. for 4 h. Quenched with water and extracted with EtOAc. Organic layer was washed with brine, dried and evaporated to give compound 2-(5-amino-2-methylphenylamino)-2-(thieno[2,3-b]pyrazin-6-yl) acetonitrile 78 (48 mg, 85%) which was used without further purification. (m/z)=296 (M+H)$^+$.

Step 5: synthesis of (E)-N-(5-(3-(2-cyanopropan-2-yl)benzamido)-2-methylphenyl)thieno[2,3-b]pyrazine-6-carbimidoyl cyanide (79)

A solution of 7-aminothieno[2,3-b]pyrazine-6-carboxylic acid 8 (33.8 mg, 0.179 mmol), HATU (74.1 mg, 0.195 mmol), DIPEA (0.081 mL, 0.488 mmol) in DMF (1 mL) was stirred at rt for 30 min. 2-(5-amino-2-methylphenylamino)-2-(thieno[2,3-b]pyrazin-6-yl)acetonitrile 78 (48 mg, 0.163 mmol) was added and stirred overnight at rt. Quenched with citric acid solution (3%) and extracted with EtOAc. Organic layer was washed with brine, dried and evaporated. Purification by HPLC gave the title compound (E)-N-(5-(3-(2-cyanopropan-2-yl)benzamido)-2-methylphenyl)thieno[2,3-b] pyrazine-6-carbimidoyl cyanide 79 (4 mg, 5.30%). NMR (400 MHz, DMSO-d6) 1.76 (s, 6H), 2.26 (s, 3H), 7.41 (d, J=8.2 Hz, 1H), 7.63 (m, 2H), 7.77 (m, 1H), 7.86 (d, J=2.0 Hz, 1H), 7.97 (d, J=7.4 Hz, 1H), 8.06 (s, 1H), 8.36 (s, 1H), 8.80 (d, J=2.3 Hz, 1H), 8.93 (d, J=2.3 Hz, 1H), 10.49 (s, 1H). (m/z)=465 (M+H)$^+$.

Example 57

Synthesis of N-(2-methyl-5-(3-(thiophen-3-yl)benzamido)phenyl)thieno[2,3-b]pyrazine-6-carboxamide (83)

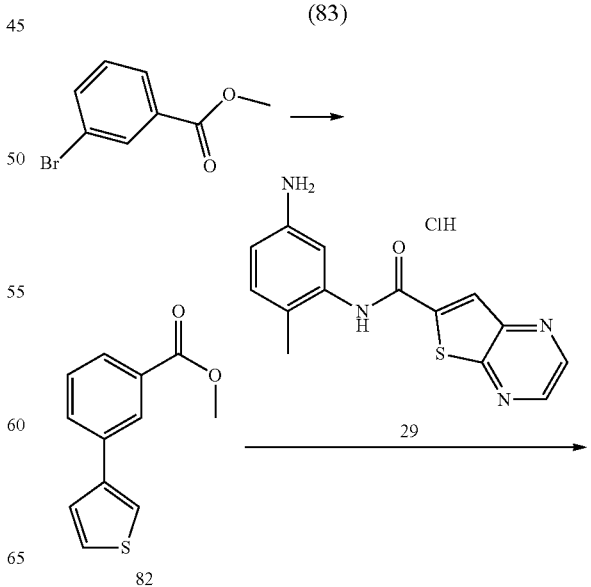

-continued

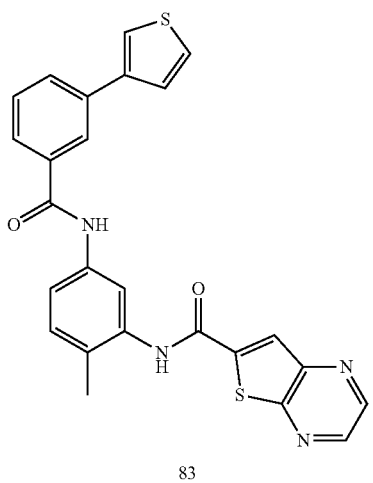

Step 1: synthesis of methyl 3-(thiophen-3-yl)benzoate (82)

Nitrogen (gas) was bubbled through the solution of methyl 3-bromobenzoate (50 mg, 0.233 mmol), potassium carbonate (96 mg, 0.698 mmol) and 3-thiopheneboronic acid (59.5 mg, 0.465 mmol) in dioxane (2 mL) and Water (0.2 mL) for 5 minutes. tetrakis(triphenylphosphine)palladium(0) (26.9 mg, 0.023 mmol) was added and again nitrogen was bubbled through the solution for 5 minutes. The reaction mixture was heated overnight at 100° C. and concentrated to dryness. Purified by chromatography (20% EtOAc in heptane) gave compound methyl 3-(thiophen-3-yl)benzoate 82 (50 mg, 99%). (m/z)=219 (M+H)$^+$.

Step 2: synthesis of N-(2-methyl-5-(3-(thiophen-3-yl)benzamido)phenyl)thieno[2,3-b]pyrazine-6-carboxamide (83)

To a suspension of N-(5-amino-2-methylphenyl)thieno[2,3-b]pyrazine-6-carboxamide hydrochloride 29 (73.5 mg, 0.229 mmol) in toluene (1.5 mL) was added trimethylaluminum (0.458 mL, 0.916 mmol) and was stirred for 15 min. methyl 3-(thiophen-3-yl)benzoate 82 (50 mg, 0.229 mmol) in toluene (1.5 mL) was added. The reaction mixture was stirred overnight at 60° C. Quenched with a saturated solution of NaHCO$_3$ and extracted twice with EtOAc. Organic layer was washed with brine, dried, and evaporated. Purification by HPLC gave the title compound N-(2-methyl-5-(3-(thiophen-3-yl)benzamido)phenyl)thieno[2,3-b]pyrazine-6-carboxamide 83 (6 mg, 5%). NMR (400 MHz, DMSO-d6) 2.27 (s, 3H), 7.32 (d, J=8.2 Hz, 1H), 7.58 (t, J=7.8 Hz, 1H), 7.64-7.72 (m, 3H), 7.87 (d, J=7.8 Hz, 1H), 7.91 (d, J=2.3 Hz, 1H), 7.94 (d, J=7.8 Hz, 1H), 8.01 (dd, 2.7 Hz and 1.6 Hz, 1H), 8.27 (t, J=1.6 Hz, 1H), 8.55 (s, 1H), 8.76 (d, J=2.3 Hz, 1H), 8.89 (d, J=2.3 Hz, 1H), 10.37 (s, 1H), 10.53 (s, 1H). (m/z)=471 (M+H)$^+$.

Example 58

Synthesis of N-(5-(3-(2-cyanopropan-2-yl)benzamido)-2-methylphenyl)-2-oxo-1,2-dihydrothieno[2,3-b]pyrazine-6-carboxamide (85)

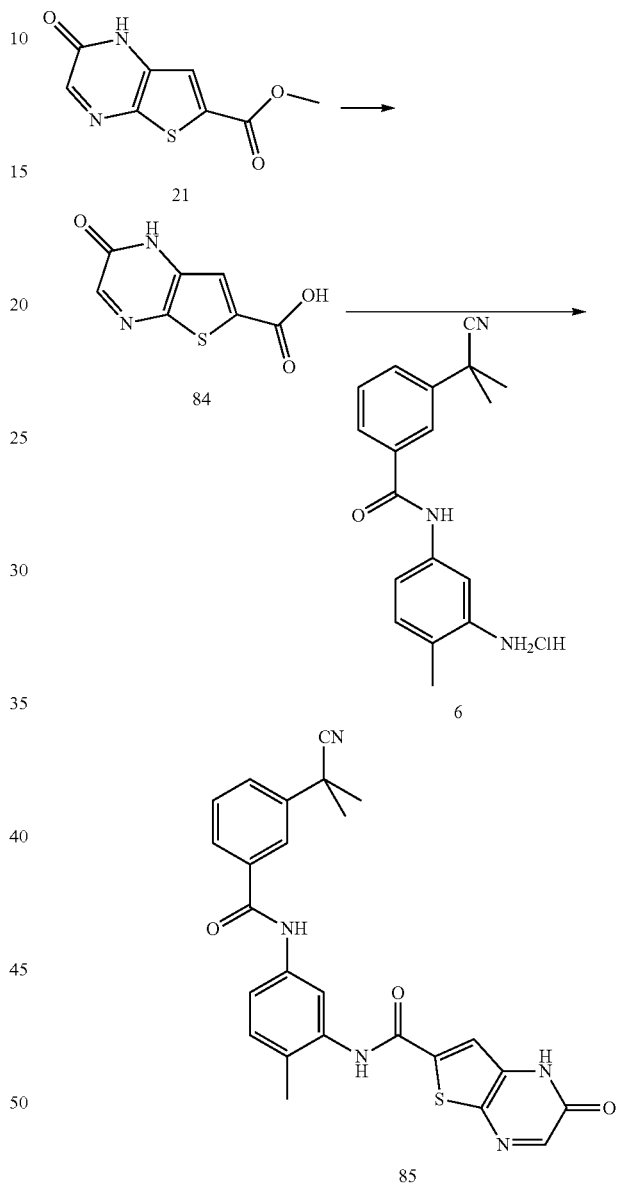

Step 1: synthesis of 2-oxo-1,2-dihydrothieno[3,2-b]pyrazine-6-carboxylic acid (84)

To a solution of methyl 2-oxo-1,2-dihydrothieno[3,2-b]pyrazine-6-carboxylate 21 (50 mg, 0.238 mmol) in methanol (3 mL) was added a solution of 2N sodium hydroxide (0.238 mL, 0.476 mmol). The reaction was stirred at rt for 2 h. Quenched with 2N HCl solution and extracted with EtOAc. Organic layer was washed with brine, dried and evaporated to give crude 2-oxo-1,2-dihydrothieno[3,2-b]pyrazine-6-carboxylic acid 84 (27 mg, 57%).

Step 2: synthesis of N-(5-(3-(2-cyanopropan-2-yl)benzamido)-2-methylphenyl)-2-oxo-1,2-dihydrothieno[2,3-b]pyrazine-6-carboxamide (85)

A solution of 2-oxo-1,2-dihydrothieno[3,2-b]pyrazine-6-carboxylic acid 84 (27 mg, 0.138 mmol), TBTU (48.6 mg, 0.151 mmol) and DIPEA (0.068 mL, 0.413 mmol) in DMF (1 mL) was stirred for 15 min. N-(3-amino-4-methylphenyl)-3-(2-cyanopropan-2-yl)benzamide hydrochloride 6 (45.4 mg, 0.138 mmol) in DMF (1 mL) was added and stirred overnight at 50° C. Quenched with water and extracted with EtOAc. Organic layer was washed with water, dried and evaporated. Purification by HPLC gave the title compound N-(5-(3-(2-cyanopropan-2-yl)benzamido)-2-methylphenyl)-2-oxo-1,2-dihydrothieno[2,3-b]pyrazine-6-carboxamide 85 (0.2 mg, 0.308%). (m/z)=472 (M+H)$^+$.

Example 59

Synthesis of N-(5-(3-(2-cyanopropan-2-yl)benzamido)-2-methylphenyl)-3-(methylamino)thieno[2,3-b]pyrazine-6-carboxamide (96a)

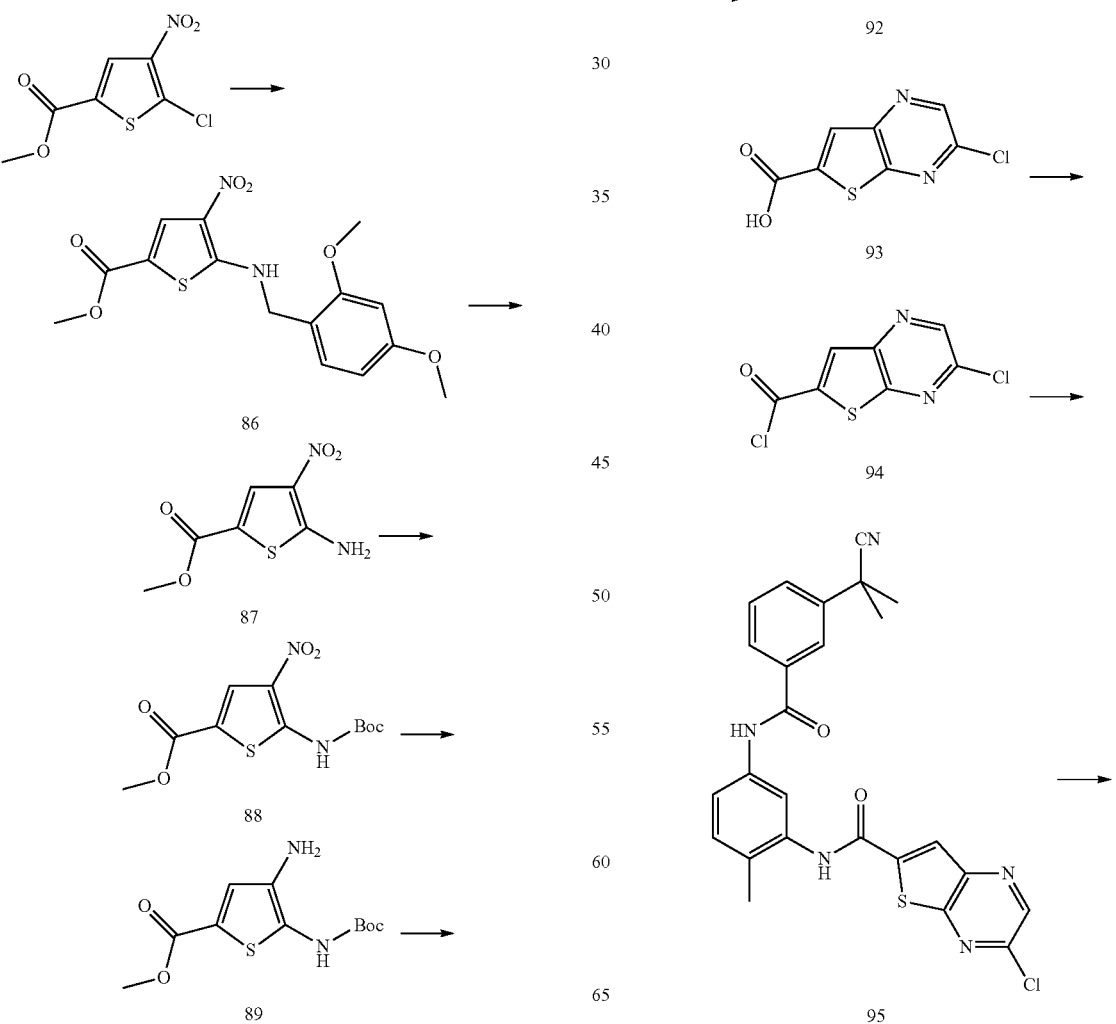

-continued

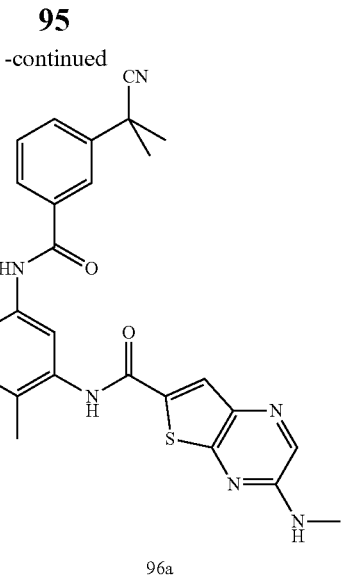

96a

Step 1: synthesis of methyl 5-(2,4-dimethoxybenzylamino)-4-nitrothiophene-2-carboxylate (86)

A mixture of 2,4-dimethoxybenzylamine (58.7 mmol, 8.81 ml, 9.81 g), methyl 5-chloro-4-nitrothiophene-2-carboxylate (45.1 mmol, 10 g) and potassium carbonate (180 mmol, 24.94 g) were stirred at rt in Acetonitrile (226 mL) for 1 h. Reaction was quenched with water and the resulting precipitate was collected to give methyl 5-(2,4-dimethoxybenzylamino)-4-nitrothiophene-2-carboxylate 86 (15.5 g, 97%). NMR (400 MHz, CDCl$_3$) 3.82 (s, 3H), 3.85 (s, 3H), 3.86 (s, 3H), 4.45 (d, J=5.9 Hz, 2H), 6.46 (dd, J=8.2 Hz and 2.3 Hz, 1H), 6.50 (d, J=2.3 Hz, 1H), 7.20 (d, J=8.2 Hz, 1H), 7.99 (s, 1H), 8.89 (br s, 1). (m/z)=353 (M+H)$^+$.

Step 2: synthesis of methyl 5-amino-4-nitrothiophene-2-carboxylate (87)

A solution of methyl 5-(2,4-dimethoxybenzylamino)-4-nitrothiophene-2-carboxylate 86 (40.3 mmol, 14.2 g) in CH$_2$Cl$_2$ (100 mL) and TFA (10 mL) was stirred overnight at rt. Reaction mixture was poured on ice and the precipitate was collected to give methyl 5-amino-4-nitrothiophene-2-carboxylate 87 (8.15 g, 100%). NMR (400 MHz, DMSO-d6) 3.77 (s, 3H), 7.75 (s, 1H), 9.06 (br s, 2H).

Step 3: synthesis of methyl 5-(tert-butoxycarbonylamino)-4-nitrothiophene-2-carboxylate (88)

To a solution of methyl 5-amino-4-nitrothiophene-2-carboxylate 87 (1.236 mmol, 250 mg) in THF (5 mL) at 0° C., di-tert-butyl dicarbonate (1.484 mmol, 324 mg) and triethylamine (1.855 mmol, 0.259 mL) were added and stirred overnight at rt. Additional (2 eq) of di-tert-butyl dicarbonate was added and the reaction was stirred overnight at 40° C. Reaction was quenched with saturated solution of NaHCO$_3$ and extracted with CH$_2$Cl$_2$/methanol 9/1 (2×). Organic layer was washed with brine, dried and evaporated. The crude product was purified with column chromatography (heptane/ethyl acetate gradient 9/1 to 1/1) to yield methyl 5-(tert-butoxycarbonylamino)-4-nitrothiophene-2-carboxylate 88 (374 mg, 100%). NMR (400 MHz, CDCl$_3$) 1.58 (s, 9H), 3.89 (s, 3H), 8.10 (s, 1H), 10.14 (br s, 1H).

Step 4: synthesis of methyl 4-amino-5-(tert-butoxycarbonylamino)thiophene-2-carboxylate (89)

A solution of methyl 5-(tert-butoxycarbonylamino)-4-nitrothiophene-2-carboxylate 88 (0.165 mmol, 50 mg) and palladium on activated carbon (0.083 mmol, 9.79 mg) in methanol (5 mL) was stirred for 1 h at rt with hydrogen gas bubbling through. Additional (0.2 eq) of Pd/C was added and stirred for 1 h. Reaction mixture was filtered and the filtrate was concentrated under reduced pressure to give methyl 4-amino-5-(tert-butoxycarbonylamino)thiophene-2-carboxylate 89 (45 mg, 100%). NMR (400 MHz, CDCl$_3$) 1.52 (s, 9H), 3.83 (s, 3H), 6.85 (br s, 1H), 7.30 (s, 1H). (m/z)=273 (M+H)$^+$.

Step 5: synthesis of methyl 5-(tert-butoxycarbonylamino)-4-(2-methoxy-2-oxoethylamino)thiophene-2-carboxylate (90)

To a solution of methyl 4-amino-5-(tert-butoxycarbonylamino)thiophene-2-carboxylate 89 (0.037 mmol, 10 mg) in CH$_2$Cl$_2$ (1 mL), triethylamine (0.367 mmol, 51.2 µL) and methyl bromoacetate (0.184 mmol, 17.45 µL) were added and stirred at rt for 3 h. The reaction was quenched in water and extracted with CH$_2$Cl$_2$. The organic layer was dried with phaseseparator whereafter and concentrated under reduced pressure to give methyl 5-(tert-butoxycarbonylamino)-4-(2-methoxy-2-oxoethylamino)thiophene-2-carboxylate 90 (10 mg, 79%). NMR (400 MHz, CDCl$_3$) 1.54 (s, 9H), 3.31 (br s, 1H), 3.77 (s, 3H), 3.79 (d, J=6.3 Hz, 2H), 3.82 (s, 3H), 7.38 (s, 1H), 7.54 (br s, 1H). (m/z)=345 (M+H)$^+$.

Step 6: synthesis of methyl 3-oxo-3,4-dihydrothieno[2,3-b]pyrazine-6-carboxylate (91)

To a solution of 90 (0.035 mmol, 12 mg) in dioxane (0.5 mL), HCl 4N in dioxane (1.742 mmol, 436 µl) was added and the solution was heated overnight at 80° C. The reaction was neutralized with a saturated solution of NaHCO$_3$ and extracted with CH$_2$Cl$_2$ (2×). The organic layer was dried with phase separator and concentrated to give methyl 3-oxo-3,4-dihydrothieno[2,3-b]pyrazine-6-carboxylate 91 (7.3 mg, 100%). NMR (400 MHz, CDCl$_3$) 3.96 (s, 3H), 8.05 (s, 1H), 8.29 (s, 1H). (m/z)=211 (M+H)$^+$.

Step 7: synthesis of methyl 3-chlorothieno[2,3-b]pyrazine-6-carboxylate (92)

A mixture of 91 (6.66 mmol, 1.4 g) in phosphorus oxychloride (21.46 mmol, 2 mL) was heated to reflux for 5 days. Reaction mixture was concentrated under reduced pressure and co-evaporated with toluene (3×). The crude product was purified by chromatography (heptane/ethyl acetate 9/1) to give methyl 3-chlorothieno[2,3-b]pyrazine-6-carboxylate 92 (0.6 g, 40%). NMR (400 MHz, CDCl$_3$) 4.01 (s, 3H), 8.18 (s, 1H), 8.71 (s, 1H). (m/z)=229 (M+H)$^+$.

Step 8: synthesis of 3-chlorothieno[2,3-b]pyrazine-6-carboxylic acid (93)

To a solution of methyl 3-chlorothieno[2,3-b]pyrazine-6-carboxylate 92 (2.62 mmol, 600 mg) in 5 mL THF was added sodium hydroxide 2N in water (13.12 mmol, 6560 µl) and stirred at rt for 2 h. The reaction was quenched in 2N HCl extracted with $CH_2Cl_2$/methanol (9/1) (3×). Organic layers was dried and concentrated under reduced pressure to give 3-chlorothieno[2,3-b]pyrazine-6-carboxylic acid 93 (563 mg, 100%).

Step 9: synthesis of 3-chlorothieno[2,3-b]pyrazine-6-carbonyl chloride (94)

A solution of 3-chlorothieno[2,3-b]pyrazine-6-carboxylic acid 93 (0.191 mmol, 41 mg) in thionyl chloride (27.4 mmol, 2 ml, 3262 mg) was heated at 80° C. for 2 h. Reaction mixture was concentrated under reduced pressure and co-evaporated with toluene (2×) to give 3-chlorothieno[2,3-b]pyrazine-6-carbonyl chloride 94 (44 mg, 100%).

Step 10: Synthesis of 3-chloro-N-(5-(3-(2-cyanopropan-2-yl)benzamido)-2-methylphenyl)thieno[2,3-b]pyrazine-6-carboxamide (95)

To a solution of N-(3-amino-4-methylphenyl)-3-(2-cyanopropan-2-yl)benzamide 5 (2.56 mmol, 750 mg) and triethylamine (12.78 mmol, 1.782 mL) in $CH_2Cl_2$ 1 ml at 0° C. was added 3-chlorothieno[2,3-b]pyrazine-6-carbonyl chloride 94 in 1 mL $CH_2Cl_2$ and stirred at rt for 1 h. The reaction mixture was quenched with water, extracted with $CH_2Cl_2$ (2×). The organic layer was dried and concentrated under reduced pressure. Purified with column chromatography (10-20% ethyl acetate in $CH_2Cl_2$) gave 3-chloro-N-(5-(3-(2-cyanopropan-2-yl)benzamido)-2-methylphenyl)thieno[2,3-b]pyrazine-6-carboxamide 95 (1.04 g, 83%). NMR (400 MHz, DMSO-d6) 1.76 (s, 6H), 2.26 (s, 3H), 7.32 (d, J=8.2 Hz, 1H), 7.59 (d, J=7.8 Hz, 1H), 7.64 (dd, J=8.2 Hz and 2.0 Hz, 1H), 7.76 (d, J=7.8 Hz, 1H), 7.87 (d, J=2.3 Hz, 1H), 7.95 (d, J=7.8 Hz, 1H), 8.05 (s, 1H), 8.57 (s, 1H), 8.98 (s, 1H), 10.37 (s, 1H), 10.56 (s, 1H). (m/z)=490 $(M+H)^+$.

Step 11: synthesis of N-(5-(3-(2-cyanopropan-2-yl)benzamido)-2-methylphenyl)-3-(methylamino)thieno[2,3-b]pyrazine-6-carboxamide (96a)

A solution of 3-chloro-N-(5-(3-(2-cyanopropan-2-yl)benzamido)-2-methylphenyl)thieno[2,3-b]pyrazine-6-carboxamide 95 (0.049 mmol, 24 mg) and methylamine 33% in MeOH (0.049 mmol, 500 µL, 4.61 mg) in butan-2-ol (500 µL) was stirred at 150° C. for 5 h. The reaction mixture was concentrated under reduced pressure and purified with HPLC to give the title compound N-(5-(3-(2-cyanopropan-2-yl)benzamido)-2-methylphenyl)-3-(methylamino)thieno[2,3-b]pyrazine-6-carboxamide (96a) (3 mg, 12%). NMR (400 MHz, DMSO-d6) 1.75 (s, 6H), 2.24 (s, 3H), 2.89 (d, J=4.7 Hz, 3H), 7.28 (d, J=8.2 Hz, 1H), 7.60 (t, J=7.8 Hz, 1H), 7.62 (dd, J=8.2 Hz and 2.0 Hz, 1H), 7.75 (d, J=7.8 Hz, 1H), 7.83 (m, 2H), 7.95 (d, J=7.8 Hz, 1H), 8.05 (s, 1H), 8.11 (s, 1H), 8.25 (s, 1H), 10.08 (s, 1H), 10.33 (s, 1H). (m/z)=485 $(M+H)^+$.

Example 60

Synthesis of N-(5-(3-(2-cyanopropan-2-yl)benzamido)-2-methylphenyl)-3-(dimethylamino)thieno[2,3-b]pyrazine-6-carboxamide (96b)

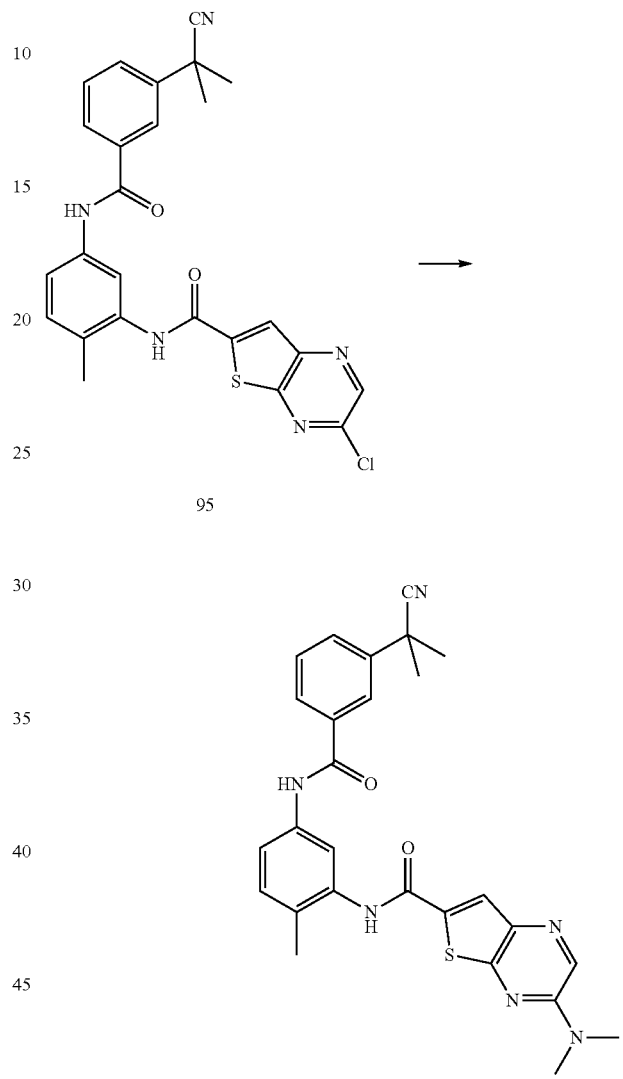

Preparation analogous to 96a (step 11) by using 3-chloro-N-(5-(3-(2-cyanopropan-2-yl)benzamido)-2-methylphenyl)thieno[2,3-b]pyrazine-6-carboxamide 95 (0.061 mmol, 30 mg) and dimethylamine 2M in THF (1.531 mmol, 765 µL) to give N-(5-(3-(2-cyanopropan-2-yl)benzamido)-2-methylphenyl)-3-(dimethylamino)thieno[2,3-b]pyrazine-6-carboxamide 96b (3 mg, 9%). NMR (400 MHz, DMSO-d6) 1.76 (s, 6H), 2.25 (s, 3H), 3.20 (s, 6H), 7.28 (d, J=8.6 Hz, 1H), 7.61 (m, 2H), 7.76 (d, J=7.8 Hz, 1H), 7.84 (d, J=2.0 Hz, 1H), 7.95 (d, J=7.8 Hz, 1H), 8.05 (s, 1H), 8.30 (s, 1H), 8.43 (s, 1H), 10.13 (s, 1H), 10.35 (s, 1H). (m/z)=499 $(M+H)^+$.

Example 61

Synthesis of N-(5-(3-(2-cyanopropan-2-yl)benzamido)-2-methylphenyl)-3-(2-(dimethylamino)ethylamino)thieno[2,3-b]pyrazine-6-carboxamide (96c)

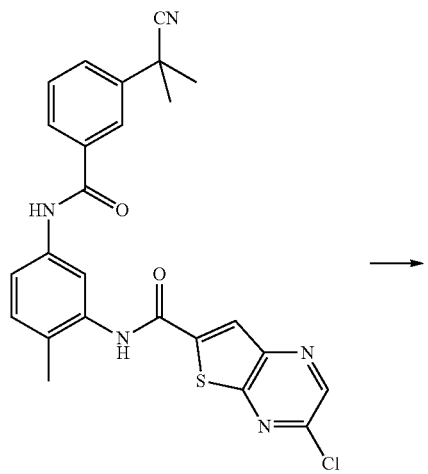

Example 62

Synthesis of N-(5-(3-(2-cyanopropan-2-yl)benzamido)-2-methylphenyl)-3-(2-(dimethylamino)ethylamino)thieno[2,3-b]pyrazine-6-carboxamide hydrochloride (96d)

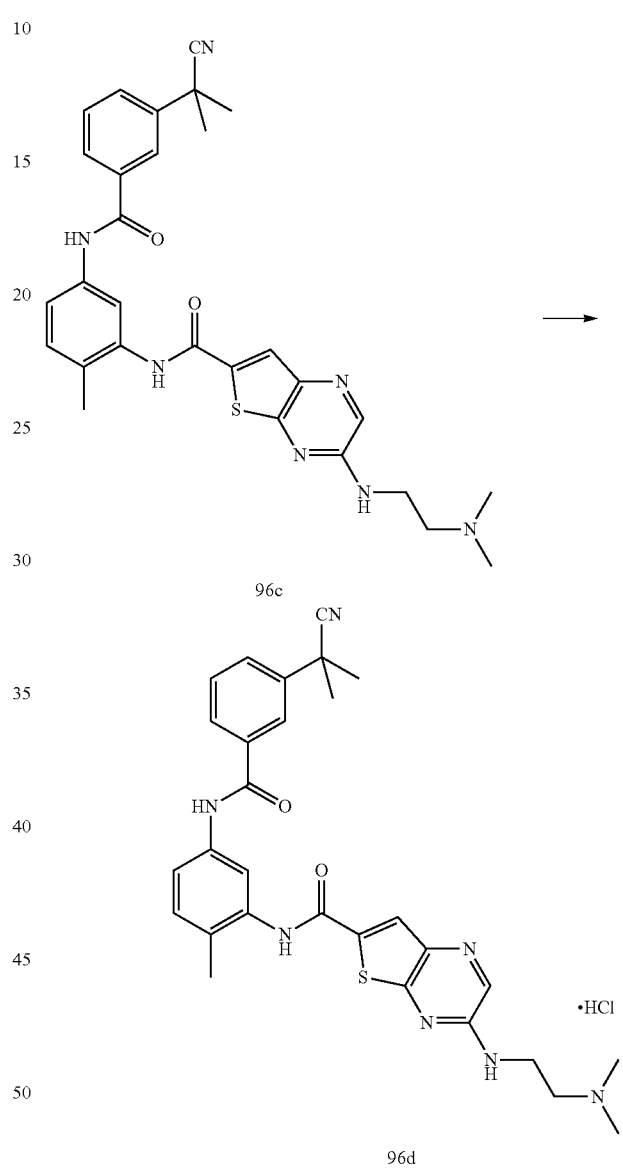

Preparation analogous to 96a by using 3-chloro-N-(5-(3-(2-cyanopropan-2-yl)benzamido)-2-methylphenyl)thieno[2,3-b]pyrazine-6-carboxamide 95 (0.061 mmol, 30 mg) and 1-amino-2-dimethylaminoethane (1.531 mmol, 167 µL, 135 mg) to give N-(5-(3-(2-cyanopropan-2-yl)benzamido)-2-methylphenyl)-3-(2-(dimethylamino)ethylamino)thieno[2,3-b]pyrazine-6-carboxamide 96c (12 mg, 36%). NMR (400 MHz, DMSO-d6) 1.75 (s, 6H), 2.22 (s, 6H), 2.24 (s, 3H), 3.45 (q, J=5.9 Hz, 2H), 7.28 (d, J=8.2 Hz, 1H), 7.61 (m, 2H), 7.75 (m, 2H), 7.82 (d, J=2.0 Hz, 1H), 7.95 (d, J=7.4 Hz, 1H), 8.05 (s, 1H), 8.19 (s, 1H), 8.24 (s, 1H), 10.07 (s, 1H), 10.33 (s, 1H). (m/z)=542 (M+H)$^+$.

Compound 96c (8 mg, 0.015 mmol) was dissolved in dioxane (0.5 mL), 4N HCl (1 eq) was added and stirred for 1 h. Evaporated to dryness to give N-(5-(3-(2-cyanopropan-2-yl)benzamido)-2-methylphenyl)-3-(2-(dimethylamino)ethylamino)thieno[2,3-b]pyrazine-6-carboxamide hydrochloride 96d (9 mg, 100%). NMR (400 MHz, DMSO-d6) 1.76 (s, 6H), 2.24 (s, 3H), 2.84 (d, J=4.7 Hz, 6H), 3.33 (dt, J=5.9 Hz and 5.4 Hz, 2H), 3.75 (dt, J=5.9 Hz and 5.4 Hz, 2H), 7.28 (d, J=8.6 Hz, 1H), 7.60 (m, 2H), 7.75 (d, J=7.8 Hz, 1H), 7.86 (d, J=1.6 Hz, 1H), 7.95 (d, J=7.8 Hz, 1H), 8.06 (s, 1H), 8.18 (s, 1H), 8.21 (t, J=5.4 Hz, 1H), 8.32 (s, 1H), 10.09 (br s, 1H), 10.19 (s, 1H), 10.38 (s, 1H).

Example 63

Synthesis of N-(5-(3-(2-cyanopropan-2-yl)benzamido)-2-methylphenyl)-3-(2-morpholinoethylamino)thieno[2,3-b]pyrazine-6-carboxamide (96e)

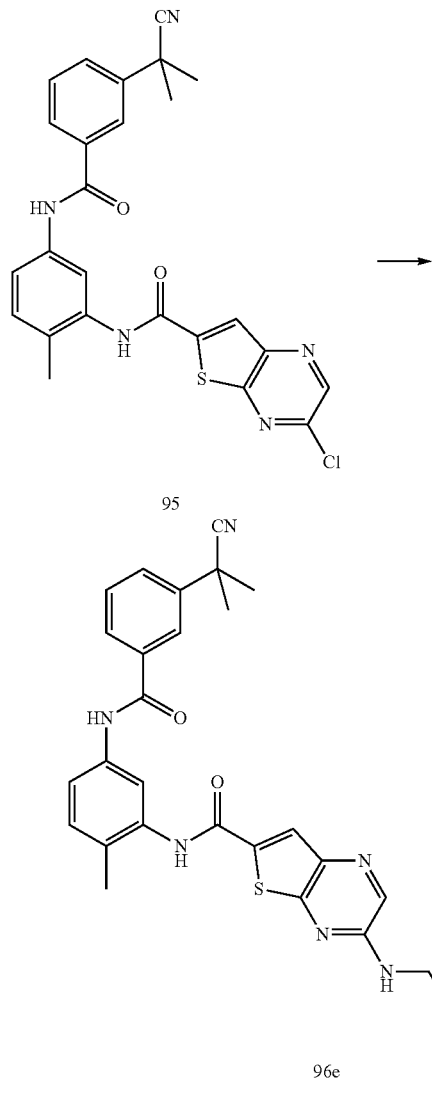

Example 64

Synthesis of N-(5-(3-(2-cyanopropan-2-yl)benzamido)-2-methylphenyl)-3-(2-morpholinoethylamino)thieno[2,3-b]pyrazine-6-carboxamide hydrochloride (96f)

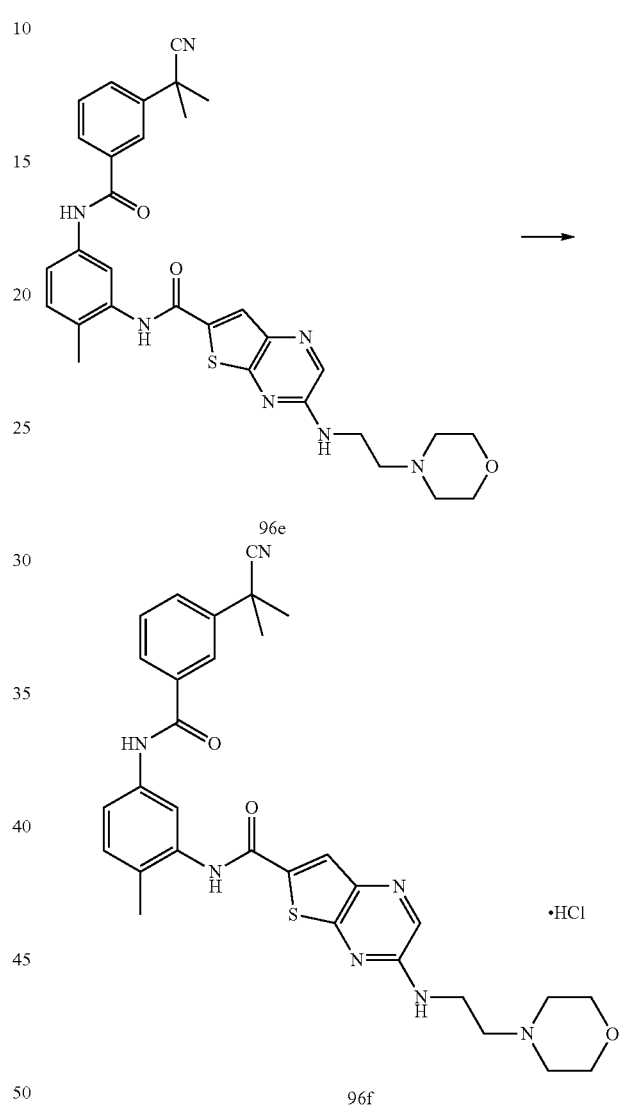

Preparation analogous to 96a by using 3-chloro-N-(5-(3-(2-cyanopropan-2-yl)benzamido)-2-methylphenyl)thieno[2,3-b]pyrazine-6-carboxamide 95 (0.061 mmol, 30 mg) and 4-(2-aminoethyl)morpholine (1.531 mmol, 201 μL) to give N-(5-(3-(2-cyanopropan-2-yl)benzamido)-2-methylphenyl)-3-(2-morpholinoethylamino)thieno[2,3-b]pyrazine-6-carboxamide 96e (12 mg, 34%). NMR (400 MHz, DMSO-d6) 1.75 (s, 6H), 2.24 (s, 3H), 2.46 (br s, 4H), 2.56 (br s, 2H), 3.50 (br s, 2H), 3.60 (br s, 4H), 7.28 (d, J=8.6 Hz, 1H), 7.61 (m, 2H), 7.75 (m, 2H), 7.83 (d, J=2.0 Hz, 1H), 7.94 (d, J=7.8 Hz, 1H), 8.05 (s, 1H), 8.18 (s, 1H), 8.25 (s, 1H), 10.08 (s, 1H), 10.33 (s, 1H). (m/z)=584 (M+H)$^+$.

Compound 96e (8 mg, 0.0137 mmol) was dissolved in dioxane (0.5 mL), 4N HCl (1 eq) was added and stirred for 1 h. Evaporated to dryness to give N-(5-(3-(2-cyanopropan-2-yl)benzamido)-2-methylphenyl)-3-(2-morpholinoethylamino)thieno[2,3-b]pyrazine-6-carboxamide hydrochloride 96f (9 mg, 100%). %). NMR (400 MHz, DMSO-d6) 1.75 (s, 6H), 2.25 (s, 3H), 3.16 (m, 2H), 3.48 (br s, 4H), 3.79 (m, 4H), 3.99 (m, 2H), 7.28 (d, J=8.6 Hz, 1H), 7.61 (m, 2H), 7.76 (m, 2H), 7.86 (d, J=2.0 Hz, 1H), 7.95 (d, J=7.8 Hz, 1H), 8.06 (s, 1H), 8.19 (s, 1H), 8.21 (d, J=5.5 Hz, 1H), 8.31 (s, 1H), 10.17 (s, 1H), 10.37 (s, 1H), 10.49 (br s, 1H).

Example 65

Synthesis of N-(5-(3-(2-cyanopropan-2-yl)benzamido)-2-methylphenyl)-3-(2-methoxyethylamino)thieno[2,3-b]pyrazine-6-carboxamide (96g)

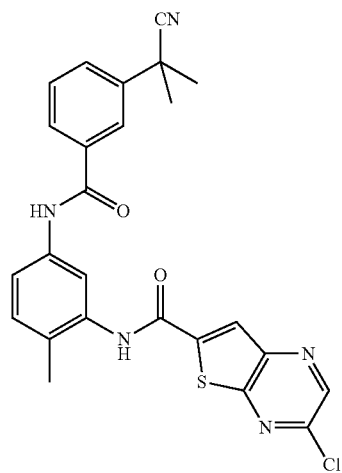

95

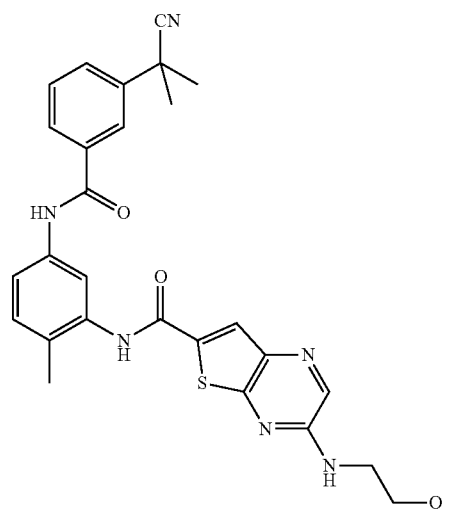

96g

Preparation analogous to 96a by using 3-chloro-N-(5-(3-(2-cyanopropan-2-yl)benzamido)-2-methylphenyl)thieno[2,3-b]pyrazine-6-carboxamide 95 (0.061 mmol, 30 mg) and 2-aminoethyl methyl ether (1.531 mmol, 133 µL) to give N-(5-(3-(2-cyanopropan-2-yl)benzamido)-2-methylphenyl)-3-(2-methoxyethylamino)thieno[2,3-b]pyrazine-6-carboxamide 96g (13 mg, 40%). NMR (400 MHz, DMSO-d6) 1.76 (s, 6H), 2.24 (s, 3H), 3.30 (s, 3H), 3.54 (m, 4H), 7.28 (d, J=8.6 Hz, 1H), 7.61 (m, 2H), 7.76 (m, 1H), 7.83 (m, 1H), 7.94 (m, 1H), 7.96 (s, 1H), 8.05 (s, 1H), 8.18 (s, 1H), 8.25 (s, 1H), 10.09 (s, 1H), 10.34 (s, 1H). (m/z)=530 (M+H)$^+$.

Example 66

Synthesis of N-(5-(3-(2-cyanopropan-2-yl)benzamido)-2-methylphenyl)-3-(2-hydroxyethylamino)thieno[2,3-b]pyrazine-6-carboxamide (96h)

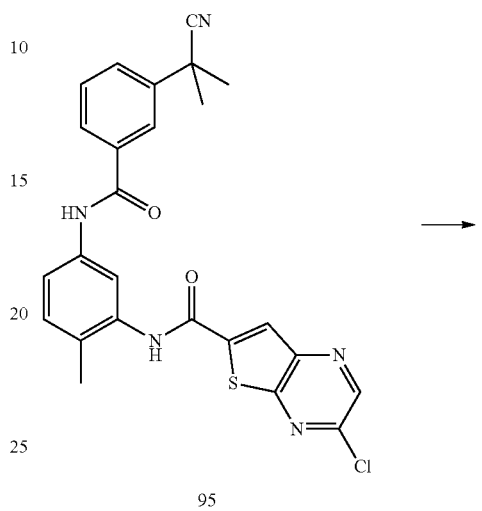

95

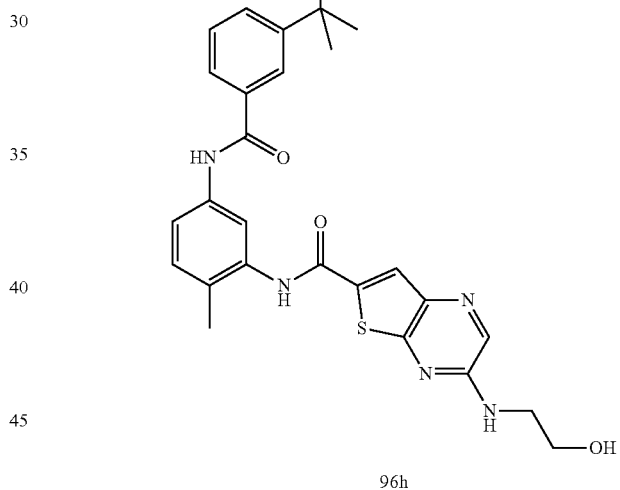

96h

Preparation analogous to 96a by using 3-chloro-N-(5-(3-(2-cyanopropan-2-yl)benzamido)-2-methylphenyl)thieno[2,3-b]pyrazine-6-carboxamide 95 (0.061 mmol, 30 mg) and 2-aminoethanol (1.53 mmol, 92 µL). The crude compound was purified by HPLC and the chromatography (0-10 methanol in CH$_2$Cl$_2$) to give N-(5-(3-(2-cyanopropan-2-yl)benzamido)-2-methylphenyl)-3-(2-hydroxyethylamino)thieno[2,3-b]pyrazine-6-carboxamide 96h (5 mg, 15%). NMR (400 MHz, DMSO-d6) 1.76 (s, 6H), 2.24 (s, 3H), 3.44 (q, J=5.9 Hz and 5.1 Hz, 2H), 3.59 (q, J=5.9 Hz and 5.1 Hz, 2H), 4.83 (t, J=5.1 Hz, 1H), 7.28 (d, J=8.6 Hz, 1H), 7.60 (m, 2H), 7.75 (m, 1H), 7.83 (d, J=2.0 Hz, 1H), 7.89 (m, 1H), 7.95 (d, J=7.8 Hz, 1H), 8.05 (s, 1H), 8.17 (s, 1H), 8.25 (s, 1H), 10.08 (s, 1H), 10.34 (s, 1H). (m/z)=516 (M+H)$^+$.

Example 67

Synthesis of N-(5-(3-(2-cyanopropan-2-yl)benzamido)-2-methylphenyl)-3-(ethylamino)thieno[2,3-b]pyrazine-6-carboxamide (96i)

Example 68

Synthesis of N-(5-(3-(2-cyanopropan-2-yl)benzamido)-2-methylphenyl)-3-(pyridin-3-yl)thieno[2,3-b]pyrazine-6-carboxamide (96j)

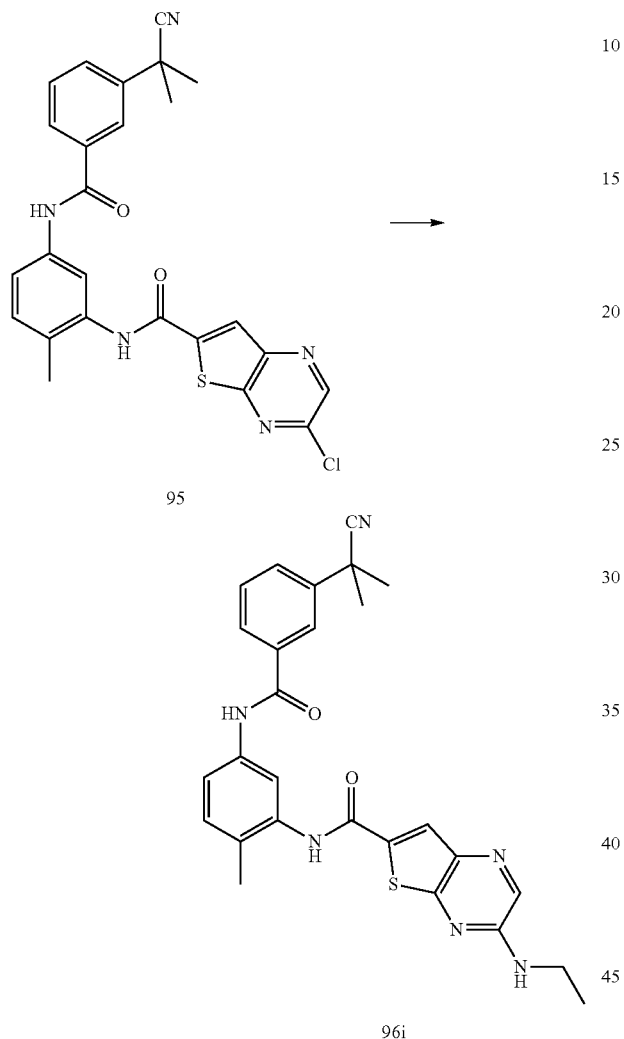

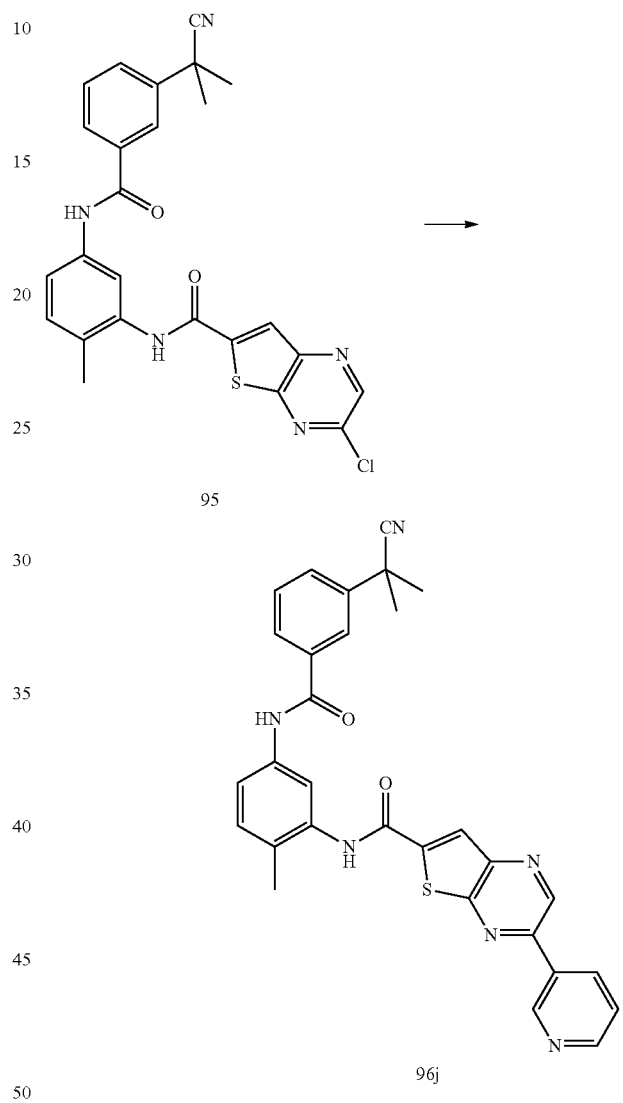

Preparation analogous to 96a by using 3-chloro-N-(5-(3-(2-cyanopropan-2-yl)benzamido)-2-methylphenyl)thieno[2,3-b]pyrazine-6-carboxamide 95 (0.049 mmol, 24 mg), ethylamine hydrochloride (1.22 mmol, 100 mg) and triethylamine (1.71 mmol, 239 μL) to give N-(5-(3-(2-cyanopropan-2-yl)benzamido)-2-methylphenyl)-3-(ethylamino)thieno[2,3-b]pyrazine-6-carboxamide 96i (3 mg, 12%). NMR (400 MHz, DMSO-d6) 1.21 (t, J=7.0 Hz, 3H), 1.76 (s, 6H), 2.25 (s, 3H), 3.37 (m, 2H), 7.28 (d, J=8.2 Hz, 1H), 7.61 (m, 2H), 7.75 (d, J=8.2 Hz, 1H), 7.83 (m, 2H), 7.95 (d, J=7.8 Hz, 1H), 8.05 (s, 1H), 8.10 (s, 1H), 8.24 (s, 1H), 10.08 (s, 1H), 10.33 (s, 1H). (m/z)=500 (M+H)$^+$.

A mixture of 3-chloro-N-(5-(3-(2-cyanopropan-2-yl)benzamido)-2-methylphenyl)thieno[2,3-b]pyrazine-6-carboxamide 95 (204 mmol, 100 mg), pyridine-3-boronic acid (0.306 mmol, 37 mg), potassium phosphate, tribasic (0.408, 87 mg), (0.05 eq, 9 mg), and 2-dicyclohexylphosphino-2',4',6'-triisopropylbiphenyl (0.1 eq, 9 mg) was stirred at 100° C. for 30 min. Evaporated to dryness and purified by chromatography (0-100% ethyl acetate in CH$_2$Cl$_2$) and HPLC to yield N-(5-(3-(2-cyanopropan-2-yl)benzamido)-2-methylphenyl)-3-(pyridin-3-yl)thieno[2,3-b]pyrazine-6-carboxamide 96j (3 mg, 2%). NMR (400 MHz, DMSO-d6) 1.76 (s, 6H), 2.29 (s, 3H), 7.32 (d, J=8.2 Hz, 1H), 7.62 (m, 3H), 7.76 (d, J=7.8 Hz, 1H), 7.90 (s, 1H), 7.96 (d, J=7.8 Hz, 1H), 8.06 (s, 1H), 8.59 (s, 1H), 8.64 (m, 1H), 8.75 (m, 1H), 9.45 (s, 1H), 9.58 (s, 1H), 10.38 (s, 1H), 10.54 (s, 1H). (m/z)=534 (M+H)$^+$.

Example 69

Synthesis of N-(5-(3-(2-cyanopropan-2-yl)benzamido)-2-methylphenyl)-3-(pyridin-4-yl)thieno[2,3-b]pyrazine-6-carboxamide (96k)

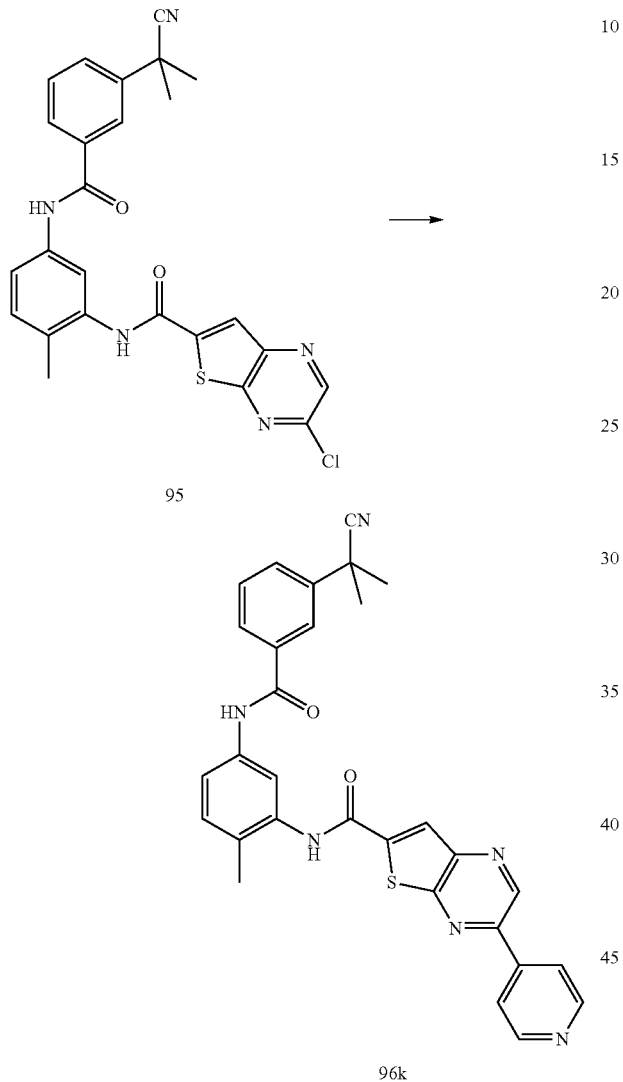

Preparation analogous to 96j by using 2-(4-pyridyl)-5,5-dimethyl-1,2,3-dioxaborinane (0.224 mmol, 43 mg) to give N-(5-(3-(2-cyanopropan-2-yl)benzamido)-2-methylphenyl)-3-(pyridin-4-yl)thieno[2,3-b]pyrazine-6-carboxamide 96k (3 mg, 2%). NMR (400 MHz, DMSO-d6) 1.76 (s, 6H), 2.28 (s, 3H), 7.33 (d, J=8.6 Hz, 1H), 7.62 (m, 2H), 7.76 (d, J=7.8 Hz, 1H), 7.90 (d, J=2.0 Hz, 1H), 7.95 (d, J=7.8 Hz, 1H), 8.06 (s, 1H), 8.25 (s, 1H), 8.27 (s, 1H), 8.61 (s, 1H), 8.80 (s, 1H), 8.82 (s, 1H), 9.63 (s, 1H), 10.38 (s, 1H), 10.57 (s, 1H). (m/z)=534 (M+H)$^+$.

Example 70

Synthesis of N-(5-(3-(2-cyanopropan-2-yl)benzamido)-2-methylphenyl)-3-methylthieno[2,3-b]pyrazine-6-carboxamide (96l)

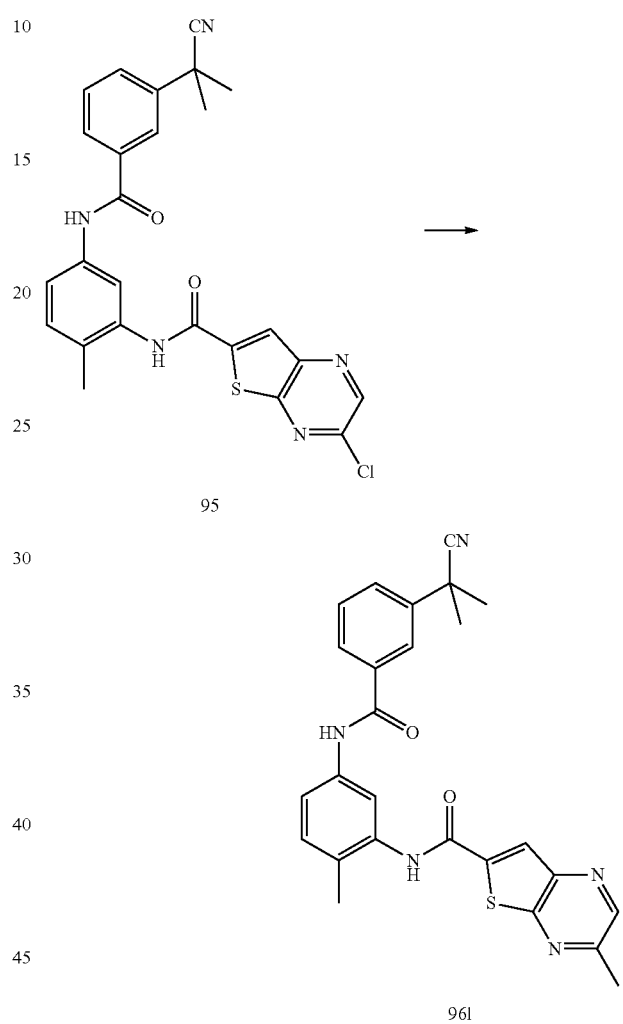

To a mixture of 3-chloro-N-(5-(3-(2-cyanopropan-2-yl)benzamido)-2-methylphenyl)thieno[2,3-b]pyrazine-6-carboxamide (0.204 mmol, 100 mg), potassium carbonate (0.408 mmol, 56.4 mg), 1,1'-bis(diphenylphosphino)ferrocenedichloro palladium(II) (0.020 mmol, 14.77 mg) in THF, was added methylzinc chloride (2.041 mmol, 1020 µl) and stirred overnight at 60° C. The reaction was quenched in water, extracted with ethyl acetate. Organic layer was dried and concentrated under reduced pressure. Crude product was purified with HPLC to give N-(5-(3-(2-cyanopropan-2-yl)benzamido)-2-methylphenyl)-3-methylthieno[2,3-b]pyrazine-6-carboxamide 96l (30 mg, 31%). NMR (400 MHz, DMSO-d6) 1.76 (s, 6H), 2.26 (s, 3H), 2.68 (s, 3H), 7.31 (d, J=8.6 Hz, 1H), 7.62 (m, 2H), 7.76 (d, J=8.6 Hz, 1H), 7.86 (d, J=2.0 Hz, 1H), 7.95 (d, J=7.8 Hz, 1H), 8.06 (s, 1H), 8.50 (s, 1H), 8.78 (s, 1H), 10.36 (s, 1H), 10.45 (s, 1H). (m/z)=471 (M+H)$^+$.

Example 71

Synthesis of N-(5-(3-(2-cyanopropan-2-yl)benzamido)-2-methylphenyl)-3-ethoxythieno[2,3-b]pyrazine-6-carboxamide (98)

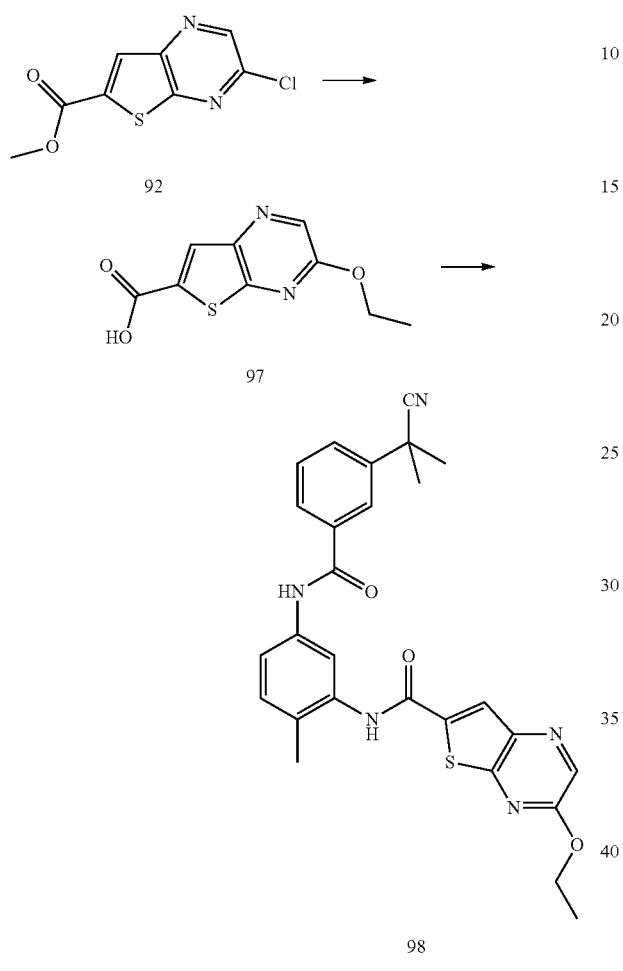

Step 1: synthesis of 3-ethoxythieno[2,3-b]pyrazine-6-carboxylic acid (97)

To a solution of methyl 3-chlorothieno[2,3-b]pyrazine-6-carboxylate 92 (0.044 mmol, 10 mg) in methanol 250 uL and THF 250 uL was added sodium hydroxide 2N in water (0.219 mmol, 109 μA) and stirred overnight at rt. The reaction mixture was quenched in 2N HCl and extracted with $CH_2Cl_2$/methanol (9/1). The organic layer was dried and concentrated under reduced pressure to give 3-ethoxythieno[2,3-b]pyrazine-6-carboxylic acid 97 (9.3 mg, 100%).

Step 2: synthesis of N-(5-(3-(2-cyanopropan-2-yl)benzamido)-2-methylphenyl)-3-ethoxythieno[2,3-b]pyrazine-6-carboxamide (98)

A solution of 97 (0.085 mmol, 18.29 mg), N,N-diisopropylethylamine (0.426 mmol, 0.070 ml, 55.1 mg) and HATU (0.128 mmol, 48.6 mg) in DMF (1 mL) was stirred for 5 min. N-(3-amino-4-methylphenyl)-3-(2-cyanopropan-2-yl)benzamide 5 (0.085 mmol, 25 mg) was added and stirred at 80° C. over the weekend. The reaction mixture was quenched in citric acid solution and extracted with ethyl acetate (2×). Organic layer was washed with brine, dried and concentrated under reduced pressure. The crude compound was purified with HPLC to give the title compound N-(5-(3-(2-cyanopropan-2-yl)benzamido)-2-methylphenyl)-3-ethoxythieno[2,3-b]pyrazine-6-carboxamide 98 (3 mg, 7%). NMR (400 MHz, $CDCl_3$) 1.48 (t, 3H), 1.78 (s, 6H), 2.36 (s, 3H), 4.51 (q, J=7.0 Hz, 2H), 7.24 (m, 1H), 7.52 (t, J=7.8 Hz, 1H), 7.72 (t, J=7.8 Hz, 2H), 7.79 (m, 2H), 7.91 (s, 1H), 7.98 (m, 2H), 8.16 (d, J=2 Hz, 1H), 8.32 (s, 1H). (m/z)=501 $(M+H)^+$.

Example 72

Synthesis of N-(5-(3-(2-cyanopropan-2-yl)benzamido)-2-methylphenyl)-7-oxo-6,7-dihydrothieno[2,3-b]pyrazine-6-carboxamide (100)

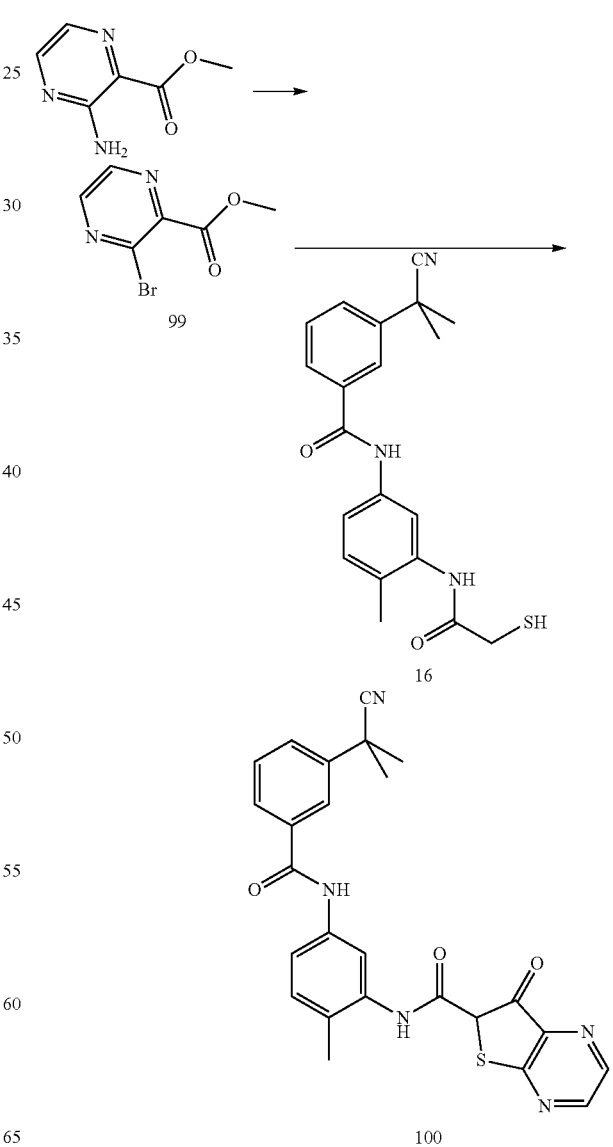

Step 1: synthesis of methyl 3-bromopyrazine-2-carboxylate (99)

To a solution of methyl 3-amino-2-pyrazinecarboxylate (13.06 mmol, 2 g) in hydrobromic acid (13.06 mmol, 7.4 ml, 1.057 g) at 0° C. was added bromine (38.9 mmol, 2 mL, 6.22 g) drop wise and then a solution of sodium nitrite (33.3 mmol, 2.3 g) in water (4 mL). The reaction was stirred for 2 h at 0° C. and the reaction mixture was extracted with $CH_2Cl_2$.

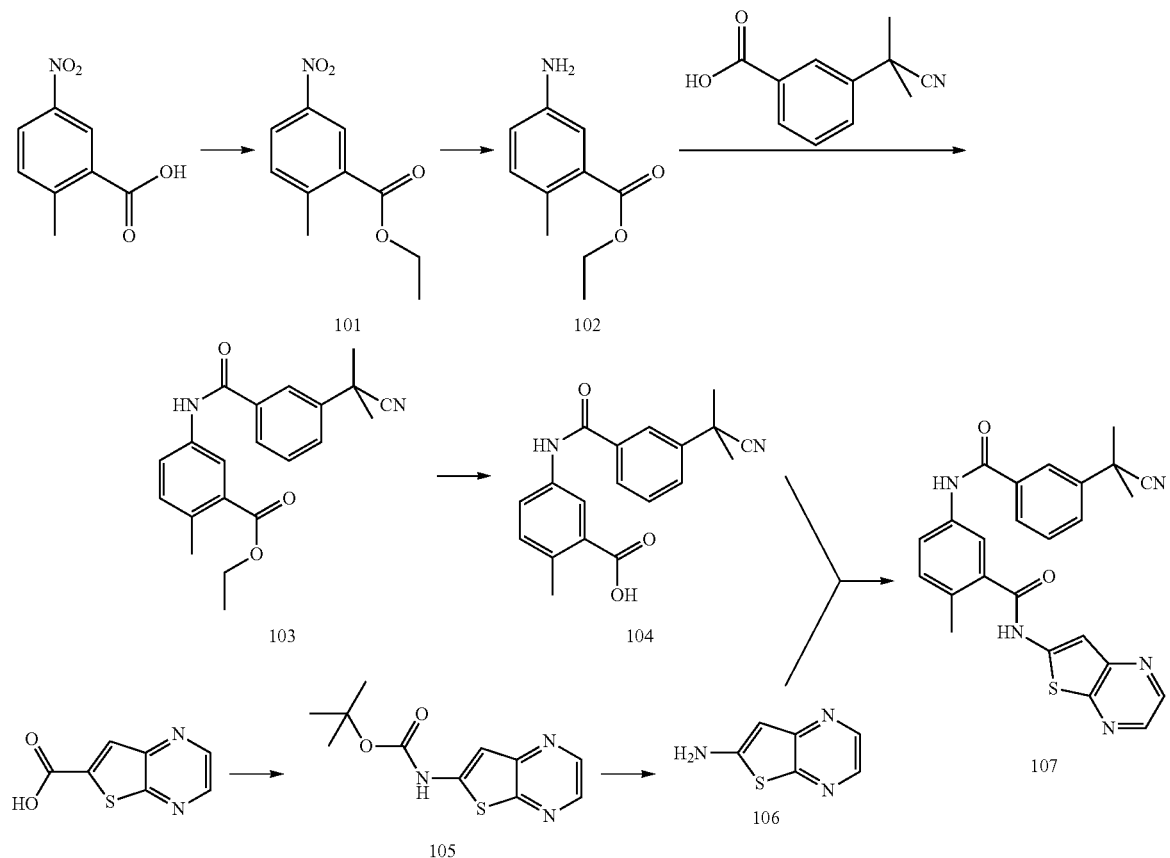

Organic layer was dried and evaporated to give crude methyl 3-bromopyrazine-2-carboxylate 101 (1.2 gr, 43%). (m/z)=217 and 219 $(M+H)^+$.

Step 2: synthesis of N-(5-(3-(2-cyanopropan-2-yl)benzamido)-2-methylphenyl)-7-oxo-6,7-dihydrothieno[2,3-b]pyrazine-6-carboxamide (100)

A solution of 3-(2-cyanopropan-2-yl)-N-(3-(2-mercaptoacetamido)-4-methylphenyl)benzamide 16 (0.054 mmol, 20 mg), methyl 3-bromopyrazine-2-carboxylate 101 (0.054 mmol, 11.8 mg) and $Na_2CO_3$ (1.2 eq, 7 mg) in ethanol (1 mL) was stirred overnight at 70° C. The reaction mixture was quenched in cold 1N HCl solution and extracted with $CH_2Cl_2$. Organic layer was dried and evaporated. Purification by chromatography (0-10% methanol in $CH_2Cl_2$) gave N-(5-(3-(2-cyanopropan-2-yl)benzamido)-2-methylphenyl)-7-oxo-6,7-dihydrothieno[2,3-b]pyrazine-6-carboxamide 102 (11 mg, 42.9%). NMR (400 MHz, DMSO-d6) 1.77 (s, 6H) 2.35 (s, 3H), 7.15 (d, J=8.6 Hz, 1H), 7.48 (dd, J=8.2 Hz and 2.3 Hz, 1H), 7.59 (t, J=7.8 Hz, 1H), 7.74 (d, J=7.8 Hz, 1H), 7.97 (d, J=7.8 Hz, 1H), 8.07 (t, J=2.0 Hz, 1H), 8.54 (br s, 1H), 8.62 (br s, 1H), 8.66 (d, J=1.6 Hz, 1H), 10.29 (s, 1H). (m/z)=473 $(M+H)^+$.

Example 73

Synthesis of 5-(3-(2-cyanopropan-2-yl)benzamido)-2-methyl-N-(thieno[2,3-b]pyrazin-6-yl)benzamide (107)

Step 1: synthesis of ethyl 2-methyl-5-nitrobenzoate (101)

To a solution of 2-methyl-5-nitrobenzoic acid (27.6 mmol, 5 g) in ethanol (100 mL), sulfuric acid (138 mmol, 7.36 ml) was added slowly and stirred overnight at 80° C. The reaction mixture was neutralized with saturated solution of $Na_2CO_3$, extracted with diethyl ether (3×), organic layers were washed with brine, dried and concentrated under reduced pressure to yield crude product ethyl 2-methyl-5-nitrobenzoate 101 (5.4 g, 95%). NMR (400 MHz, $CDCl_3$) 1.44 (t, J=7.0 Hz, 3H), 2.72 (s, 3H), 4.42 (q, J=7.04 Hz, 2H), 7.43 (d, J=8.6 Hz, 1H), 8.23 (dd, J=8.6 Hz and 2.7 Hz, 1H), 8.76 (d, J=2.7 Hz, 1H).

Step 2: synthesis of ethyl 5-amino-2-methylbenzoate (102)

To a solution of ethyl 2-methyl-5-nitrobenzoate 101 and acetic acid (516 mmol, 29.6 mL) (25.8 mmol, 5.4 g) in THF (129 mL) at 0° C. was added zinc (516 mmol, 33.8 g) and stirred for 1 h. The reaction was filtered, neutralized with 2N NaOH solution and extracted with ethyl acetate (2×). Organic layers were washed with water, brine, dried and concentrated under reduced pressure to give ethyl 5-amino-2-methylbenzoate 102 (4.6 g, 100%).

Step 3: synthesis of ethyl 5-(3-(2-cyanopropan-2-yl)benzamido)-2-methylbenzoate (103)

A solution of 3-(2-cyanopropan-2-yl)benzoic acid 3 (15.33 mmol, 2.9 g) DIPEA (77 mmol, 12.67 mL) and HATU (18.39 mmol, 6.99 g) in DMF (50 mL) was stirred for 5 min. Ethyl 5-amino-2-methylbenzoate 102 (18.39 mmol, 3.30 g) was added and stirred 6 h at room temperature. Reaction mixture was quenched in water and extracted with ethyl acetate (2×). Organic layers were combined and washed with water (3×), brine and concentrated under reduced pressure. Crude product was purified with Column chromatography (30% ethyl acetate in heptane 7/3) gave 5-(3-(2-cyanopropan-2-yl)benzamido)-2-methylbenzoate 103 (3.5 g, 65%). NMR (400 MHz, CDCl$_3$) 1.40 (t, J=7.0 Hz, 3H), 1.78 (s, 6H), 2.59 (s, 3H), 4.37 (q, J=7.0 Hz, 2H), 7.27 (d, J=7.8 Hz, 1H), 7.53 (t, J=7.8 Hz, 1H), 7.71 (d, J=7.8 Hz, 1H), 7.79 (d, J=7.8 Hz, 1H), 7.86 (d, J=2.0 Hz, 1H), 7.88 (s, 1H), 7.99 (s, 1H), 8.04 (d, J=2.3 Hz, 1H). (m/z)=352 (M+H)$^+$.

Step 4: synthesis of 5-(3-(2-cyanopropan-2-yl)benzamido)-2-methylbenzoic acid (104)

To a solution of 5-(3-(2-cyanopropan-2-yl)benzamido)-2-methylbenzoate 103 (7.13 mmol, 2.5 g) in THF (30 mL), lithium hydroxide (28.5 mmol, 0.683 g) in (20 mL) water was added and the reaction was stirred overnight at 40° C. The reaction mixture was acidified with 2N HCl solution and extracted with ethyl acetate (2×). Organic layer was washed with 2N NaOH (3×), aqueous layer was acidified with 2N HCl solution and the milky mixture was extracted with ethyl acetate (3×), dried and concentrated under reduced pressure. Crude product was triturated with ACN to give 5-(3-(2-cyanopropan-2-yl)benzamido)-2-methylbenzoic acid 104 (550 mg, 23%). NMR (400 MHz, DMSO-d6) 1.76 (s, 6H), 2.50 (s, 3H), 7.30 (d, J=8.6 Hz, 1H), 7.60 (t, J=7.4 Hz, 1H), 7.76 (d, J=7.8 Hz, 1H), 7.90 (dd, J=8.2 Hz and 2.3 Hz, 1H), 7.96 (d, J=7.8 Hz, 1H), 8.06 (t, J=2.0 Hz, 1H), 8.24 (d, J=2.3 Hz, 1H), 10.40 (s, 1H). (m/z)=323 (M+H)$^+$.

Step 5: synthesis of tert-butyl thieno[2,3-b]pyrazin-6-ylcarbamate (105)

To a solution of thieno[2,3-b]pyrazine-6-carboxylic acid (5.55 mmol, 1 g) and triethylamine (16.65 mmol, 2.321 mL) in t-butanol (15 mL) at 70° C., DPPA (6.10 mmol, 1.320 mL) was added. The dark brown solution was stirred overnight at 85° C. The reaction mixture was evaporated to dryness. Purification by chromatography (0-30% ethyl acetate in heptane) gave tert-butyl thieno[2,3-b]pyrazin-6-ylcarbamate 105 (1.28 g, 92%). NMR (400 MHz, CDCl$_3$) 1.57 (s, 9H), 6.77 (s, 1H), 7.42 (br s, 1H), 8.30 (d, J=2.7 Hz, 1H), 8.48 (d, J=2.7 Hz, 1H).

Step 6: synthesis of thieno[2,3-b]pyrazin-6-amine (106)

A red solution of tert-butyl thieno[2,3-b]pyrazin-6-ylcarbamate (5.09 mmol, 1.28 g) in 66% TFA in CH$_2$Cl$_2$ 25 mL was stirred overnight at room temperature The reaction mixture was concentrated in vacuo, dissolved in ethyl acetate, washed with NaHCO$_3$ solution, brine, dried and evaporated to give thieno[2,3-b]pyrazin-6-amine 106 (620 mg, 81%). NMR (400 MHz, DMSO-d6) 5.98 (s, 1H), 7.17 (br s, 2H), 7.93 (d, J=2.7 Hz, 1H), 8.20 (d, J=2.7 Hz, 1H).

Step 7: synthesis of 5-(3-(2-cyanopropan-2-yl)benzamido)-2-methyl-N-(thieno[2,3-b]pyrazin-6-yl)benzamide (107)

A solution of 5-(3-(2-cyanopropan-2-yl)benzamido)-2-methylbenzoic acid 106 (0.310 mmol, 100 mg) in Thionyl-chloride was stirred at 80° C. for 2 h. The light yellow solution was evaporated to dryness and co-evaporated twice with dry toluene. Dissolved in CH$_2$Cl$_2$ (2 mL) and added to a solution of 106 (0.310 mmol, 46.9 mg) and triethylamine (1.551 mmol, 0.216 mL) in CH$_2$Cl$_2$ (2 mL). The reaction was stirred for 1 h at room temperature. Poured in water and extracted with CH$_2$Cl$_2$. The organic layer was dried and evaporated. Purification by HPLC gave 5-(3-(2-cyanopropan-2-yl)benzamido)-2-methyl-N-(thieno[2,3-b]pyrazin-6-yl)benzamide 107 (18 mg, 13%). NMR (400 MHz, DMSO-d6) 1.76 (s, 6H), 2.41 (s, 3H), 7.11 (s, 1H), 7.39 (d, J=8.6 Hz, 1H), 7.62 (t, J=7.8 Hz, 1H), 7.77 (d, J=7.8 Hz, 1H), 7.89 (dd, J=8.6 Hz and 2.3 Hz, 1H), 7.97 (d, J=7.8 Hz, 1H), 8.04 (d, J=2.3 Hz, 1H), 8.07 (t, J=2.0 Hz, 1H), 8.44 (br s, 1H), 8.61 (br s, 1H), 10.48 (s, 1H), 12.29 (s, 1H). (m/z)=457 (M+H)$^+$.

Example 74

Synthesis of 7-amino-N-(2-methyl-5-(3-(trifluoromethyl)phenylcarbamoyl)phenyl)thieno[2,3-b]pyrazine-6-carboxamide (110)

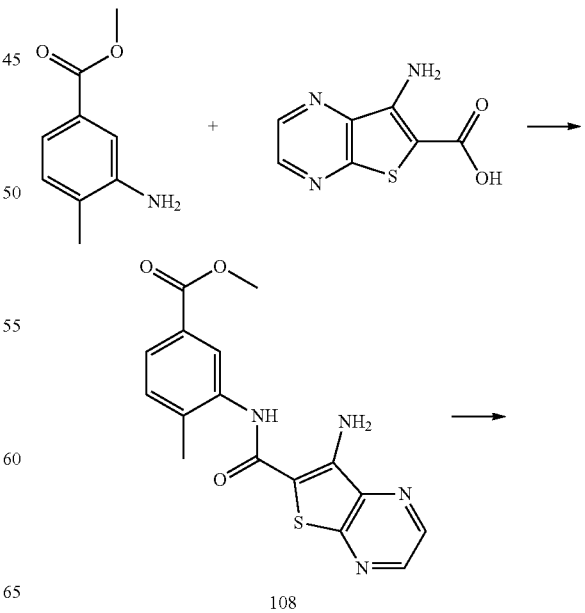

Step 3: synthesis of 7-amino-N-(2-methyl-5-(3-(trifluoromethyl)phenylcarbamoyl)phenyl)thieno[2,3-b]pyrazine-6-carboxamide (110)

A solution of 109 (0.305 mmol, 100 mg), 3-aminobenzotrifluoride (0.305 mmol, 0.038 mL), TBTU (0.457 mmol, 147 mg) and DIPEA (0.914 mmol, 0.150 mL) in NMP (5 ml) stirred overnight at 80° C. The light brown solution was poured into citric acid solution and extracted with ethyl acetate. The combined organic layers were washed with brine and evaporated. The crude compound was purified by HPLC and chromatography (0-5% methanol in $CH_2Cl_2$) gave 7-amino-N-(2-methyl-5-(3-(trifluoromethyl)phenylcarbamoyl)phenyl)thieno[2,3-b]pyrazine-6-carboxamide 110 (14 mg, 10%). NMR (400 MHz, DMSO-d6) 2.33 (s, 3H), 7.10 (s, 2H), 7.47 (m, 2H), 7.61 (m, 1H), 7.85 (dd, J=7.8 Hz and 1.6 Hz, 1H), 8.00 (d, J=2.0 Hz, 1H), 8.09 (d, J=8.2 Hz, 1H), 8.25 (s, 1H), 8.79 (d, J=2.3 Hz, 1H), 8.80 (d, J=2.3 Hz, 1H), 9.62 (s, 1H), 10.52 (s, 1H). (m/z)=472 (M+H)⁺.

Example 75

Synthesis of N-(3-(7-aminothieno[2,3-b]pyrazine-6-carbonyl)-4-methylphenyl)-3-(2-cyanopropan-2-yl)benzamide (116)

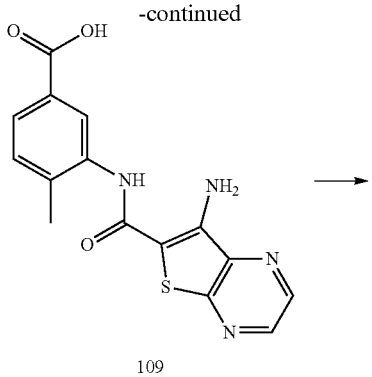

109

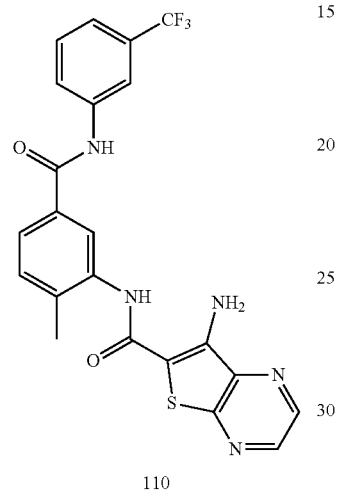

110

Step 1: synthesis of methyl 3-(7-aminothieno[2,3-b]pyrazine-6-carboxamido)-4-methylbenzoate (108)

A solution of 7-aminothieno[2,3-b]pyrazine-6-carboxylic acid (8) (2.56 mmol, 500 mg), methyl 3-amino-4-methylbenzoate (2.56 mmol, 423 mg), TBTU (3.84 mmol, 1234 mg) and DIPEA (7.68 mmol, 1.260 mL in DMF (10 mL) was stirred 2 days at 80° C.

The brown solution was poured into citric acid solution, the precipitation was filtered of and washed with water. Purification by chromatography (0-40% ethyl acetate in $CH_2Cl_2$) gave methyl 3-(7-aminothieno[2,3-b]pyrazine-6-carboxamido)-4-methylbenzoate 108 (143 mg, 15%). (m/z)=343 (M+H)⁺.

Step 2: synthesis of 3-(7-aminothieno[2,3-b]pyrazine-6-carboxamido)-4-methylbenzoic acid (109)

A solution of methyl 3-(7-aminothieno[2,3-b]pyrazine-6-carboxamido)-4-methylbenzoate 108 (0.803 mmol, 275 mg) in THF (10 mL) and 2N NaOH (10 mL) stirred for 4 h. The red solution was diluted with water, acidified with 2N HCl solution pH 5-6 and extracted with ethyl acetate. The combined organic layers were washed with brine, dried and evaporated to give 3-(7-aminothieno[2,3-b]pyrazine-6-carboxamido)-4-methylbenzoic acid 109 (264 mg, 100%). NMR (400 MHz, DMSO-d6) 2.31 (s, 3H), 7.08 (s, 2H), 7.41 (d, J=8.2 Hz, 1H), 7.75 (dd, J=7.8 Hz and 1.6 Hz, 1H), 7.93 (d, J=1.2 Hz, 1H), 8.78 (d, J=2.3 Hz, 1H), 8.79 (d, J=2.3 Hz, 1H), 9.53 (s, 1H), 12.91 (br s, 1H).

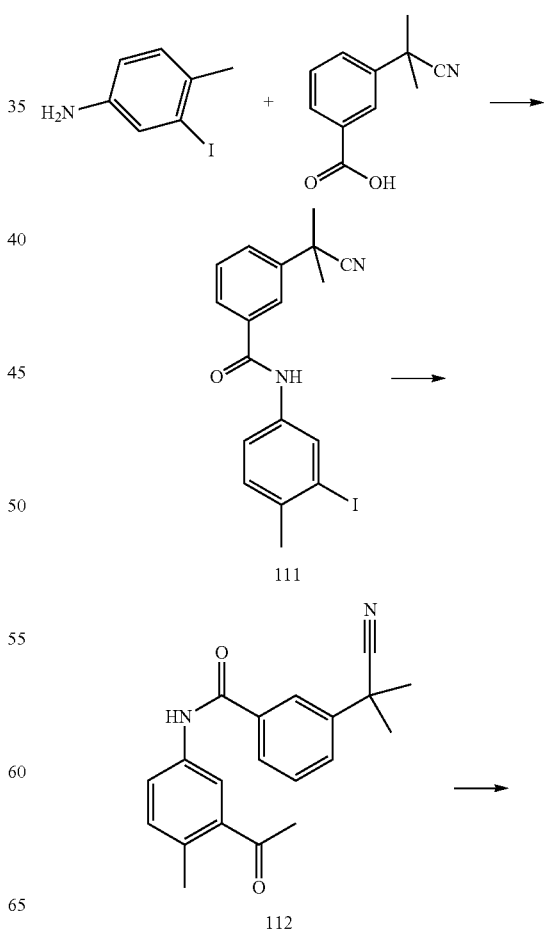

111

112

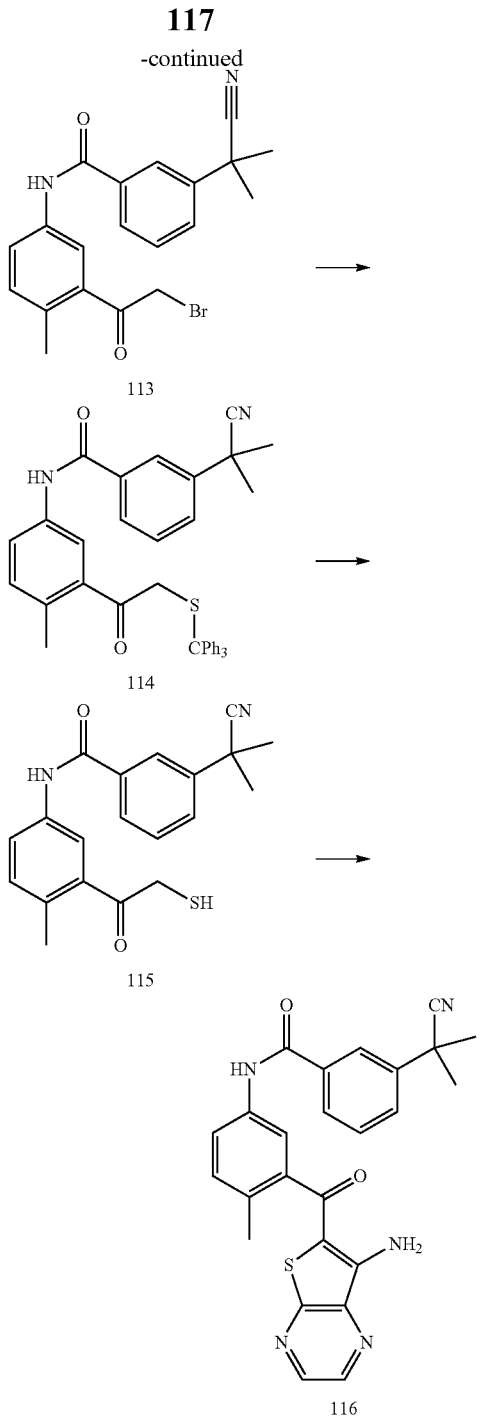

111 (861 mg, 81%). NMR (400 MHz, CDCl₃) 1.78 (s, 6H), 2.42 (s, 3H), 7.23 (d, J=8.2 Hz, 1H), 7.52 (dd, J=8.2 Hz and 7.4 Hz, 1H), 7.58 (dd, J=8.2 Hz and 2.3 Hz, 1H), 7.71 (dq, J=7.8 Hz and 1.2 Hz), 7.76 (m, 1H), 7.78 (m, 1H), 7.96 (t, J=1.6 Hz, 1H), 8.11 (d, J=2.3 Hz, 1H).

Step 2: synthesis of N-(3-acetyl-4-methylphenyl)-3-(2-cyanopropan-2-yl)benzamide (112)

A solution of 3-(2-cyanopropan-2-yl)-N-(3-iodo-4-methylphenyl)benzamide 111 (1.546 mmol, 625 mg), 1-ethoxyvinyltri-n-butyltin (4.64 mmol, 1.567 mL) and bis(triphenylphosphine)palladium(II) chloride (0.155 mmol, 109 mg) in toluene (5 mL) was stirred at 100° C. for 2 h. Cooled down to room temperature, 4N HCl in dioxane (1 mL) was added and stirred for 1 h. Diluted with ethyl acetate, filtrated and evaporated. Purification by chromatography (0-5% ethyl acetate in CH₂Cl₂) gave N-(3-acetyl-4-methylphenyl)-3-(2-cyanopropan-2-yl)benzamide 112 (364 mg, 73.5%). NMR (400 MHz, CDCl₃) 1.79 (s, 6H), 2.52 (s, 3H), 2.62 (s, 3H), 7.26 (d, J=8.2 Hz, 1H), 7.55 (m, 2H), 7.72 (d, J=7.8 Hz, 1H), 7.81 (d, J=7.4 Hz, 1H), 7.91 (br s, 1H), 8.00 (t, J=1.9 Hz, 1H), 8.15 (d, J=2.3 Hz, 1H).

Step 3: synthesis of N-(3-(2-bromoacetyl)-4-methylphenyl)-3-(2-cyanopropan-2-yl)benzamide (113)

To a solution of N-(3-acetyl-4-methylphenyl)-3-(2-cyanopropan-2-yl)benzamide 112 (1.136 mmol, 364 mg) in dioxane (4 mL) and CH₂Cl₂ (1 mL) at 0° C. was added BROMINE (1.250 mmol, 0.064 mL). The reaction was stirred overnight at room temperature. Water was added and extracted with CH₂Cl₂. Organic layer was dried and evaporated to give N-(3-(2-bromoacetyl)-4-methylphenyl)-3-(2-cyanopropan-2-yl)benzamide 113 (450 mg, 99%). (m/z)=401 (M+H)⁺.

Step 4: synthesis of 3-(2-cyanopropan-2-yl)-N-(4-methyl-3-(2-(tritylthio)acetyl)phenyl)benzamide (114)

A solution of N-(3-(2-bromoacetyl)-4-methylphenyl)-3-(2-cyanopropan-2-yl)benzamide 113 (1.127 mmol, 450 mg), DIPEA (1.352 mmol, 0.224 mL) and triphenylmethyl mercaptan (1.240 mmol, 343 mg) in DMF (5 ml) was stirred overnight at room temperature. Evaporated to dryness. Purification by chromatography (0-10% ethyl acetate in Toluene) gave 3-(2-cyanopropan-2-yl)-N-(4-methyl-3-(2-(tritylthio)acetyl)phenyl)benzamide 114 (475 mg, 70.9%). NMR (400 MHz, CDCl₃) 1.80 (s, 6H), 2.38 (s, 3H), 3.55 (s, 2H), 7.31-7.15 (m, 10H), 7.39 (d, J=2.3 Hz, 1H), 7.42 (m, 3H), 7.44 (m, 3H), 7.56 (t, J=7.8 Hz, 1H), 7.72 (m, 2H), 7.74 (m, 1H), 7.79 (d, J=7.8 Hz, 1H), 7.99 (t, J=1.9 Hz, 1H).

Step 5: synthesis of 3-(2-cyanopropan-2-yl)-N-(3-(2-mercaptoacetyl)-4-methylphenyl)benzamide (115)

A solution of 3-(2-cyanopropan-2-yl)-N-(4-methyl-3-(2-(tritylthio)acetyl)phenyl)benzamide 114 (0.799 mmol, 475 mg), trifluoroacetic acid (40.4 mmol, 3 mL) and triethylsilane (0.799 mmol, 0.129 mL) in CH₂Cl₂ (10 mL) was stirred 1 h at room temperature. Evaporated to dryness and purified by chromatography (10% ethyl acetate in CH₂Cl₂) gave 3-(2-cyanopropan-2-yl)-N-(3-(2-mercaptoacetyl)-4-methylphenyl)benzamide 115 (71 mg, 25%). NMR (400 MHz, CDCl₃) 1.79 (s, 6H), 2.51 (s, 3H), 3.93 (d, J=7.4 Hz, 2H), 7.30 (d, J=8.2 Hz, 1H), 7.54 (m, 2H), 7.72 (dq, J=7.8 Hz and 1.2 Hz, 1H), 7.80 (dt, J=7.8 Hz and 1.6 Hz, 1H), 7.90 (br s, 1H), 8.00 (t, J=2.0 Hz, 1H), 8.19 (d, J=2.0 Hz, 1H).

Step 6: synthesis of N-(3-(7-aminothieno[2,3-b]pyrazine-6-carbonyl)-4-methylphenyl)-3-(2-cyanopropan-2-yl)benzamide (116)

A solution of 3-(2-cyanopropan-2-yl)-N-(3-(2-mercaptoacetyl)-4-methylphenyl)benzamide 115 (0.094 mmol, 33 mg), 3-chloropyrazine-2-carbonitrile (0.094 mmol, 13 mg) and sodium carbonate (0.112 mmol, 12 mg) in ethanol (1 mL) was stirred 2 h at 50° C. Quenched in 1N HCl solution and extracted with CH₂Cl₂. Organic layer was dried and evaporated. Purification by HPLC gave N-(3-(7-aminothieno[2,3-b]pyrazine-6-carbonyl)-4-methylphenyl)-3-(2-cyanopropan-2-yl)benzamide 116 (9 mg, 21%). NMR (400 MHz, DMSO-d6) 1.74 (s, 6H), 2.27 (s, 3H), 7.37 (d, J=8.6 Hz, 1H), 7.60 (t, J=7.8 Hz, 1H), 7.76 (d, J=7.8 Hz, 1H), 7.81 (dd, J=8.2 Hz and 2.3 Hz), 7.95 (m, 2H), 8.04 (m, 3H), 8.82 (s, 2H), 10.44 (s, 1H). (m/z)=457 (M+H)⁺.

Example 76

Synthesis of N-(5-(3-(2-cyanopropan-2-yl)benzamido)-2-methylphenyl)-2-ethoxythieno[2,3-b]pyrazine-6-carboxamide

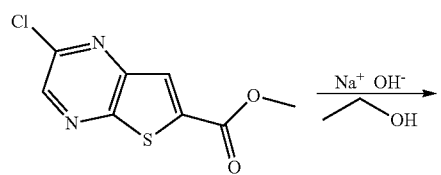

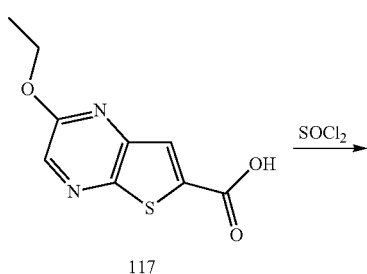

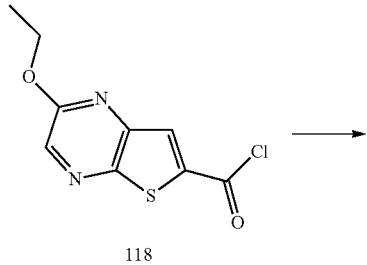

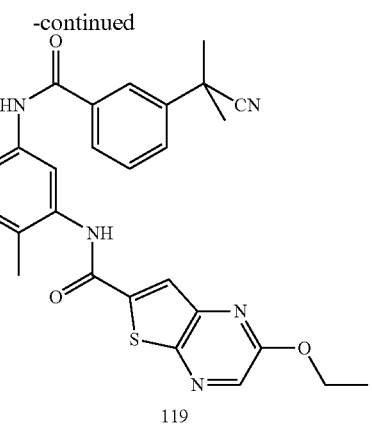

119

Step 1: synthesis of 2-ethoxythieno[2,3-b]pyrazine-6-carboxylic acid (117)

To a solution of methyl 2-chlorothieno[3,2-b]pyrazine-6-carboxylate 22 (100 mg, 0.437 mmol) in THF (1.8 mL) and ethanol (1.2 mL) was added 2N sodium hydroxide (1.09 mL, 2.19 mmol). The reaction was stirred overnight at 50° C. The reaction mixture was poured in citric acid solution and the resulting precipitate was collected, washed with water and dried to give crude 2-ethoxythieno[2,3-b]pyrazine-6-carboxylic acid (60 mg, 61%). (m/z)=225 (M+H)⁺.

Step 2: synthesis of 2-ethoxythieno[2,3-b]pyrazine-6-carbonyl chloride (118)

A solution of 2-ethoxythieno[2,3-b]pyrazine-6-carboxylic acid (30 mg, 0.134 mmol) in thionyl chloride (1 mL) was stirred at 80° C. for 2 h. Evaporated to dryness and co-evaporated with toluene to give 2-ethoxythieno[2,3-b]pyrazine-6-carbonyl chloride (32 mg, 100%).

Step 3: synthesis of N-(5-(3-(2-cyanopropan-2-yl)benzamido)-2-methylphenyl)-2-ethoxythieno[2,3-b]pyrazine-6-carboxamide (119)

To a solution of N-(3-amino-4-methylphenyl)-3-(2-cyanopropan-2-yl)benzamide 5 (38 mg, 0.132 mmol) and triethylamine (0.092 mL, 0.66 mmol) in CH₂Cl₂ (1 mL) was added 2-ethoxythieno[2,3-b]pyrazine-6-carbonyl chloride (32 mg, 0.132 mmol) in CH₂Cl₂ (1 mL) and stirred overnight at rt. Water was added and extracted with CH₂Cl₂. Organic layer was washed with water, dried and evaporated. Purification by HPLC gave N-(5-(3-(2-cyanopropan-2-yl)benzamido)-2-methylphenyl)-2-ethoxythieno[2,3-b]pyrazine-6-carboxamide (5 mg, 7%). ¹H-NMR (400 MHz, DMSO-d6). 1.42 (t, J=7.0 Hz, 3H), 1.76 (s, 6H), 2.26 (s, 3H), 4.46 (q, J=7.0 Hz and 14.0 Hz, 2H), 7.31 (d, 8.2 Hz, 1H), 7.58-7.66 (m, 2H), 7.76 (d, J=7.8 Hz, 1H), 7.87 (d, J=1.9 Hz, 1H), 7.95 (d, J=7.8 Hz, 1H), 8.05 (s, 1H), 8.35 (s, 1H), 8.41 (s, 1H), 10.35 (s, 1H), 10.37 (s, 1H). (m/z)=500 (M+H)⁺.

Example 77

Determination of B-Raf Kinase Activity using an IMAP Assay

Inhibition of B-Raf kinase activity was measured using an Immobilized Metal Assay for Phosphochemicals-based coupled assay (IMAP). IMAP is a homogeneous fluorescence polarization (FP) assay based on affinity capture of phosphorylated peptide substrates. IMAP uses fluorescein-labeled peptide substrates that, upon phosphorylation by a protein kinase, bind to so called IMAP nanoparticles, which are derivatized with trivalent metal complexes. Such binding causes a change in the rate of the molecular motion of the peptide, and results in an increase in the FP value observed for the fluorescein label attached to the substrate peptide. In this assay, B-Raf phosphorylates unactive MEK1. The phosphorylated MEK1 is capable of phosphorylating ERK2, which subsequently phosphorylates the fluorescein-labeled peptide substrate.

Enzymes, substrate and ATP were diluted at all steps in Kinase Reaction buffer (10 mM Tris-HCl, 10 mM MgCl2, 0.01% Tween-20, 0.05% NaN3 pH 7.2, 1 mM DTT). The final volume at the kinase reaction step of the assay in the 384-well plate was 20 µl. The concentrations within brackets are final concentrations in the assay. B-Raf (GST-tagged human recombinant active B-Raf (Δ1-415), Upstate/Millipore; 0.2 U/ml) was pre-incubated with compounds or DMSO (1% final concentration) for 60 minutes at room temperature in the dark. Thereafter, MEK 1 (GST-tagged human recombinant unactive MEK1 (full-length); 64 ng/ml), ERK2 (GST-tagged human recombinant unactive ERK2 (full-length); 600 ng/ml), peptide substrate (Erktide, Molecular Devices; 50 nM) and ATP (50 µM) were added to the wells and the mix was incubated for another 60 minutes at 30° C. in the dark. Then, IMAP progressive binding buffer (75% 1× buffer A, 25% 1× buffer B, 1:900 Progressive Binding Reagent; Molecular Devices) was added followed by an incubation step of 60 minutes at room temperature in the dark. Finally, the FP signal was read on an Envision Multilabel reader (Perkin Elmer).

All compounds exemplified have been tested in the B-Raf IMAP assay and exhibit $IC_{50}$ below 1000 nM ($pIC_{50}$>6). The compounds from examples 3, 7, 11, 12, 13, 14, 16, 17, 19, 21, 23, 25, 26, 28, 30, 31, 32, 33, 34, 35, 36, 37, 38, 39, 40, 46, 47, 48, 49, 50, 51, 52, 53, 55, 56, 57, 58, 67, 68, 70, 71, 73, 74 and 76 exhibit $IC_{50}$s below 100 nM ($pIC_{50}$>7). The compounds from examples 1, 2, 4, 5, 6, 8, 9, 10, 15, 18, 20, 22, 24, 27, 29, 41, 42, 43, 44, 54, 60, 61, 62, 63, 64, 65, 66 and 69 exhibit $IC_{50}$s below 10 nM ($pIC_{50}$>8).

Example 78

Determination of B-Raf Activity Using a A375 (B-Raf mutated) Melanoma Cell Line (Phospho-ERK FACE Assay)

Inhibition of phosphorylation of ERK1/2 was measured using a Fast Activated Cell-based ELISA (FACE) from Active Motif (Carlsbad, U.S.A., CA). Briefly, A375 cells, which are cells containing a mutant form of B-Raf (V600E) and thus contain high levels of phosphorylated ERK, were incubated for 2 hours with Raf inhibitors. Then, cells were fixed with paraformaldehyde, washed and following quenching and blocking, incubated with anti-phospho-ERK antibody, and as a control, on a separate plate, with ERK antibody. After washing and removal of the primary antibodies, the fixed cells were incubated with horse radish peroxidase (HRP)-labeled secondary antibody. Finally, chemiluminescence reagents were added, which react with HRP, to give a luminescence signal.

Detailed protocol: A375 cells were cultured in DMEM/F12 (Dulbecco's Modified Eagle Medium Nutrient Mixture F-12) (Invitrogen), supplemented with 10% fetal bovine serum (FBS) (Biowhittaker), 100 U/ml penicillin G and 100 µg/ml streptomycin (Gibco). For the phospho ERK assay, cells were seeded at a density of 15,000 cells/well in 100 µl culture medium in 96-well plates and incubated in a humidified atmosphere at 5% $CO_2$ and 37° C. After 24 hours, cells were washed with DMEM/F12 supplemented with 0.1% FBS (assay medium 120 µl of assay medium was added and the plates were incubated overnight in a humidified atmosphere at 5% $CO_2$ and 37° C. The next day, the assay medium was removed and compounds diluted in assay medium were added to the cells. Final DMSO concentration in the assay was 1%. After 2 hours incubation, cells were fixed by replacing the assay medium with 100 µl of 4% formaldehyde (Bio-Connect, Huissen, The Netherlands) in PBS. After 20 minutes of incubation at room temperature, cells were washed three times with 200 µl wash buffer (0.1% (vol/vol) Triton X-100 in PBS from the FACE kit) followed by an incubation of 20 minutes with 100 µl quenching buffer, containing 1% (vol/vol) hydrogen peroxide (Thermo Fisher Scientific) and 0.1% (vol/vol) sodium azide (Sigma-Aldrich) in phosphate-buffered saline. Cells were washed two times with wash buffer, incubated for 1 hour with 100 µl antibody blocking buffer from the kit and washed two times again. 40 µl of diluted antibody against phosphorylated ERK1/2 (1:500 from the FACE kit) was added and incubated overnight at 4° C. The phospho-ERK antibody has been raised against a synthetic phospho-peptide corresponding to residues Thr202 and Tyr204 of human ERK1 and Thr185 and Tyr187 of human ERK2. For the detection of total ERK, antibody against ERK1 and ERK2 (1:500 from the FACE kit) was added. The excessive primary antibody was washed out, and 100 µl diluted HRP-conjugated anti-rabbit IgG (1:2000 from the FACE kit) was added and incubated for 1 hour at room temperature. Secondary antibody was removed and cells were washed 3 times with wash buffer and twice with PBS. 50 µl per well of FACE chemiluminescent working solution was added. Chemiluminescence was measured on an Envision Multilabel reader.

A selection of the compound exemplified, have been tested in the A375 melanoma assay. Compounds from examples 14, 19, 26, 32, 35, 36, 37, 39, 40, 55 and 66 exhibit IC50's in this assay between 10 µM and 1 µM (5<pIC50<6). Compounds from examples 3, 5, 8, 17, 18, 24, 27, 28, 29, 30, 31, 38, 41, 42, 43, 44, 49, 51, 53, 59, 61, 62, 63, 64, 65, 67, 68, 70 and 73 exhibit IC50s in this assay between 1 µM and 100 nM (6<pIC50<7). Compounds from examples 1, 2, 4, 6, 7, 9, 10, 11, 13, 15, 16, 20, 21, 46, 50, 54 and 69 exhibit IC50s in this assay below 100 nM (pIC50>7).

Abbreviations

HATU: O-(7-AZABENZOTRIAZOL-1-YL)-N,N,N',N'-TETRAMETHYLURONIUM HEXAFLUOROPHOSPHATE.
TBTU: O-BENZOTRIAZOL-1-YL-N,N,N',N'-TETRAMETHYLURONIUM TETRAFLUOROBORATE.
DMF: N,N-DIMETHYLFORMAMIDE.
NaCN: SODIUM CYANIDE.
TBME: TERT-BUTYL METHYL ETHER.
$Na_2SO_4$: SODIUM SULFATE.
DMSO: DIMETHYL SULFOXIDE.
NaH: SODIUM HYDRIDE.
$CH_3I$: METHYL IODIDE.
EtOAc: ETHYL ACETATE.
THF: TETRAHYDROFURAN.
MeOH: METHANOL.
LiOH: LITHIUM HYDROXIDE.
HCl: HYDROCHLORIC ACID.

CH₂Cl₂: DICHLOROMETHANE.
DIPEA: N,N-DIISOPROPYLETHYLAMINE.
CH₃COOH: ACETIC ACID.
NaOH: SODIUM HYDROXIDE.
EtOH: ETHANOL.
KOH: POTASSIUM HYDROXIDE.
ACN: ACETONITRILE.
NH₄Cl: AMMONIUM CHLORIDE.
NaHCO₃: SODIUM HYDROGENCARBONATE.
NMP: 1-METHYL-2-PYRROLIDINONE.
CDCl₃: CHLOROFORM-D.
DMSO-d6: DIMETHYL SULFOXIDE-D6.
K₂CO₃: POTASSIUM CARBONATE.
Na₂CO₃: SODIUM CARBONATE.
TEA: TRIETHYLAMINE.
H₂SO₄: SULFURIC ACID.
NH₄OH: AMMONIUM HYDROXIDE.
POCl₃: PHOSPHORUS OXYCHLORIDE.
SOCl₂: THIONYL CHLORIDE.
Pd/C: PALLADIUM ON ACTIVATED CARBON.
DPPA: DIPHENYLPHOSPHORYL AZIDE.
HNO₃: NITRIC ACID.
TFA: TRIFLUOROACETIC ACID.
NMR: NUCLEAR MAGNETIC RESONANCE.
HPLC: HIGH PERFORMANCE LIQUID CHROMATOGRAPHY.

What is claimed is:

1. A compound according to Formula I

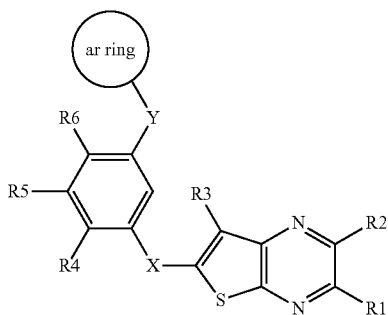

Formula I or a pharmaceutically acceptable salt thereof, wherein:
one of R1 and R2 is H; halogen; hydroxy; CN; amino; (1-2C)alkyl; (1-2C)alkylcarbonyl; (1-2C)alkoxy; or (di)[(1-2C)alkyl]amino, the alkyl group of which is optionally substituted with hydroxy;
and the other R1 and R2 is H; halogen; hydroxy; CN; amino; (1-6C)alkyl; (1-6C)alkoxy; (di)[(1-6C)alkyl]amino, the alkyl group of which is optionally substituted with one or more hydroxy, (di)[(1-4C)alkyl]amino, (1-6C)alkoxy, (2-5C)heterocycloalkyl or (2-5C)heteroaryl; (1-6C)alkylcarbonyl; (2-5C)heterocycloalkyl, optionally substituted with one or more groups selected from hydroxy, amino, (1-6C)alkyloxycarbonylamino or (1-6C)alkyl, the alkyl group of which is optionally substituted with hydroxy; (2-5C)heteroaryl or (2-5C)heteroarylamino, both optionally substituted with halogen, CN, (1-6C)alkoxy, (di)[(1-6C)alkyl]amino or (1-6C)alkyl; phenyl or phenylamino, both optionally substituted with halogen, CN, (1-6C)alkyl, (1-6C)alkoxy or (di)[(1-6C)alkyl]amino; or (2-5C)heterocycloalkylamino;
R3 is H; amino; halogen; hydroxy; cyano; (1-6C)alkyl; (2-6C)alkenyl; (2-6C)alkynyl; (di)[(1-4C)alkyl]amino; (1-4C)alkylcarbonylamino, the alkyl group of which optionally is substituted with halogen; or phenylalkyl, the phenyl group of which is optionally substituted with halogen;
R4 is (1-4C)alkyl; halogen; or cyano;
R5 and R6 are independently H or halogen;
X is NHCO; CONH; N=C(CN); NHCH₂; NHSO₂; SO₂NH; or CO;
Y is CONH; NHCO; NHCONH; NHSO₂; or SO₂NH;
ar ring is an aryl ring selected from (2-5C)heteroaryl substituted with one or more groups selected from halogen, (1-6C)alkyl, phenyl, (2-5C)heterocycloalkyl, or (di)[(1-6C)alkyl]amino optionally substituted with (1-6C)alkoxy, OH, or (di)[(1-6C)alkyl]amino; or phenyl having Formula II

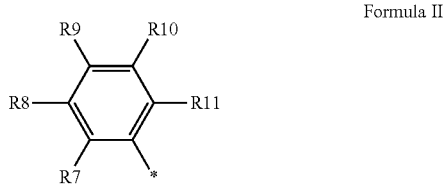

Formula II wherein:
R7 and R11 are independently H; halogen; (1-6C)alkyl; (di)[(1-6C)alkyl]amino; or amino;
R8, R9 and R10 are independently H; halogen; amino; (1-6C)alkyl, optionally substituted with one or more CN, aminocarbonyl, halogen, hydroxy, phenyl or (2-5C)heterocycloalkyl; (1-6C)alkoxy, optionally substituted with one or more halogen, hydroxy or (1-6)alkoxy; (di)[(1-6C)alkyl]amino, optionally substituted with phenyl; (2-5C)heteroaryl; (2-5C)heterocycloalkyl, optionally substituted with cyano or (1-6C)alkyl; (di)[(1-6C)alkyl] amino); (1-6C)alkylcarbonyl: or phenylamino.

2. The compound according to claim 1 wherein the ar ring is phenyl having Formula II

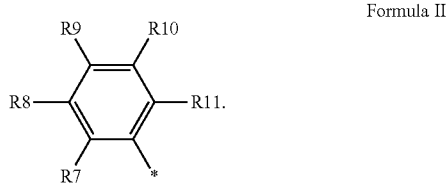

Formula II

3. The compound according to claim 2 wherein R8 in the phenyl ring is (1-4C)alkyl, optionally substituted with one or more CN, aminocarbonyl or halogen; (1-4C)alkoxy; (di)[(1-4C)alkyl]amino; or (2-5C)heteroaryl.

4. The compound according to claim 3 wherein R8 in the phenyl ring is (1-4C)alkyl, optionally substituted with one or more CN or halogen.

5. The compound according to claim 2 wherein R7, R9, R10 and R11 are H.

6. The compound according to claim 1 wherein R1 is H; halogen; hydroxy; CN; amino; (1-2C)alkyl; (1-2C)alkylcarbonyl; (1-2C)alkoxy; or (di)[(1-2C)alkyl]amino, the alkyl group of which is optionally substituted with hydroxy; and
R2 is H; halogen; hydroxy; CN; amino; (1-6C)alkyl; (di)[(1-6C)alkyl]amino, the alkyl group of which is optionally substituted with one or more hydroxy, (di)[(1-4C)alkylamino, (1-6C)alkoxy, (2-5C)heterocycloalkyl or (2-5C)heteroaryl; (1-4C)alkylcarbonyl; (1-4C)alkoxy, optionally substituted with (di)[(1-4C)alkyl]amino; (2-5C)heterocycloalkyl, optionally substituted with one or more groups selected from hydroxy, amino, (1-6C)alkyloxycarbonylamino), or (1-4C)alkyl, the alkyl group of which is optionally substituted with hydroxy; (2-5C)heteroaryl, optionally substituted with halogen, CN, (1-4C)alkoxy, (di)[(1-4C)alkyl]amino or (1-4C)alkyl; phenyl, optionally substituted with halogen, CN, (1-4C)alkyl, (1-4C)alkoxy or (di)[(1-4C)alkyl]amino; (2-5C)heteroarylamino; phenylamino; or (2-5C)heterocycloalkylamino.

7. The compound according to claim 6 wherein R1 is H; halogen; hydroxy; CN; amino; (1-2C)alkyl; (1-2C)alkylcarbonyl; (1-2C)alkoxy; or (di)[(1-2C)alkyl]amino, the alkyl group of which is optionally substituted with hydroxy; and R2 is H; halogen; hydroxy; CN; amino; (1-6C)alkyl; (1-6C)alkoxy; (di)[(1-6C)alkyl]amino, the alkyl group of which is optionally substituted with one or more hydroxy, (di)[(1-4C)alkylamino, (1-6C)alkoxy, (2-5C)heterocycloalkyl or (2-5C)heteroaryl; or (2-5C)heteroaryl.

8. The compound according to claim 7 wherein R2 is H or (di)[(1-2C)alkyl]amino, the alkyl group of which is optionally substituted with hydroxy.

9. The compound according to claim 6 wherein R1 is H or (di)[(1-2C)alkyl]amino, the alkyl group of which is optionally substituted with hydroxy.

10. The compound according to claim 1 wherein X and Y are independently NHCO or CONH.

11. The compound according to claim 10 wherein X is NHCO.

12. The compound according to claim 11 wherein Y is CONH.

13. The compound according to claim 1 wherein the ar ring is (2-5C)heteroaryl substituted with one or more groups selected from (1-6C)alkyl, phenyl, (di)[(1-4C)alkyl]amino or pyrrolidinyl.

14. The compound according to claim 1 wherein at least one of R1 or R2 is H.

15. The compound according to claim 1 wherein R3 is H, amino or (di)[(1-4C)alkyl]amino.

16. The compound according to claim 1 wherein R5 and R6 are independently H.

17. A pharmaceutical composition comprising the compound of claim 1 in combination with a pharmaceutically acceptable carrier or diluent.

* * * * *